United States Patent
Kim

(10) Patent No.: US 10,463,337 B2
(45) Date of Patent: *Nov. 5, 2019

(54) X-RAY DETECTOR, X-RAY IMAGING APPARATUS AND METHOD OF CONTROLLING THE SAME

(71) Applicant: SAMSUNG ELECTRONICS CO., LTD., Suwon-si, Gyeonggi-do (KR)

(72) Inventor: Myeong Je Kim, Seoul (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 221 days.

This patent is subject to a terminal disclaimer.

(21) Appl. No.: 15/583,529

(22) Filed: May 1, 2017

(65) Prior Publication Data

US 2017/0231595 A1 Aug. 17, 2017

Related U.S. Application Data

(63) Continuation of application No. 14/534,601, filed on Nov. 6, 2014, now Pat. No. 9,668,706.

(30) Foreign Application Priority Data

| Nov. 6, 2013 | (KR) | 10-2013-0134415 |
| Sep. 3, 2014 | (KR) | 10-2014-0116758 |
| Nov. 6, 2014 | (KR) | 10-2014-0153513 |

(51) Int. Cl.
*A61B 6/00* (2006.01)
*A61B 6/04* (2006.01)
*A61B 6/10* (2006.01)

(52) U.S. Cl.
CPC ............ *A61B 6/547* (2013.01); *A61B 6/4233* (2013.01); *A61B 6/4283* (2013.01);
(Continued)

(58) Field of Classification Search
CPC .......................... G03B 42/025; G03B 42/047
See application file for complete search history.

(56) References Cited

U.S. PATENT DOCUMENTS

| 2007/0153980 A1 | 7/2007 | Butzine et al. |
| 2008/0292062 A1 | 11/2008 | Marar |

(Continued)

FOREIGN PATENT DOCUMENTS

| CN | 101052351 | 10/2007 |
| CN | 102293657 | 12/2011 |

(Continued)

OTHER PUBLICATIONS

Chinese Patent Office Action dated Aug. 25, 2017 in Chinese Patent Application No. 201480072454.8 (Total page count 24).

(Continued)

*Primary Examiner* — Hoon K Song
(74) *Attorney, Agent, or Firm* — Staas & Halsey LLP

(57) ABSTRACT

An X-ray detector that is detachably mountable in a mounting unit, the detector comprises a storage unit configured to store identification (ID) information, which is assigned to the X-ray detector according to its usage, of the X-ray detector, a position detecting unit configured to detect a mounting position information of the X-ray detector and a communication unit configured to transmit the mounting position information of the X-ray detector and ID information of the X-ray detector to a workstation.

16 Claims, 137 Drawing Sheets

(52) U.S. Cl.
CPC .............. *A61B 6/4405* (2013.01); *A61B 6/56* (2013.01); *A61B 6/563* (2013.01); *A61B 6/0407* (2013.01); *A61B 6/107* (2013.01); *A61B 6/4464* (2013.01); *A61B 6/4494* (2013.01); *A61B 6/548* (2013.01)

(56) References Cited

U.S. PATENT DOCUMENTS

| | | | |
|---|---|---|---|
| 2009/0032744 | A1 | 2/2009 | Kito et al. |
| 2009/0032745 | A1 | 2/2009 | Kito et al. |
| 2010/0123083 | A1 | 5/2010 | Petrick et al. |
| 2011/0051902 | A1 | 3/2011 | Liu et al. |
| 2011/0075817 | A1* | 3/2011 | Takahashi .............. G03B 42/04 378/189 |
| 2011/0110494 | A1* | 5/2011 | Lee ........................ G03B 42/04 378/98 |

FOREIGN PATENT DOCUMENTS

| | | |
|---|---|---|
| JP | 2002-336225 | 11/2002 |
| JP | 2009-50693 | 3/2009 |
| JP | 2011-50736 | 3/2011 |
| JP | 2011-67314 | 4/2011 |
| KR | 10-2009-0124927 | 12/2009 |
| WO | WO 2010/134365 | 11/2010 |

OTHER PUBLICATIONS

Chinese Patent Office Action dated Apr. 16, 2018 in corresponding Chinese Patent Application No. 201480072454.8, pp. 11.
European Office Action dated Apr. 19, 2017 in corresponding European Patent Application No. 14 814 727.5, pp. 4.
European Patent Office issued Communication under Rule 71(3) EPC dated Oct. 18, 2018 in EP Application No. 14 814 727.5 (5 pages).
European Patent Office issued Annex to EPO Form 2004, Communication pursuant to Rule 71(3) EPC dated Oct. 18, 2018 in EP Application No. 14 814 727.5 (2 pages).
National Intellectual Property Administration, PRC (People's Republic of China) issued Notification of Due Registration Formalities Sep. 30, 2018 in Chinese Application No. 201480072454.8 (7 total pages).
Office Action dated Feb. 20, 2015 in U.S. Appl. No. 14/534,601 (11 pages).
Final Office Action dated Aug. 4, 2015 in U.S. Appl. No. 14/534,601 (16 pages).
Office Action dated Oct. 22, 2015 in U.S. Appl. No. 14/534,601 (12 pages).
Notice of Allowance dated May 20, 2016 in U.S. Appl. No. 14/534,601 (12 pages).
PCT International Search Report dated Feb. 17, 2015 in corresponding International Patent Application No. PCT/KR2014/010633.
Korean Office Action dated Jan. 19, 2016 in corresponding Korean Patent Application No. 10-2014-0153513.
European Search Report in Application No. 14814727.5 dated Jun. 15, 2016 (6 pages).
Korean Notice of Allowance dated Aug. 30, 2016 in corresponding Korean Patent Application No. 10-2014-0153513.
Communication pursuant to Article 94(3) EPC dated Apr. 19, 2017 in corresponding European Patent Application No. 14 814 727.5-1666 (4 pages).
U.S. Appl. No. 14/534,601, filed Nov. 6, 2014, Myeong Je Kim, Samsung Electronics Co., Ltd.
Extended European Search Report dated Jul. 17, 2019 in corresponding European Patent Application No. 19164973.0.
European Office Action dated Apr. 26, 2019 in corresponding European Patent Application No. 14814727.5.

\* cited by examiner

FIG. 13B
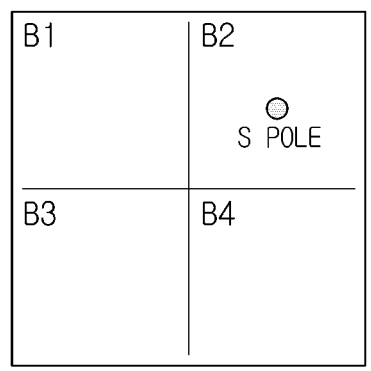
TABLE MOUNTING UNIT
310
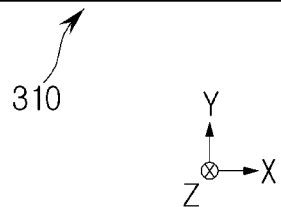

FIG. 14

|  | X | Y | Z |
|---|---|---|---|
| TABLE MOUNTING UNIT | + | + | + |
| STAND MOUNTING UNIT | − | − | + |

FIG. 16

|                       | X | Y | Z |
|-----------------------|---|---|---|
| TABLE MOUNTING UNIT   | + | + | + |
| STAND MOUNTING UNIT   | − | − | + |
| PORTABLE MOUNTING UNIT| + | − | + |

FIG. 24A

FIRST SENSOR GROUP

|  | X | Y | Z |
|---|---|---|---|
| $M_{11}$ | + | − | + |
| $M_{12}$ | − | − | + |
| $M_{13}$ | + | + | + |
| $M_{14}$ | − | + | + |

SECOND SENSOR GROUP

|  | X | Y | Z |
|---|---|---|---|
| $M_{21}$ | + | + | + |
| $M_{22}$ | + | + | + |
| $M_{23}$ | + | + | + |
| $M_{24}$ | + | + | + |

FIG. 24B

FIRST SENSOR GROUP

|     | X | Y | Z |
|-----|---|---|---|
| $M_{11}$ | − | − | + |
| $M_{12}$ | − | − | + |
| $M_{13}$ | − | − | + |
| $M_{14}$ | − | − | + |

SECOND SENSOR GROUP

|     | X | Y | Z |
|-----|---|---|---|
| $M_{21}$ | + | − | + |
| $M_{22}$ | − | − | + |
| $M_{23}$ | + | + | + |
| $M_{24}$ | − | + | + |

FIG. 26A

FIRST SENSOR GROUP

| | X | Y | Z |
|---|---|---|---|
| $M_{11}$ | + | − | + |
| $M_{12}$ | − | − | + |
| $M_{13}$ | + | + | + |
| $M_{14}$ | − | + | + |

SECOND SENSOR GROUP

| | X | Y | Z |
|---|---|---|---|
| $M_{21}$ | + | + | + |
| $M_{22}$ | + | + | + |
| $M_{23}$ | + | + | + |
| $M_{24}$ | + | + | + |

FIG. 26B

FIRST SENSOR GROUP

| | X | Y | Z |
|---|---|---|---|
| $M_{11}$ | − | − | + |
| $M_{12}$ | − | − | + |
| $M_{13}$ | − | − | + |
| $M_{14}$ | − | − | + |

SECOND SENSOR GROUP

| | X | Y | Z |
|---|---|---|---|
| $M_{21}$ | + | − | + |
| $M_{22}$ | − | − | + |
| $M_{23}$ | + | + | + |
| $M_{24}$ | − | + | + |

FIG. 26C

FIRST SENSOR GROUP

|  | X | Y | Z |
|---|---|---|---|
| $M_{11}$ | − | − | + |
| $M_{12}$ | − | − | + |
| $M_{13}$ | − | − | + |
| $M_{14}$ | − | − | + |

SECOND SENSOR GROUP

|  | X | Y | Z |
|---|---|---|---|
| $M_{21}$ | + | + | + |
| $M_{22}$ | − | − | + |
| $M_{23}$ | + | + | + |
| $M_{24}$ | − | − | + |

FIG. 28A

FIRST SENSOR GROUP

|  | X | Y | Z |
|---|---|---|---|
| $M_{11}$ | + | − | + |
| $M_{12}$ | + | − | + |
| $M_{13}$ | + | + | + |
| $M_{14}$ | + | + | + |

SECOND SENSOR GROUP

|  | X | Y | Z |
|---|---|---|---|
| $M_{21}$ | + | + | + |
| $M_{22}$ | + | + | + |
| $M_{23}$ | + | + | + |
| $M_{24}$ | + | + | + |

FIG. 28B

FIRST SENSOR GROUP

| | X | Y | Z |
|---|---|---|---|
| $M_{11}$ | − | − | + |
| $M_{12}$ | − | − | + |
| $M_{13}$ | − | − | + |
| $M_{14}$ | − | − | + |

SECOND SENSOR GROUP

| | X | Y | Z |
|---|---|---|---|
| $M_{21}$ | + | − | + |
| $M_{22}$ | + | − | + |
| $M_{23}$ | + | + | + |
| $M_{24}$ | + | + | + |

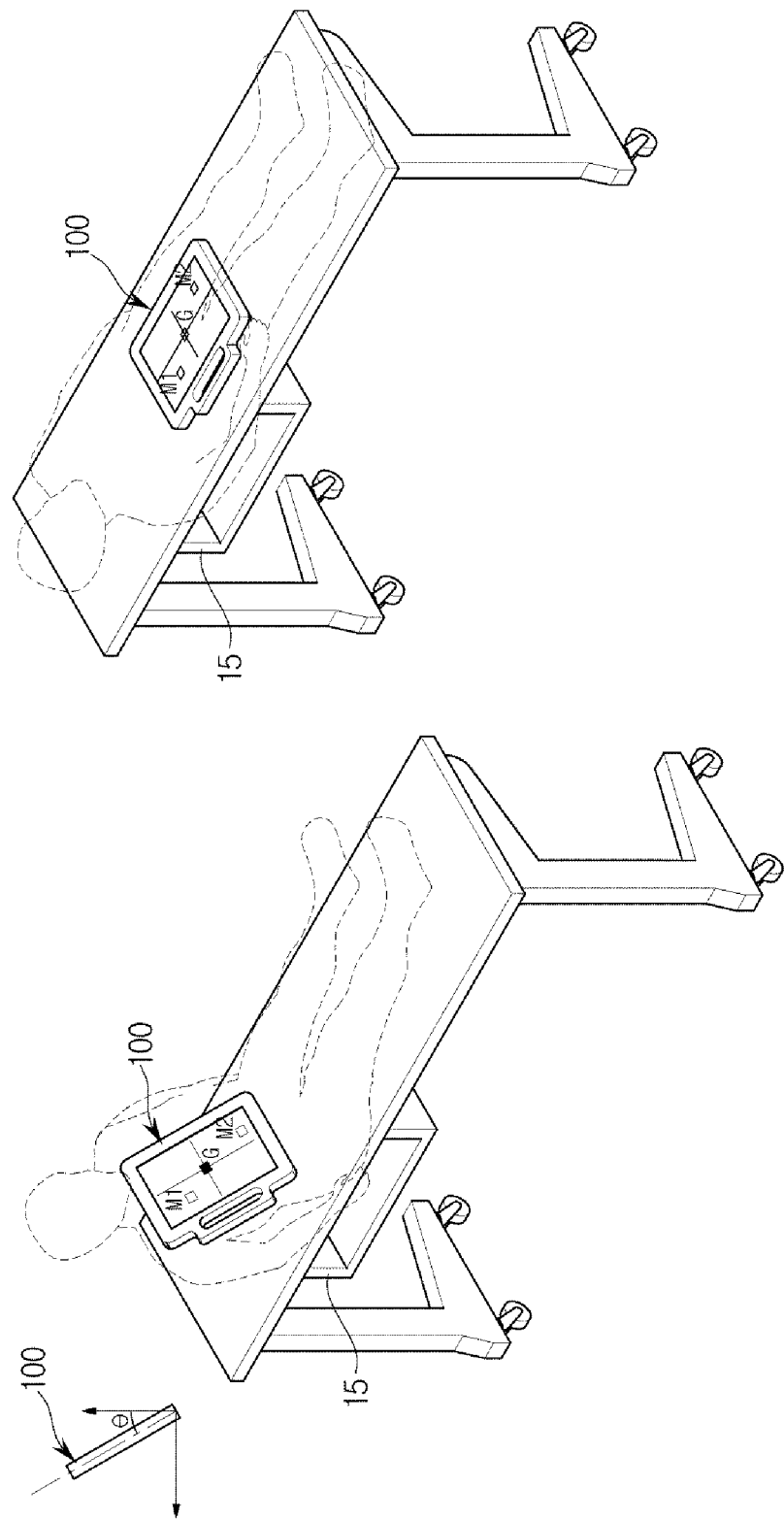

X-RAY DETECTOR, X-RAY IMAGING APPARATUS AND METHOD OF CONTROLLING THE SAME

CROSS-REFERENCE TO RELATED APPLICATION

This application is a Continuation of U.S. patent application Ser. No. 14/534,601, filed on Nov. 6, 2014, which claims the foreign priority benefit of Korean Patent Application No. 10-2013-0134415, filed on Nov. 6, 2013, Korean Patent Application No. 10-2014-0116758, filed on Sep. 3, 2014, and Korean Patent Application No. 10-2014-0153513, filed on Nov. 6, 2014, filed in the Korean Intellectual Property Office, the disclosures of which are incorporated herein by reference.

BACKGROUND

1. Field

The embodiments relate to an X-ray imaging apparatus including an X-ray detector configured to detect a position and a method of controlling the same.

2. Description of the Related Art

The X-ray imaging apparatus includes an X-ray source configured to generate X-rays and radiate the X-rays onto the object and an X-ray detector configured to detect the X-rays transmitted through the object. The X-ray source may be movably provided in order to image various parts of the object and the X-ray detector may be mounted or portably provided in an imaging table or an imaging stand.

As X-ray imaging apparatuses are becoming digitalized, X-ray images that have previously been obtained in a film form are being obtained in a digital form. Along with digitalization, many parts of X-ray imaging apparatuses are becoming automated. Examples of the automation include an auto tracking function of automatically tracking the X-ray detector by the X-ray source and an auto centering function of automatically aligning positions of the X-ray source and the X-ray detector. In order to implement the automation functions of X-ray imaging apparatuses such as the auto tracking function or the auto centering function, it may be necessary to accurately distinguish an X-ray detector and a mounting position thereof in advance.

SUMMARY

The embodiments provide an X-ray detector configured to detect a position, an X-ray imaging apparatus including the X-ray detector, and a method of controlling the same.

The X-ray detector is an X-ray detector that is mounted in a mounting unit or is portably provided without being mounted in the mounting unit, and may include a storage unit configured to store identification (ID) information of the X-ray detector; and a detecting unit configured to detect a mounting position of the X-ray detector.

The mounting unit may include at least one of a table mounting unit provided in an imaging table, a stand mounting unit provided in an imaging stand, and a portable mounting unit having a grid.

The detecting unit may include a magnetic sensor to detect at least one of a magnetic field direction and a magnetic field strength.

The magnetic sensor may include a linear magnetic sensor to output a value corresponding to the detected magnetic field strength.

The magnetic sensor may include a non-linear magnetic sensor to output on or off according to whether the magnetic field strength is equal to or greater than a threshold value.

The detecting unit may include a tilt sensor to detect a tilt.

The detecting unit may include a magnetic sensor to detect at least one of a magnetic field direction and a magnetic field strength, and a tilt sensor to detect a tilt.

The ID information may include an identification (ID) assigned to the X-ray detector.

The X-ray detector may further include an indicator to indicate whether the X-ray detector is connected to a workstation.

An X-ray imaging apparatus may include at least one X-ray detector including a storage unit configured to store identification (ID) information and a mounting position detecting unit; at least one mounting unit in which the at least one X-ray detector is mounted; and a control unit configured to determine the at least one X-ray detector is mounted in the at least one mounting unit based on at least one of the ID information and an output value of the mounting position detecting unit.

The at least one mounting unit may include a table mounting unit provided in the imaging table and a stand mounting unit provided in the imaging stand.

The at least one mounting unit may further include a portable mounting unit having a grid.

The at least one mounting unit may include one or more magnets, and the mounting position detecting unit may include one or more magnetic sensors to detect at least one of a magnetic field direction and a magnetic field strength.

One or more magnets include a first and second magnets; the table mounting unit may include the first magnet, the stand mounting unit may include the second magnet, and the first magnet and the second magnet are aligned by the same polarity.

The first magnet and the second magnet may be provided in positions that do not correspond to each other.

One ore more magnets include a first and second magnets; the table mounting unit may include the first magnet, the stand mounting unit may include the second magnet, and the first magnet and the second magnet may be aligned by different polarities.

The first magnet and the second magnet may be provided in positions that correspond to each other.

The control unit may determine the at least one mounting unit the at least one X-ray detector is mounted based on at least one the magnetic field direction and the magnetic field strength detected by the one or more magnetic sensors.

The mounting position detecting unit may include a tilt sensor to detect a tilt.

The control unit may determine in which mounting unit among the at least one mounting unit the at least one X-ray detector is mounted based on the tilt detected by the tilt sensor.

When the tilt sensor detects a horizontal state, the control unit may determine in which mounting unit among the at least one mounting unit the at least one X-ray detector is mounted based on a user's input.

The at least one mounting unit may include a magnet, and the mounting position detecting unit may include one or more magnetic sensors to detect at least one of a magnetic field direction and a magnetic field strength and a tilt sensor to detect a tilt.

The control unit may determine which X-ray detector among the at least one X-ray detector is mounted based on the ID information.

The ID information may include an identification (ID) assigned to the at least one X-ray detector.

The control unit may maintain or change the ID assigned to the at least one X-ray detector to correspond to a mounting position.

The at least one mounting unit may include a mount detecting unit configured to detect whether at least one X-ray detector is mounted.

The mount detecting unit may include a contact sensor or a non-contact sensor.

The mount detecting unit may include at least one of an ultrasonic sensor, an optical sensor, an RF sensor, and an image sensor.

A method of controlling an X-ray imaging apparatus may include receiving ID information and an output value of a mounting position detecting unit from at least one X-ray detector; and determining which X-ray detector among the at least one X-ray detector is mounted in the at least one mounting unit based on the ID information and the output value of the mounting position detecting unit.

According to the X-ray detector, the X-ray imaging apparatus, and the method of controlling the same, it is possible to determine an X-ray detector and a mounting position thereof. Also, the ID of the X-ray detector may be assigned or changed corresponding to the mounted position. Therefore, multi-use of the X-ray detector is possible and it is possible to provide convenience for the multi-use of the X-ray detector. Also, an X-ray source may be automatically moved or imaging conditions may be automatically set corresponding to the mounted position, and it is possible to provide convenience for user manipulation.

BRIEF DESCRIPTION OF THE DRAWINGS

FIG. 14 is a diagram illustrating a magnetic field detected by the linear magnetic sensor of FIG. 13;

FIG. 16 is a diagram illustrating a magnetic field detected by the linear magnetic sensor of FIG. 15;

FIGS. 24A and 24B are diagrams illustrating a magnetic field detected by the linear magnetic sensor of FIG. 23;

FIGS. 26A, 26B, 26C are diagrams illustrating a magnetic field detected by the linear magnetic sensor of FIG. 25;

FIGS. 28A and 28B are diagrams illustrating a magnetic field detected by the linear magnetic sensor of FIG. 27;

FIG. 39 is a diagram illustrating determination of an imaging part;

DETAILED DESCRIPTION

Hereinafter, exemplary embodiments of an X-ray imaging apparatus and a method of controlling the same will be described in detail with reference to the accompanying drawings.

Figure 1:
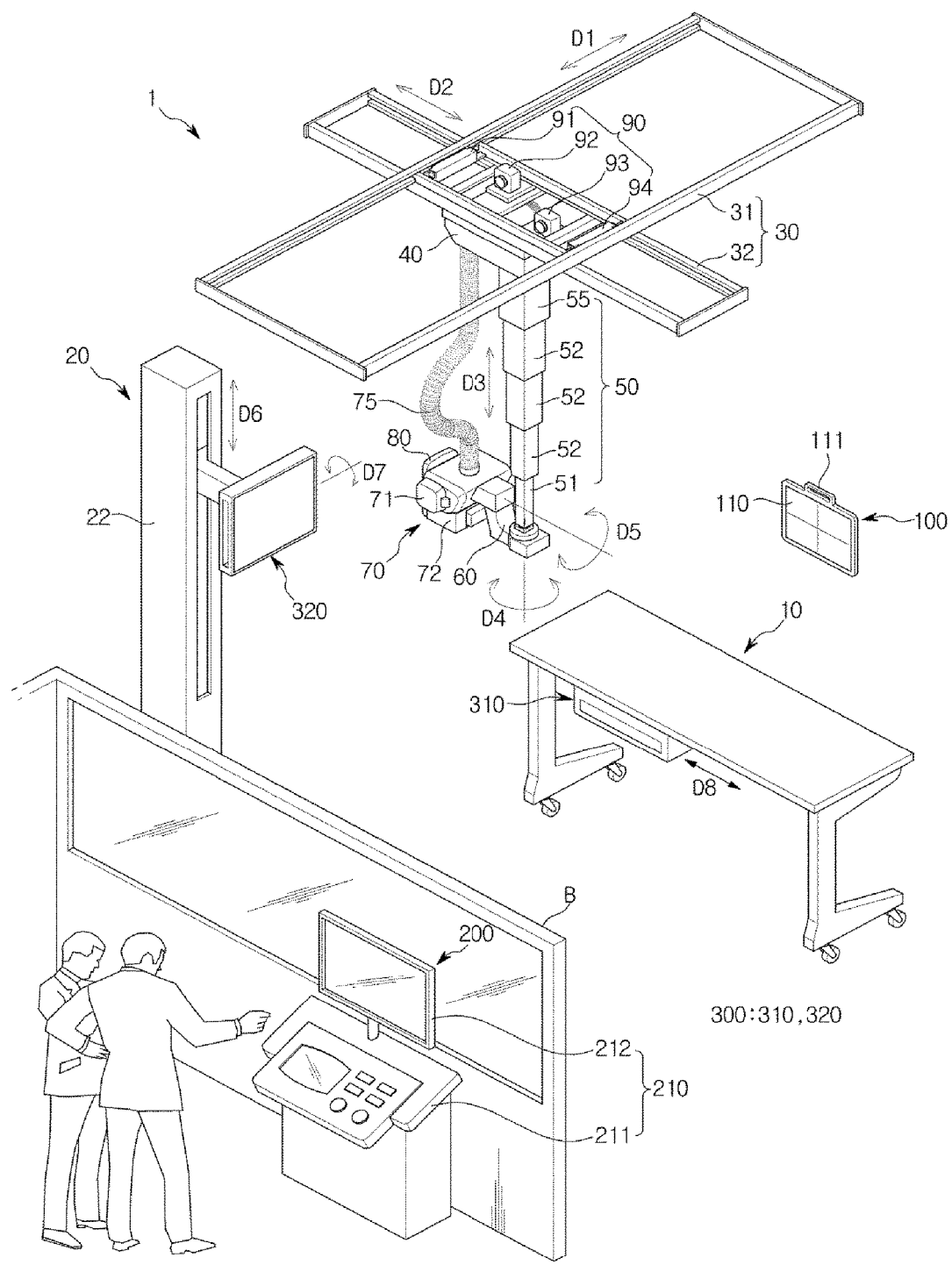
FIG. 1 is a perspective view illustrating an exemplary mobile X-ray imaging apparatus.
Figure 2:
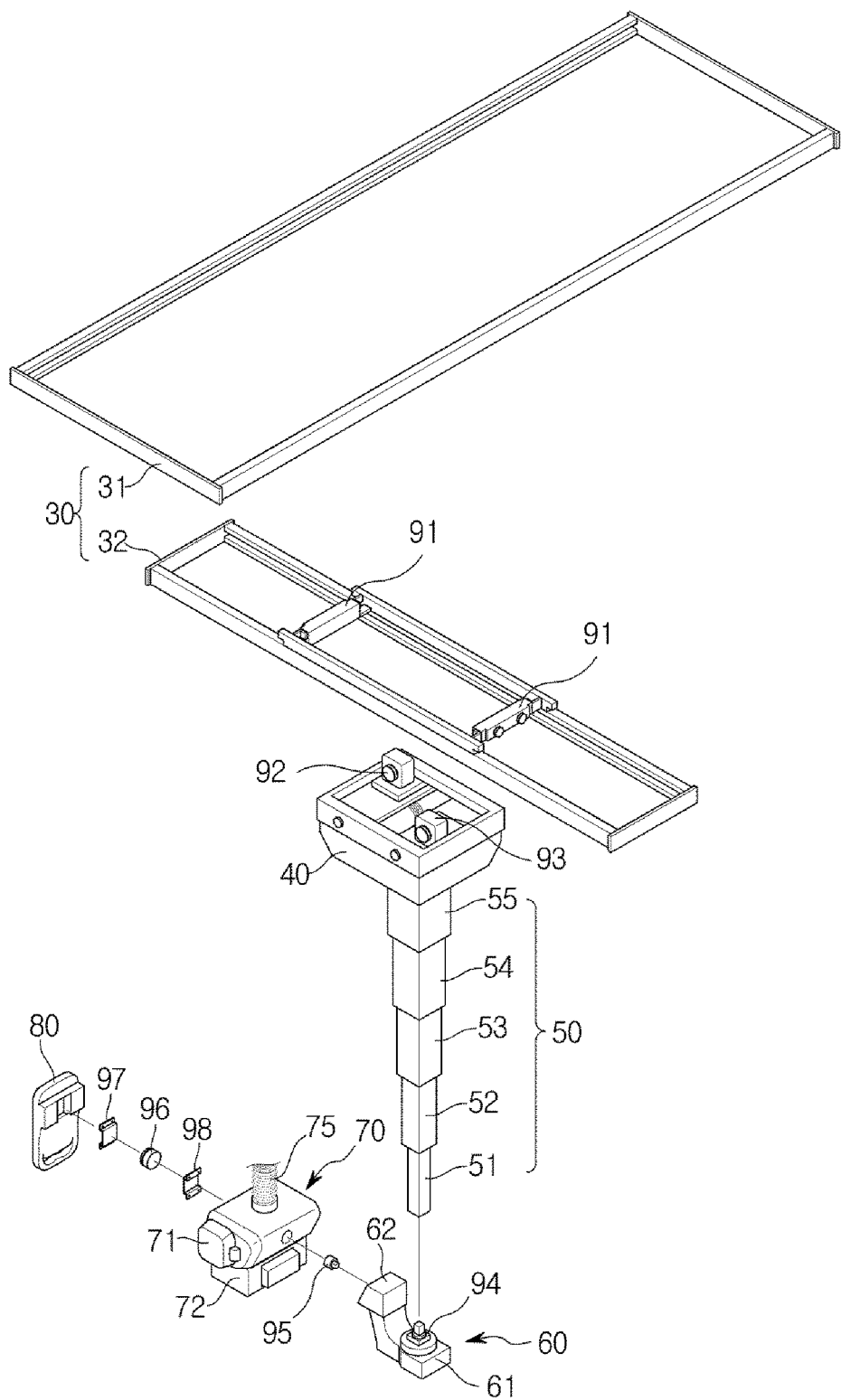
FIG. 2 is an exploded perspective view illustrating a disassembled X-ray imaging apparatus.

FIG. 1 is a perspective view illustrating an exemplary X-ray imaging apparatus. FIG. 2 is an exploded perspective view illustrating a disassembled X-ray imaging apparatus.

As illustrated in FIGS. 1 and 2, an X-ray imaging apparatus 1 may include a guide rail 30, a moving carriage 40, a post frame 50, motors 91, 92, 93, 94, and 95, an X-ray source 70, a connector 75, an X-ray detector 100, a manipulation unit 80, and a workstation 200. The X-ray imaging apparatus 1 may further include an imaging table 10 and an imaging stand 20 in which the X-ray detector 100 may be mounted.

The guide rails 30, the moving carriage 40, the post frame 50, or the like are provided to move the X-ray source 70 toward an object.

The guide rails 30 include a first guide rail 31 and a second guide rail 32 which are installed so as to form a predetermined angle. The first guide rail 31 and the second guide rail 32 may extend in orthogonal directions.

The first guide rail 31 may be installed in a ceiling of a laboratory in which a radiation imaging apparatus is arranged.

The second guide rail 32 is positioned below the first guide rail 31 and is slidably mounted on the first guide rail 31. A roller (not illustrated) that is movable along the first guide rail 31 may be installed in the first guide rail 31. The second guide rail 32 may be connected to this roller (not illustrated) and move along the first guide rail 31.

A first direction D1 is defined as a direction in which the first guide rail 31 extends. A second direction D2 is defined as a direction in which the second guide rail 32 extends. Accordingly, the first direction D1 and the second direction D2 may be orthogonal to each other and parallel to the ceiling of the laboratory.

The moving carriage 40 is arranged below the second guide rail 32 so as to move along the second guide rail 32. A roller (not illustrated) may be installed in the moving carriage 40 so as to move along the second guide rail 32. Accordingly, the moving carriage 40 may move in the first direction D1 with the second guide rail 32, and move in the second direction D2 along the second guide rail 32. The post frame 50 is fixed in the moving carriage 40 and is positioned below the moving carriage 40. The post frame 50 may include a plurality of posts 51, 52, 53, 54, and 55.

The plurality of posts 51, 52, 53, 54, and 55 are connected so as to be folded so that a length of the post frame 50 may increase or decrease in a vertical direction of the laboratory while being fixed to the moving carriage 40. Further, the post frame 50 may have a shape of a telescope frame.

A third direction D3 is defined as a direction in which the length of the post frame 50 increases or decreases. Accordingly, the third direction D3 may be orthogonal to both the first direction D1 and the second direction D2.

The X-ray source 70 is a device configured to radiate X-rays onto the object. The X-ray source 70 may include an X-ray tube 71 configured to generate X-rays, and a collimator 72 configured to guide the generated X-rays toward the object. Here, the object may be a body of human or animal, but the object is not limited thereto. The object may include any object of which an internal structure may be imaged by the X-ray imaging apparatus 1. Also, further details of the X-ray source 70 and the X-ray tube will be described below.

A rotary joint 60 is arranged between the X-ray source 70 and the post frame 50.

The rotary joint 60 enables the X-ray source 70 to be coupled to the post frame 50 and supports a load applied on the X-ray source 70.

The rotary joint 60 may include a first rotary joint 61 connected to a lower post 51 of the post frame 50 and a second rotary joint 62 connected to the X-ray source 70.

The first rotary joint 61 is rotatably provided around a central axis of the post frame 50 that extends in the vertical direction of the laboratory. Accordingly, the first rotary joint 61 may be rotated on a plane perpendicular to the third direction D3. In this case, a rotation direction of the first rotary joint 61 may be newly defined. A newly defined fourth direction D4 is a rotation direction of an axis parallel to the third direction D3.

The second rotary joint 62 is rotatably provided on a plane perpendicular to the ceiling of the laboratory. Accordingly, the second rotary joint 62 may be rotated in a rotation direction of an axis parallel to the first direction D1 or the second direction D2. In this case, the rotation direction of the second rotary joint 62 may be newly defined. A newly defined fifth direction D5 is a rotation direction of an axis that extends in the first direction or the second direction. The X-ray source 70 is connected to the rotary joint 60 and may rotatably move in the fourth direction D4 and the fifth direction D5. In addition, the X-ray source 70 is connected to the post frame 50 by the rotary joint 60 and may linearly move in the first direction D1, the second direction D2, and the third direction D3.

In order to move the X-ray source 70 in the first direction D1 to the fifth direction D5, a motor 90 may be provided. The motor 90 may be a motor that is electrically driven and the motor 90 may include an encoder.

The motor 90 may include a first motor, a second motor, a third motor, a fourth motor, and a fifth motor 91, 92, 93, 94, and 95 corresponding to each direction.

Each of the motors 91, 92, 93, 94, and 95 may be arranged in various positions in consideration of convenience of a design. For example, the first motor 91 that moves the second guide rail 32 in the first direction D1 may be arranged near the first guide rail 31, the second motor 92 that moves the moving carriage 40 in the second direction may be arranged near the second guide rail 32, and the third motor 93 that increases or decreases the length of the post frame 50 in the third direction D3 may be arranged inside the moving carriage 40. In addition, the fourth motor 94 that rotatably moves the X-ray source 70 in the fourth direction D4 may be arranged near the first rotary joint 61, and the fifth motor 95 that rotatably moves the X-ray source 70 in the fifth direction D5 may be arranged near the second rotary joint 62.

Each motor 90 may be connected to a power transmission device (not illustrated) such that the X-ray source 70 linearly or rotatably moves in the first direction D1 to the fifth direction D5. The power transmission device (not illustrated) may include a commonly used belt, pulley, chain, sprocket, shaft or the like.

The manipulation unit 80 configured to provide a user interface is provided in a side of the X-ray source 70. Here, a user may be a medical staff such as a doctor, a radiologist, or a nurse who performs diagnosis on the object using the X-ray imaging apparatus 1, but the user is not limited thereto and may include anyone who uses the X-ray imaging apparatus 1.

Figure 3:
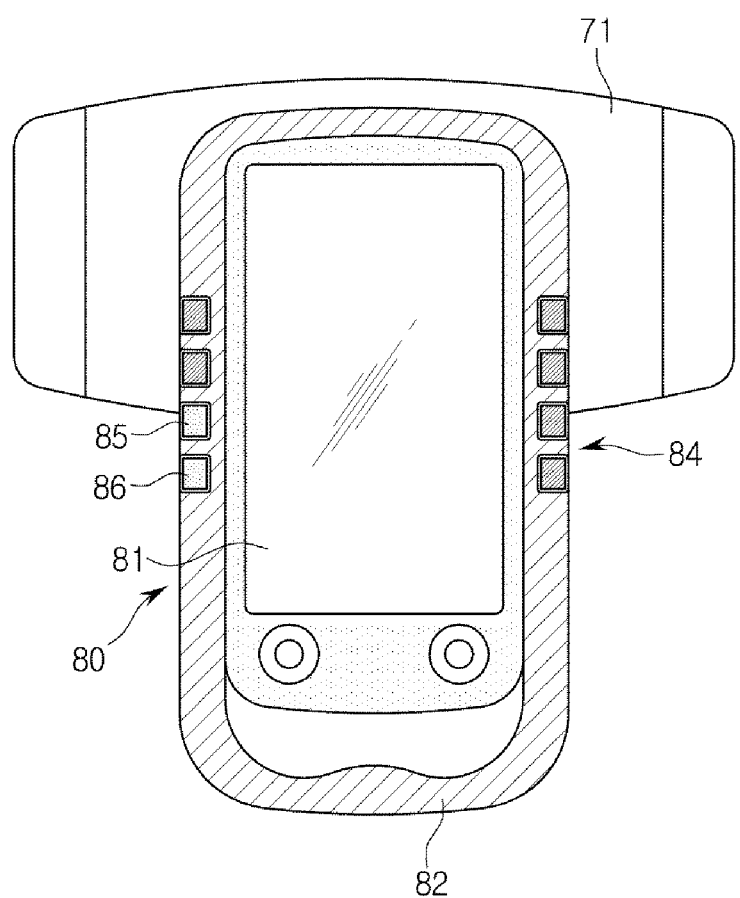
FIG. 3 is a front view illustrating a manipulation unit of an X-ray imaging apparatus.

FIG. 3 is a perspective view of an exemplary manipulation unit of the X-ray imaging apparatus.

As illustrated in FIG. 3, the manipulation unit 80 may include one or more buttons 84 and a display panel 81. The user may input various pieces of information about X-ray imaging or manipulate various devices using a method of pressing the button 84, touching the display panel 81, or the like. One or more buttons 84 may include rotation selection buttons 85, 86 to rotate the X-ray source in the fourth direction D4 or the fifth direction D5. For example, in order to rotate the X-ray source 70 in the fourth direction D4, the user presses the rotation selection button 85, or to rotate the X-ray source 70 in the fifth direction D5, the user presses the rotation selection button 86. Locations of the rotation selection buttons 85, 86 are shown as an example and the locations of the rotation selection buttons are not limited thereto.

For example, the user may input a movement direction and a movement position of the X-ray source 70 through the button 84 or the display panel 81. The motor 90 is automatically driven according to the user's input and linearly moves the X-ray source 70 in the first direction D1, the second direction D2 or the third direction D3, or rotatably moves the X-ray source 70 in the fourth direction D4 or the fifth direction D5, and enables the X-ray source 70 to be positioned in the input movement direction and movement position. This may be defined as an automatic moving mode.

The display panel 81 may include a cathode ray tube (CRT), a digital light processing (DLP) panel, a plasma display panel, a liquid crystal display (LCD) panel, an electro luminescence (EL) panel, an electrophoretic display (EPD) panel, an electrochromic display (ECD) panel, a light emitting diode (LED) panel, an organic light emitting diode (OLED) panel, and the like, but the embodiments are not limited thereto.

The manipulation unit 80 may include a graphic processing unit (GPU), a central processing unit (CPU) implemented as a microprocessor and the like, and various kinds of storage devices. These devices may be provided in an embedded printed circuit board (PCB). The manipulation unit 80 includes the PCB, is provided in a side of the X-ray source 70, and therefore may also be called a "tube head board" or "THU."

Also, the manipulation unit 80 includes a handgrip 82 that may be gripped by the user. That is, the user grips the handgrip 82 of the manipulation unit 80 to apply a force or torque so that the X-ray source 70 is moved linearly in the first direction D1 to the third direction D3, or is rotatably moved in the fourth direction D4 and the fifth direction D5. This may be defined as the automatic moving mode. While a case in which the handgrip 82 is provided below the manipulation unit 80 is exemplified in FIG. 3, the handgrip 82 may also be provided in another position of the manipulation unit 80.

Referring again to FIG. 1, the workstation 200 includes a user interface unit 210 and provides a user interface along with the manipulation unit 80. The user interface unit 210 includes an input unit 211 and a display unit 212, and may receive a user command for X-ray imaging and display various pieces of information about X-ray imaging. For example, the user may set imaging conditions according to an imaging part through the user interface unit 210, or input a movement command of the moving carriage 40 or the X-ray source 70, an X-ray imaging start command, or the like. Also, the user may identify an image obtained by an X-ray imaging process through the user interface unit 210.

The input unit 211 may include a hardware input device such as various buttons, a switch, a keyboard, a mouse, a trackball, various levers, a handle, and a stick for the user's input. As illustrated in FIG. 1, the input unit 211 may be provided above the workstation 200. However, when the input unit 211 is implemented as a foot switch, a foot pedal, and the like, the input unit 211 may also be provided below the workstation 200.

The input unit 211 may include a graphical user interface (GUI) such as a touch pad for the user's input, that is, a software input device. The touch pad is implemented as a touch screen panel (TSP) and may form an interlayer structure with the display unit 212 to be described.

Similar to the display panel 81 of the manipulation unit 80, the display unit 212 may include a cathode ray tube (CRT), a digital light processing (DLP) panel, a plasma display panel, a liquid crystal display (LCD) panel, an electro luminescence (EL) panel, an electrophoretic display (EPD) panel, an electrochromic display (ECD) panel, a light emitting diode (LED) panel, an organic light emitting diode (OLED) panel, and the like, but the embodiments are not limited thereto.

As described above, when the TSP forming the interlayer structure with the touch pad is configured, the display unit 212 may be used as an input device in addition to a display device.

Also, a printed circuit board (PCB) including various processing devices such as a central processing unit (CPU) or a graphic processing unit (GPU) and various kinds of storage devices may be embedded in the workstation 200. Therefore, the workstation 200 may accommodate a main component of the X-ray imaging apparatus 1, for example, the control unit (refer to 250 of FIG. 9), to perform various determinations for operations of the X-ray imaging apparatus 1, or generate various control signals.

A shield B for blocking X-rays is provided between the workstation 200 and a laboratory. Even while X-ray imaging is performed, the user may input information or manipulate a device without being exposed to X-rays through the shield B.

The X-ray detector 100 is a device to detect X-rays transmitted through the object. An incident surface 110 on which X-rays that have transmitted through the object is provided in a front surface or front side of the X-ray detector 100. A detection panel 120 configured to detect incident X-rays, is provided inside the X-ray detector 100. A plurality of pixels (refer to 130 of FIG. 11) responsive to X-rays may be arranged in a matrix form in the detection panel 120. Details thereof will be described below. A handgrip 111 is provided at one side of the X-ray detector 100, for example, a center of an upper part of the X-ray detector 100 and may provide convenience for the user when the X-ray detector 100 is moved or carried.

A detector detecting unit (refer to 140 of FIG. 9) configured to detect a position of the X-ray detector 100, is provided inside or outside the X-ray detector 100. The detector detecting unit 140 may use for example, a magnetic sensor or a tilt sensor. Details thereof will be described below. A battery (refer to 112 of FIG. 7A) configured to supply power to the detection panel 120, the detector detecting unit 140, and the like is provided in a rear surface of the X-ray detector 100 to operate the X-ray detector 100. The battery 112 may include a secondary battery that may be charged and may be detachably provided.

The X-ray detector 100 may be mounted in the imaging table 10 or the imaging stand 20 when X-ray imaging is performed. A mounting unit 300 may be provided in the imaging table 10 and the imaging stand 20 such that the X-ray detector 100 may be mounted. In this case, the mounting unit provided in the imaging table 10 is defined as a table mounting unit 310, and the mounting unit provided in the imaging stand 20 is defined as a stand mounting unit 320.

As illustrated in FIG. 1, the table mounting unit 310 is provided to move in a longitudinal direction of a support 22 and rotate in a rotation direction of an axis perpendicular to the longitudinal direction of the support 22. Also, the stand mounting unit 320 may be provided to move in a longitudinal direction of the imaging table 10. In this case, the longitudinal direction of the support 22 is defined as a sixth direction D6, the rotation direction of an axis perpendicular to the sixth direction D6 is defined as a seventh direction D7, and the longitudinal direction of the imaging table 10 is defined as an eighth direction D8.

Figure 4A:
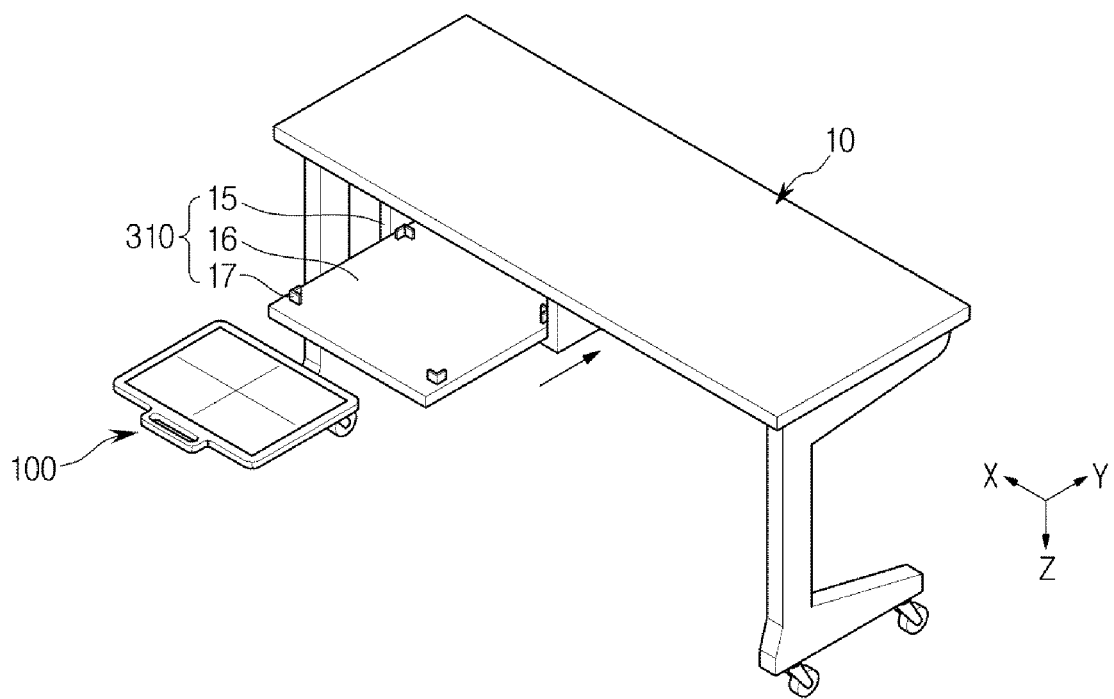
FIGS. 4A and 4B are diagrams illustrating an exemplary X-ray detector mounted in an imaging table.
Figure 4B:
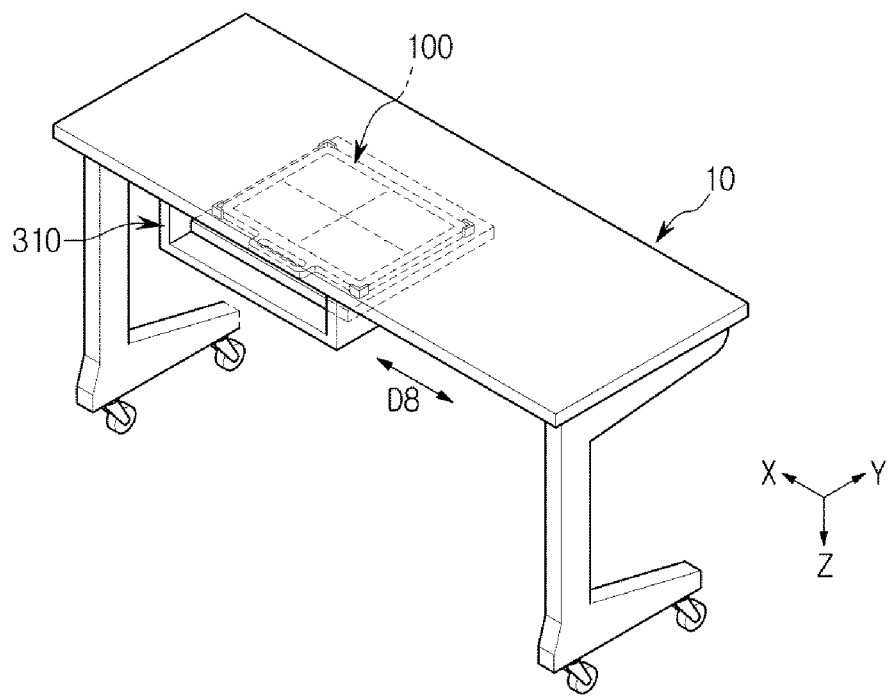

FIGS. 4A and 4B ("FIG. 4") are diagrams illustrating an exemplary X-ray detector mounted in the imaging table.

As illustrated in FIG. 4, the table mounting unit 310 may include a housing 15, an accommodating plate 16 accommodating the X-ray detector 100, and a fixing unit 17 configured to fix the accommodated X-ray detector 100. The accommodating plate 16 may be provided in parallel with a bottom surface, that is, a plane formed by an x axis and a y axis, and may be removed from the housing 15 or inserted into the housing 15 through a guide rail (not illustrated), a guide groove (not illustrated), and the like. The X-ray detector 100 is accommodated in the accommodating plate 16 while being fixed by the fixing unit 17 and may be mounted in the table mounting unit 310 in parallel with the bottom surface when the accommodating plate 16 is inserted.

The table mounting unit 310 in which the X-ray detector 100 is mounted moves in the eighth direction D8 and may allow the entire object or a specific part of the object lying on the imaging table 10 to be imaged.

Figure 5A:
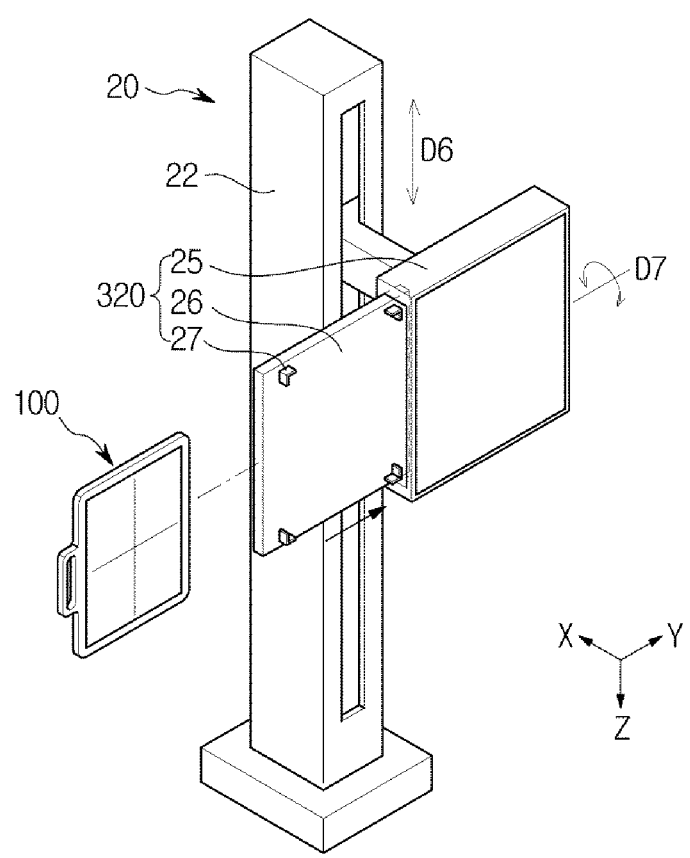
FIGS. 5A and 5B are diagrams illustrating an example of an X-ray detector mounted in an imaging stand.
Figure 5B:
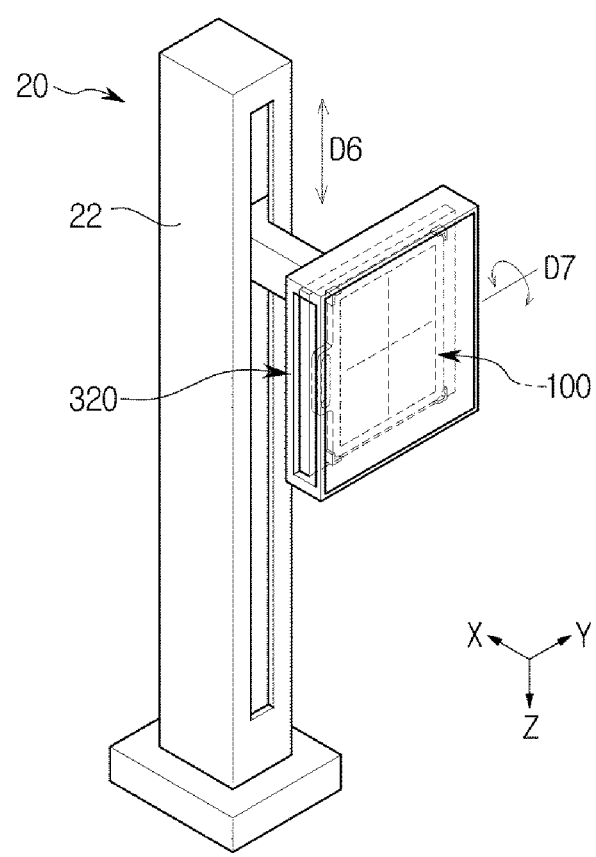
Figure 5C:
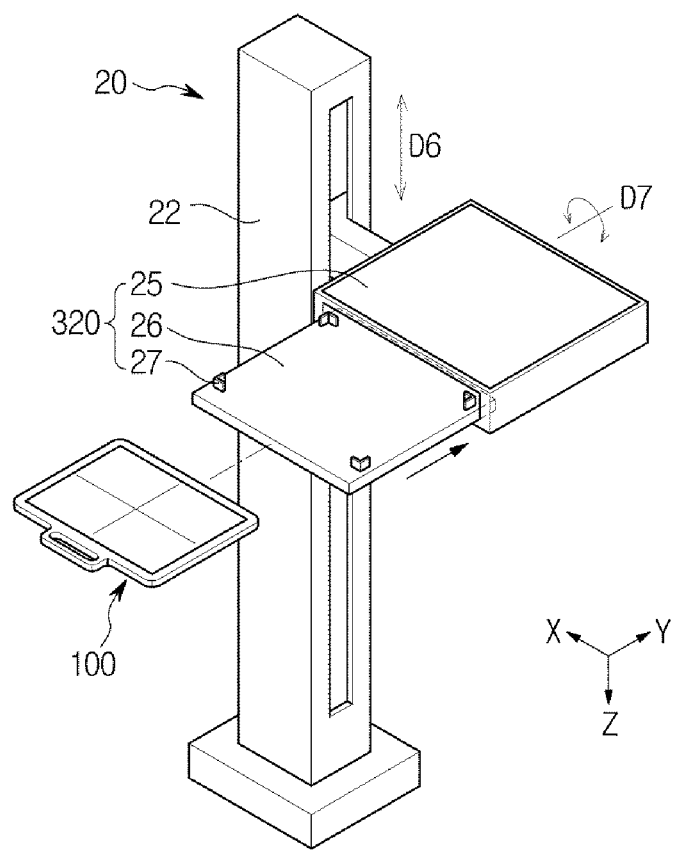
FIGS. 5C and 5D are diagrams illustrating another example of the X-ray detector mounted in the imaging stand.
Figure 5D:
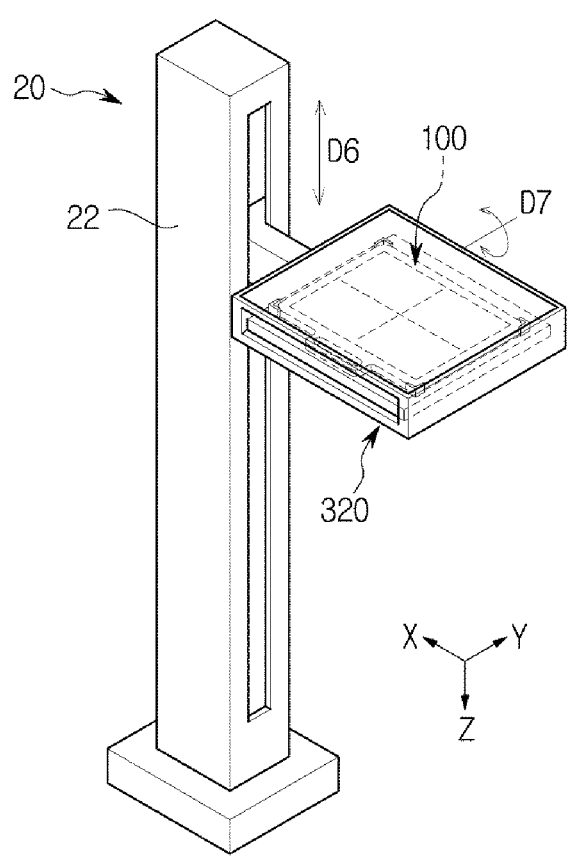

FIGS. 5A and 5B are diagrams illustrating an example of the X-ray detector mounted in the imaging stand. FIGS. 5C and 5D are diagrams illustrating another example of the X-ray detector mounted in the imaging stand.

As illustrated in FIGS. 5A 5D, similar to the table mounting unit 310, the stand mounting unit 320 may include a housing 25, an accommodating plate 26 accommodating the X-ray detector 100, and a fixing unit 27 configured to fix the accommodated X-ray detector 100. Also, the accommodating plate 26 may be removed from the housing 25 or inserted into the housing 25 through a guide rail (not illustrated), a guide groove (not illustrated), and the like.

As described above, the stand mounting unit 320 may rotate in the seventh direction D7. Therefore, as illustrated in FIGS. 5A and 5B, the accommodating plate 26 may be removed or inserted perpendicular to the bottom surface, that is, in parallel with a plane formed by an x axis and a z axis, and as illustrated in FIGS. 5C and 5D, may be removed or inserted in parallel with the bottom surface, that is, in parallel with a plane formed by an x axis and a y axis.

The X-ray detector 100 is accommodated in the accommodating plate 26 while being fixed by the fixing unit 27. According to a direction in which the accommodating plate 26 is removed or inserted, the X-ray detector 100 may be mounted in the stand mounting unit 320 perpendicular to the bottom surface as on the bottom in FIGS. 5A and 5B. Also, the X-ray detector 100 may be mounted in the stand mounting unit 320 in parallel with the bottom surface as on the bottom in FIGS. 5C and 5D.

The stand mounting unit 320 in which the X-ray detector 100 is mounted moves in the sixth direction D6, and may allow the entire object or a specific part of the object standing on the imaging stand 20 to be imaged.

The X-ray detector 100 may be portably provided without being mounted in the imaging table 10 or the imaging stand 20.

Figure 6:
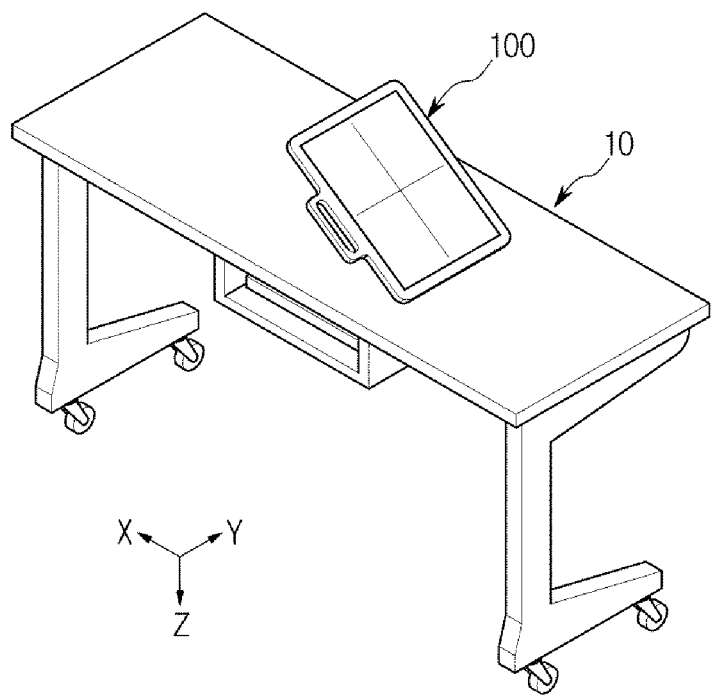
FIG. 6 is a diagram illustrating an example in which a portable X-ray detector is provided.

FIG. 6 is a diagram illustrating an example in which the X-ray detector is portably provided.

As illustrated in FIG. 6, the X-ray detector 100 is not fixedly mounted in the table mounting unit 310 or the stand mounting unit 320, and may be provided to freely move outside the imaging table 10 and the imaging stand 20. When the X-ray detector 100 is portably provided, the object may be imaged in various positions, various directions, or various angles, and customized imaging corresponding to the object's state may be performed.

Figure 7A:
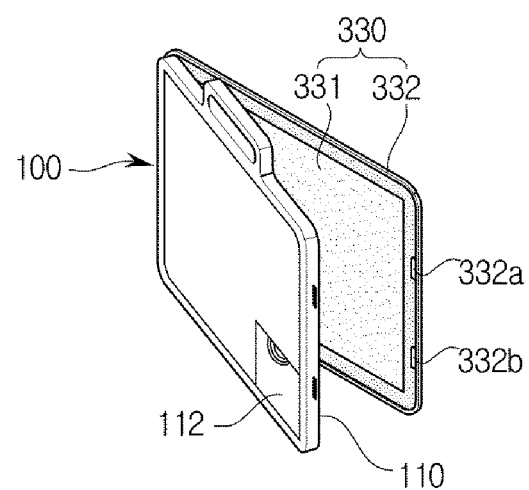
FIGS. 7A and 7B are diagrams illustrating another example in which the X-ray detector is portably provided.
Figure 7B:
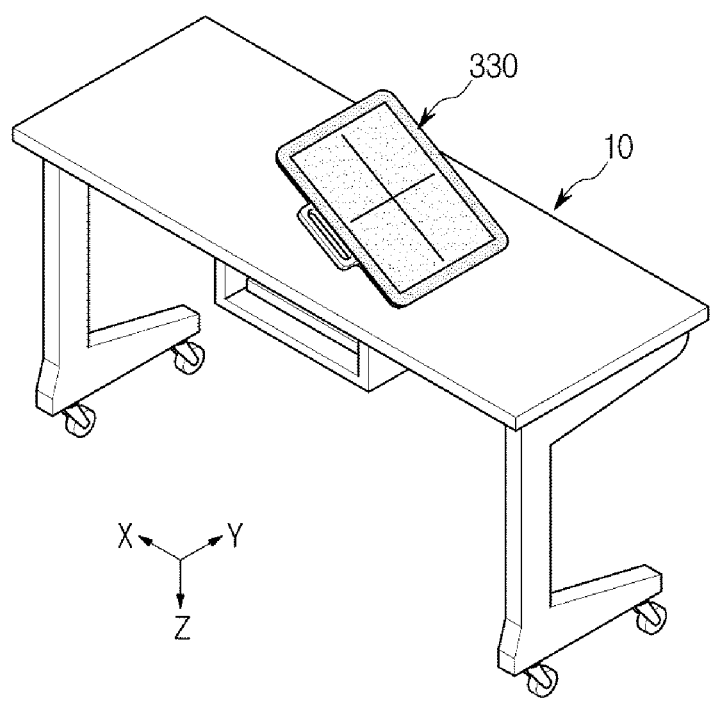

FIGS. 7A and 7B are diagrams illustrating another example in which the X-ray detector is portably provided.

As illustrated in FIGS. 7A and 7B, the X-ray detector 100 may be mounted in a portable mounting unit 330. The portable mounting unit 330 may include a grid 331 configured to reduce an amount of scattering rays arriving at the X-ray detector 100 and a frame 332 forming a circumference of the grid 331.

The grid 331 may be formed by mixing a material having a high X-ray absorption rate and a material having a low X-ray absorption rate. The grid 331 includes at least one thin plate having a high X-ray absorption rate, and may be formed in a form in which a material having a low X-ray absorption rate is provided between thin plates. In the thin plate, an absorption pattern layer may be made of lead, bismuth, gold, barium, tungsten, platinum, mercury, indium, thallium, palladium, tin, zinc or alloys thereof, but the embodiments are not limited thereto. The material having a low X-ray absorption rate may be made of any of plastic, a polymer, a ceramic, graphite, and a carbon fiber, but the embodiments are not limited thereto.

Also, the grid 331 may be implemented as a focused grid in which thin plates are arranged toward a focus in a predetermined angle, a parallel grid in which thin plates are arranged in parallel, or a crossed grid in which a plurality of parallel grids are overlapped, but the embodiments are not limited thereto.

At least one protrusion 332a or 332b may be formed in the frame 332. The X-ray detector 100 may be combined with the portable mounting unit 300 being fitted to the protrusions 332a and 332b, but the embodiments are not limited thereto. As long as the X-ray detector 100 may be combined with the portable mounting unit 300, the portable mounting unit 300 may have a structure other than a structure forming the protrusion, and a method other than the fitting may also be applied.

The portable mounting unit 300 combined with the X-ray detector 100 forms a cover of the incident surface 110. The grid 331 is provided in a front surface of the incident surface 110, and may reduce an amount of X-ray scattering incident on the X-ray detector 100 or prevent scattering of X-rays.

As illustrated in FIG. 7B, the X-ray detector 100 moves while being mounted in the portable mounting unit 300 and may be portably used. The X-ray detector 100 moves while being mounted in the portable mounting unit 300 and allows the object to be imaged in various positions, directions or angles.

As described above, the X-ray detector 100 may be mounted in the table mounting unit 310 or may be mounted in the stand mounting unit 320. Also, the X-ray detector 100 may be portably provided without being mounted in the table mounting unit 310 or the stand mounting unit 320, or may be portably provided while being mounted in the portable mounting unit 330. In this manner, according to a mounting position and a mounting state of the X-ray detector 100, and the like, a table type, a stand type, and a portable type may be defined. The X-ray detector 100 mounted in the table mounting unit 310 is defined as a table type X-ray detector, the X-ray detector 100 mounted in the stand mounting unit 320 is defined as a stand type X-ray detector, and the X-ray detector 100 that is portably provided without being mounted in the table mounting unit 310 or the stand mounting unit 320 or that is portably provided while being mounted in the portable mounting unit 330 is defined as a portable type X-ray detector, respectively.

Also, hereinbelow, the expressions "mounted in the table mounting unit 310," "implemented in a table type," and "provided in a table type" are the same. Similarly, the expressions "mounted in the stand mounting unit 320," "implemented in a stand type," and "provided in a stand type" are the same. The expressions "is portably provided," "implemented in a portable type," and "is provided in a portable type" are the same.

The X-ray detector 100 may be provided alone. The single X-ray detector 100 may be implemented in the table type, the stand type, or the portable type. Also, a plurality of X-ray detectors 100 may be provided. The plurality of X-ray detectors 100 may also be implemented in different types. All of the plurality of X-ray detectors 100 or some of the plurality of X-ray detectors 100 may also be implemented in the same type.

Figure 8A:
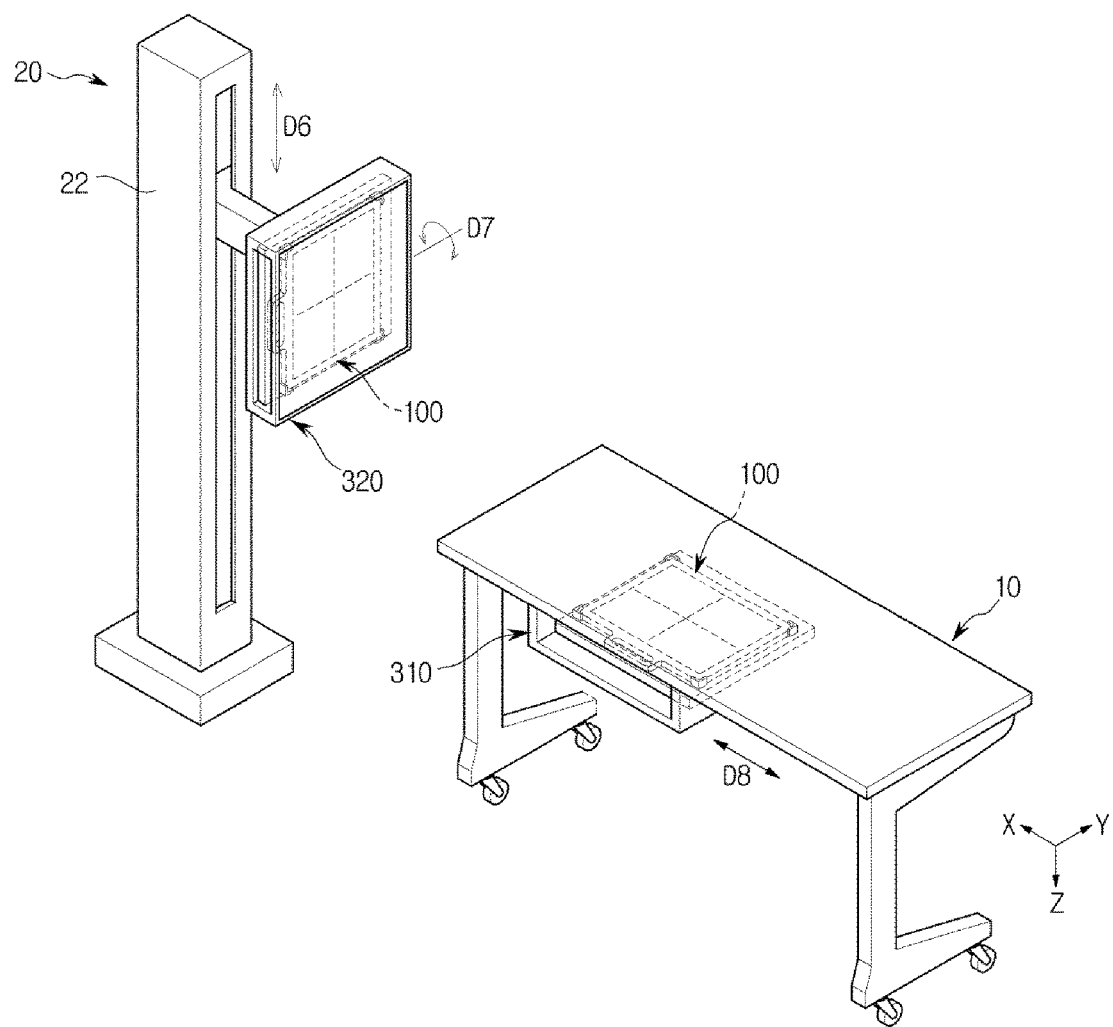
FIG. 8A is a diagram illustrating an example in which a plurality of X-ray detectors is provided.
Figure 8B:
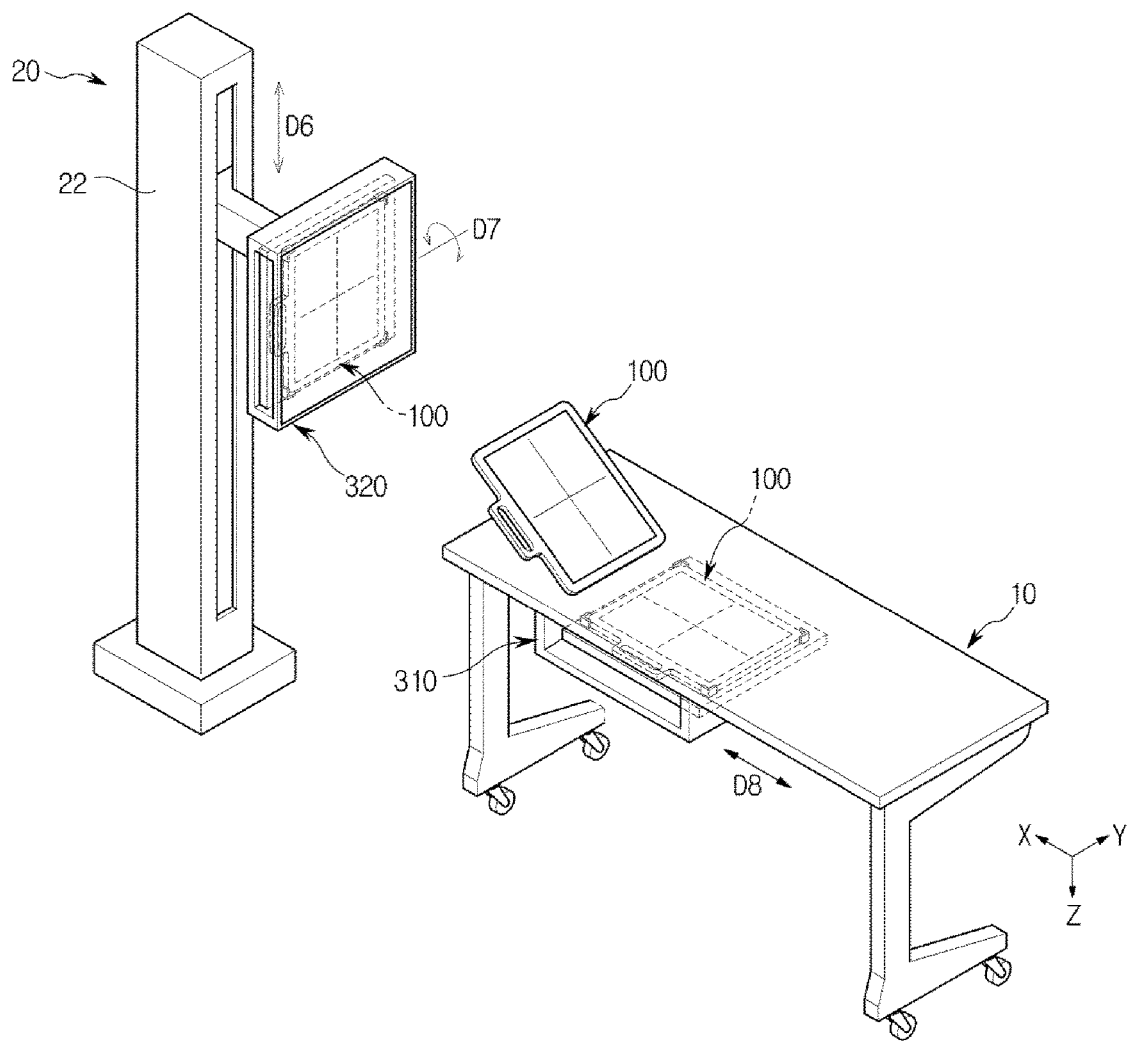
FIG. 8B is a diagram illustrating another example in which the plurality of X-ray detectors is provided.

FIG. 8A is a diagram illustrating an example in which the plurality of X-ray detectors are provided. FIG. 8B is a diagram illustrating another example in which the plurality of X-ray detectors are provided.

As illustrated in FIG. 8A, the plurality of X-ray detectors 100 are provided. The plurality of X-ray detectors 100 may include the table type X-ray detector mounted in the table mounting unit 310 and the stand type X-ray detector mounted in the stand mounting unit 320. The plurality of X-ray detectors 100 may include at least two of the stand type X-ray detector, the table type X-ray detector, and the portable type X-ray detector. For example, the plurality of X-ray detectors may include the stand type X-ray detector and the portable type X-ray detector, or may include the table type X-ray detector and the portable type X-ray detector. In addition, as illustrated in FIG. 8B, the plurality of X-ray detectors 100 may include the table type X-ray detector, the stand type X-ray detector, and the portable type X-ray detector.

In order to perform X-ray imaging at a position desired by the user, the X-ray detector 100 should be provided at a corresponding position and X-ray detection should be performed by the X-ray detector 100 at the corresponding position. That is, the ID of the X-ray detector 100 should be set according to the corresponding position. For example, in order to image the object lying on the imaging table 10, the table type X-ray detector 100 should be provided and the ID of the X-ray detector 100 should be set for a table.

Also, in order to perform X-ray imaging, it is necessary to determine whether the X-ray detector 100 is mounted and it is necessary to determine an X-ray detector 100 and a mounting position thereof. That is, it is necessary to determine the mounting position and the ID of the X-ray detector 100. For example, in order to image the object lying on the imaging table 10, it is necessary to determine whether the X-ray detector 100 is mounted in the table mounting unit 310. Also, it is necessary to identify the ID of the X-ray detector 100 mounted in the table mounting unit 310 and determine whether the ID of the X-ray detector 100 is set for a table.

Accordingly, hereinbelow, with reference to a given control block diagram, components of the X-ray imaging apparatus 1 capable of determining an X-ray detector 100 and a mounting position thereof, and functions of the components will be described in detail.

Figure 9:
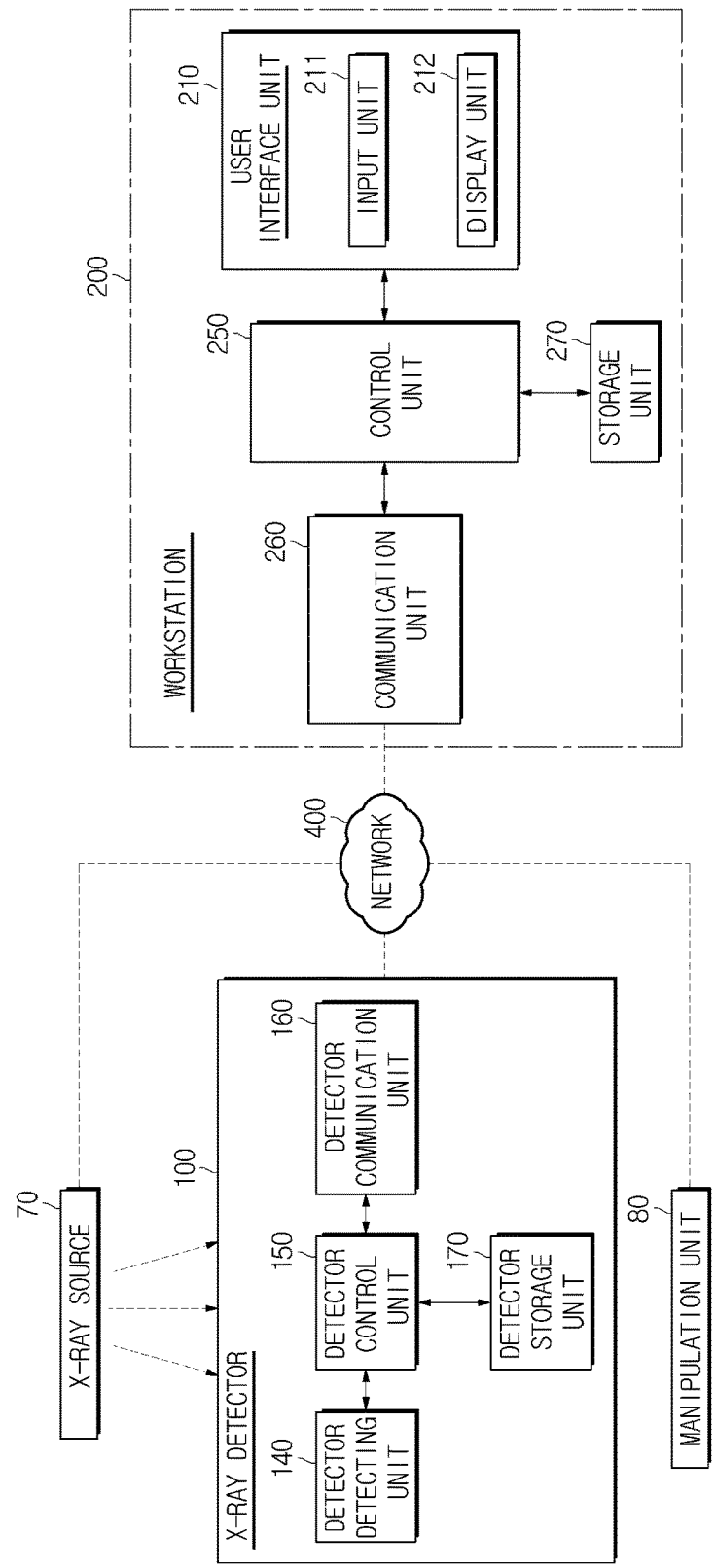
FIG. 9 is a control block diagram of an X-ray imaging apparatus according to an embodiment.

FIG. 9 is a control block diagram of an X-ray imaging apparatus according to an embodiment.

As illustrated in FIG. 9, the X-ray imaging apparatus 1 may include the workstation 200, the X-ray source 70, the X-ray detector 100, and the manipulation unit 80. The X-ray source 70, the X-ray detector 100, and the manipulation unit 80 may be connected to the workstation 200 via a wired and/or wireless network 400. The workstation 200 includes the user interface unit 210, a communication unit 260, a control unit 250, and a storage unit 270. The X-ray detector

100 may include the detector detecting unit 140, a detector control unit 150, a detector communication unit 160, and a detector storage unit 170.

Figure 10:
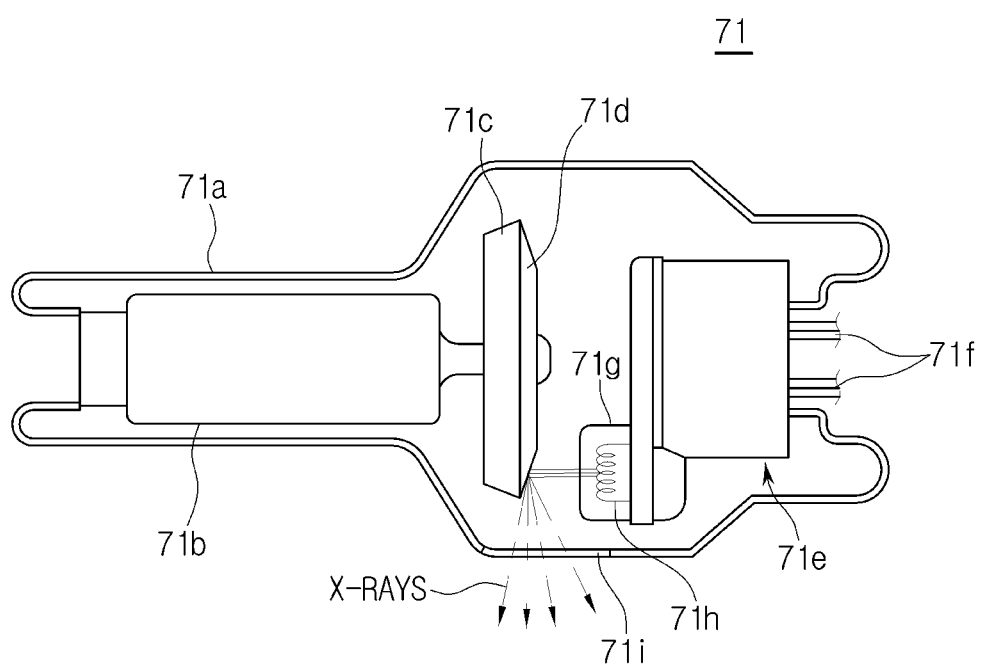
FIG. 10 is a cross-sectional view of an internal structure of an exemplary X-ray tube.

The X-ray source 70 is a device that generates X-rays and radiates the generated X-rays onto the object, and may include the X-ray tube 71 in order to generate X-rays, as illustrated in FIG. 10. FIG. 10 is a cross-sectional view of an internal structure of an exemplary X-ray tube.

The X-ray tube 71 may be implemented as a diode including an anode 71c and a cathode 71e. A tube body may be a glass tube 71a made of, for example, silica hard glass.

The cathode 71e includes a filament 71h and a focusing electrode 71g configured to focus electrons. The focusing electrode 71g is also referred to as a focusing cup. An inside of the glass tube 71a is maintained in a high vacuum state of about 10 mmHg, the filament 71h of the cathode is heated to a high temperature, and thermoelectrons are generated. As an example of the filament 71h, a tungsten filament may be used. Current may be applied to an electrical conductor 71f connected to the filament and heat the filament 71h. However, the embodiments are not limited to employing the filament 71h in the cathode 71e, but it is also possible to use a carbon nano-tube capable of being driven in a high-speed pulse as the cathode.

The anode 71c is mainly made of copper, a target material 71d is coated or arranged on a side facing the cathode 71e. A high-resistance material such as Cr, Fe, Co, Ni, W, and Mo may be used as the target material. As a melting point of the target material increases, a focal spot size decreases.

When high voltage is applied between the cathode 71e and the anode 71c, thermoelectrons are accelerated and collide with the target material 71d of the anode, and X-rays are generated. The generated X-rays are radiated to the outside through a window 71i and a beryllium (Be) film may be used as a material of the window.

The target material 71d may be rotated by a rotor 71b. When the target material 71d is rotated, a heat accumulation rate per unit area may be about ten times or more that of a fixed state of the target material 71d and the focal spot size decreases.

Voltage applied between the cathode 71e and the anode 71c of the X-ray tube 71 is referred to as tube voltage, and a level thereof may be indicated as peak kilovoltage (kvp). As the tube voltage increases, a speed of the thermoelectrons increases. As a result, energy (photon energy) generated when the X-rays collide with the target material increases. Current flowing in the X-ray tube 71 is referred to as tube current and may be indicated as an average mA. As the tube current increases, an X-ray dose (the number of X-ray photons) increases. That is, energy of X-rays may be controlled by the tube voltage and the X-ray dose may be controlled by the tube current and an X-ray exposure time.

The X-ray detector 100 is a device that detects the X-rays that have been radiated from the X-ray source 70 and transmitted through the object. This X-ray detection may be performed in the detection panel 120 inside the X-ray detector 100. In addition, the detection panel 120 converts the detected X-rays into an electrical signal and an X-ray image of an inside of the object is obtained.

The detection panel 120 may be classified according to a material configuration method, a method of converting detected X-rays into an electrical signal, and a method of obtaining an electrical signal.

First, the detection panel 120 may be classified as a single element configuration or a mixed element configuration according to the material configuration method.

When the single element configuration is used, a part in which the X-rays are detected and an electrical signal is generated and a part in which the electrical signal is read and processed are made of a single element semiconductor or are manufactured in a single process. For example, a complementary metal oxide semiconductor (CMOS) or a charge coupled device (CCD) serving as a light receiving element may be used.

When the mixed element configuration is used, a part in which the X-rays are detected and an electrical signal is generated and a part in which the electrical signal is read and processed are made of different elements or are manufactured in different processes. For example, there are cases in which X-rays are detected using a light receiving element such as a photo diode, a CCD, and CdZnTe and an electrical signal is read and processed using a CMOS read out integrated circuit (ROIC), cases in which X-rays are detected using a strip detecting unit and an electrical signal is read and processed using a CMOS ROIC, and cases in which an a-Si or a-Se flat panel system is used.

The detection panel 120 is classified as performing a direct converting method or an indirect converting method according to the method of converting X-rays into an electrical signal.

In the direct converting method, when X-rays are radiated, electron-hole pairs are temporarily generated inside the light receiving element, and electrons move to an anode and holes move to a cathode due to an electric field applied to both ends of the light receiving element. The detection panel 120 converts this movement into an electrical signal. In the direct converting method, a-Se, CdZnTe, HgI2, PbI2, or the like is a material used as the light receiving element In the indirect converting method, when X-rays radiated from the X-ray source 70 react with a scintillator and photons having a wavelength of a visible light range are emitted, the light receiving element detects the emitted photons and converts the photons into an electrical signal. In the indirect converting method, a-Si or the like is a material used as the light receiving element and a thin-film GADOX scintillator, or a micro columnar or needle-shaped CSI (TI) scintillator is used as the scintillator.

In addition, a method of obtaining an electrical signal in the detection panel 120 is classified as a charge integration mode in which electric charges are stored for a predetermined time and a signal is obtained therefrom or a photon counting mode in which photons are counted whenever a signal is generated by a single X-ray photon.

The detection panel 120 may apply any of the above methods. However, for convenience of description, application of the direct converting method in which an electrical signal is directly obtained from X-rays, a hybrid method in which a sensor chip to detect X-rays and a readout circuit chip are combined, and a photon counting method will be described below.

Figure 11:
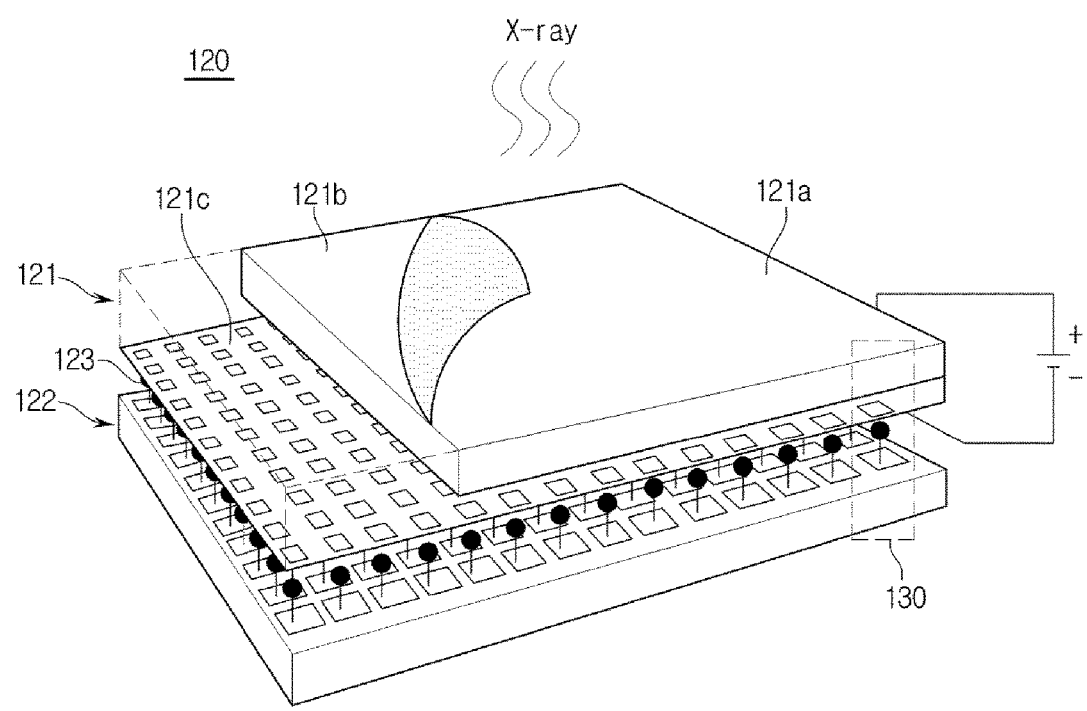
FIG. 11 is a schematic diagram schematically illustrating a structure of a detection panel.

The detection panel 120 may have a 2D array structure including a plurality of pixels 130 as illustrated in FIG. 11. FIG. 11 is a schematic diagram illustrating a structure of the detection panel.

As illustrated in FIG. 11, the detection panel 120 may include a receiving element 121 configured to detect X-rays and generate an electrical signal, and a readout circuit 122 configured to read out the generated electrical signal.

In order to secure a high resolution, a rapid response time, and a high dynamic area with low energy and a small dose, a single crystal semiconductor material may be used as the receiving element 121. In this case, the single crystal semiconductor material to be used may include Ge, CdTe, CdZnTe, GaAs, or the like.

The receiving element 121 may be formed as a PIN photodiode in which a p-type semiconductor substrate 121c having a 2D array structure is bonded to a bottom of a high resistance n-type semiconductor substrate 121b.

The readout circuit 122 using a CMOS process forms a 2D array structure, and may be bonded to the p-type semiconductor substrate 121c of the receiving element 121 for each pixel 150. In this case, as a bonding method, a flip-chip bonding method in which a bump 123 such as solder (PbSn) or indium (In) is formed, reflowed, heated, and compressed may be used.

Figure 12:
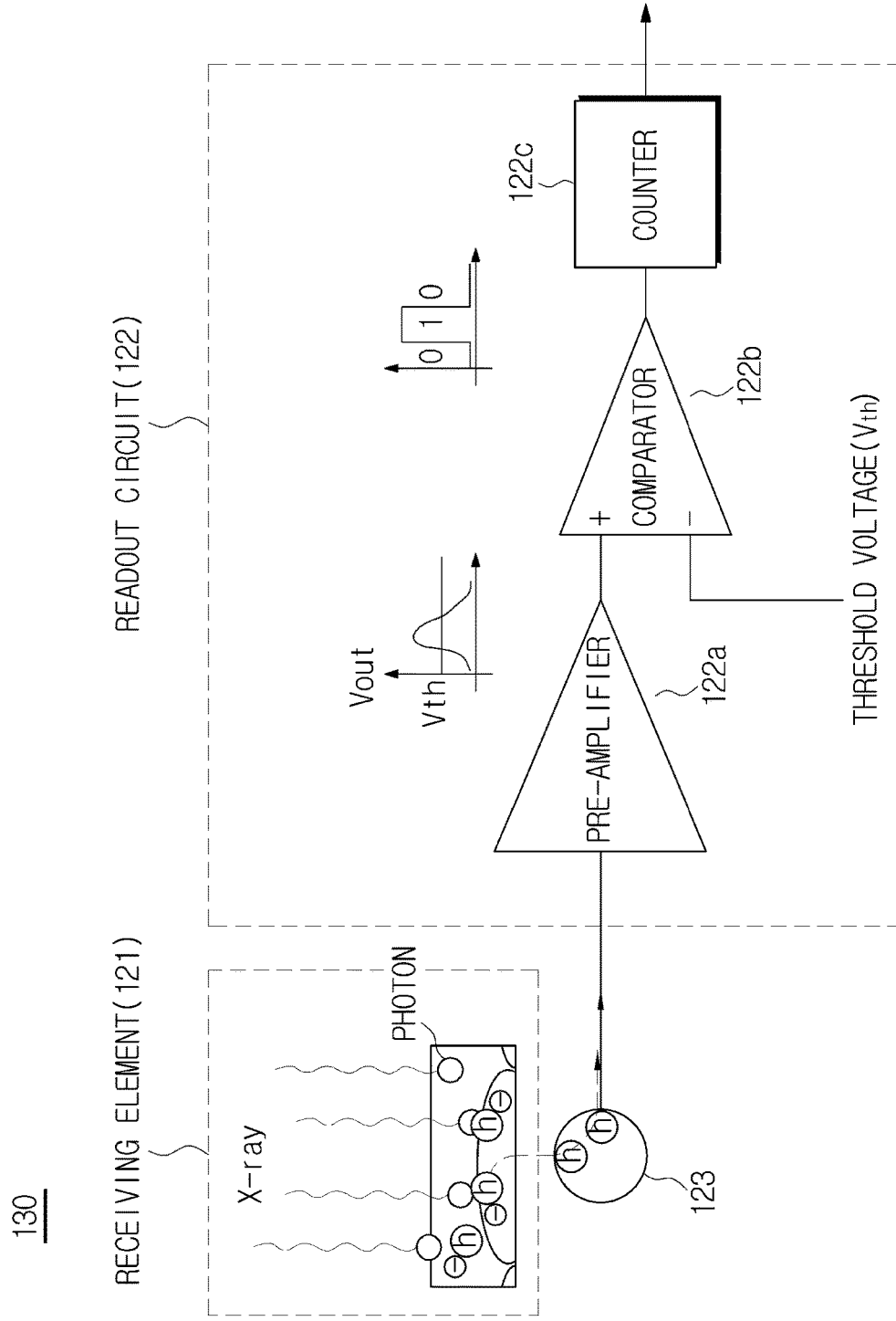
FIG. 12 is a circuit diagram schematically illustrating a single pixel of the detection panel.

FIG. 12 is a circuit diagram schematically illustrating a single pixel area.

As illustrated in FIG. 12, when photons of X-rays are incident on the receiving element 121, electrons in a valance band receive energy of photons, cross over a band gap energy difference, and are excited into a conduction band. Therefore, electron-hole pairs are generated in a depletion region in which there are no electrons or holes.

When each metal electrode is formed in a p-type layer and an n-type substrate of the receiving element 121 and reverse bias is applied, among electron-hole pairs generated in the depletion region, electrons move to an n-type region and holes move to a p-type region. The holes that move to the p-type region are input to the readout circuit 122 through bump bonding 123.

Electric charges input to the readout circuit 122 are delivered to a pre-amplifier 122a and a voltage signal corresponding thereto is output.

The voltage signal output from the pre-amplifier 122a is delivered to a comparator 122b. The comparator compares any threshold voltage that can be controlled from the outside and an input voltage signal, and outputs a pulse signal of "1" or "0" based on a comparison result. That is, the comparator outputs a signal of "1" when input voltage is greater than threshold voltage, and outputs a signal of "0" when the input voltage is smaller than threshold voltage. A counter 122c counts the number of times "1" is output and outputs data in a digital form.

Referring again to FIG. 9, the X-ray detector 100 may include the detector detecting unit 140, the detector control unit 150, the detector communication unit 160, and the detector storage unit 170.

The detector control unit 150 controls overall operations of the X-ray detector 100. The detector control unit 150 may control each component of the X-ray detector 100, that is, the detector detecting unit 140, the detector communication unit 160, the detector storage unit 170, and the like. The detector control unit 150 may be various types of processors including at least one chip having an integrated circuit formed therein.

The detector detecting unit 140 may include at least one sensor detecting a position of the X-ray detector 100. The detector detecting unit 140 may be provided in a rear surface or a side surface of the X-ray detector 100, or may also be provided inside the X-ray detector 100. That is, a position of the detector detecting unit 140 is not limited, as long as detection of X-rays is not affected.

The detector detecting unit 140 may use a magnetic sensor or a tilt sensor, but the embodiments are not limited thereto. However, different types of sensors may also be used as long as the position of the X-ray detector 100 may be detected. For convenience of description, hereinafter, the detector detecting unit 140 including the magnetic sensor or the tilt sensor will be exemplified and described.

The magnetic sensor is a sensor configured to detect a magnetic field or a magnetic intensity, a direction thereof, a strength thereof, and the like, and may be classified as a linear magnetic sensor or a nonlinear magnetic sensor. The linear magnetic sensor (hereinafter referred to as "M") refers to a magnetic sensor configured to linearly output a value corresponding to a magnetic field strength, such as a hall sensor. The nonlinear magnetic sensor (hereinafter referred to as "H") refers to a magnetic sensor configured to output on or off according to whether a magnetic field strength is equal to or greater than a threshold value such as a hall integrated circuit (hall IC). Also, the magnetic field strength may be defined as a sum of sizes of magnetic fields in three mutually orthogonal directions with respect to each magnetic sensor. Accordingly, when a vector of the magnetic field detected by the magnetic sensor forms coordinates of (x, y, z)=(V1, V2, V3) with respect to mutually orthogonal x axis, y axis, and z axis, the magnetic field strength becomes |V1|+|V2|+|V3|.

The tilt sensor (hereinafter referred to as "G") is a sensor configured to detect a degree of a tilt with respect to a gravity direction, and may include an acceleration sensor configured to detect a tilt by measuring a degree of inclination with respect to a gravity acceleration, a gyro sensor configured to detect a tilt by measuring a rotation direction or a rotation angle according to movement, and the like, but the embodiments are not limited thereto.

FIGS. 13A, 13B, 13C, 13D and 13E ("FIG. 13) are diagrams illustrating an example of a detector detecting unit including a linear magnetic sensor. FIG. 14 is a diagram illustrating a magnetic field detected by the linear magnetic sensor of FIG. 13.

Figure 13A:
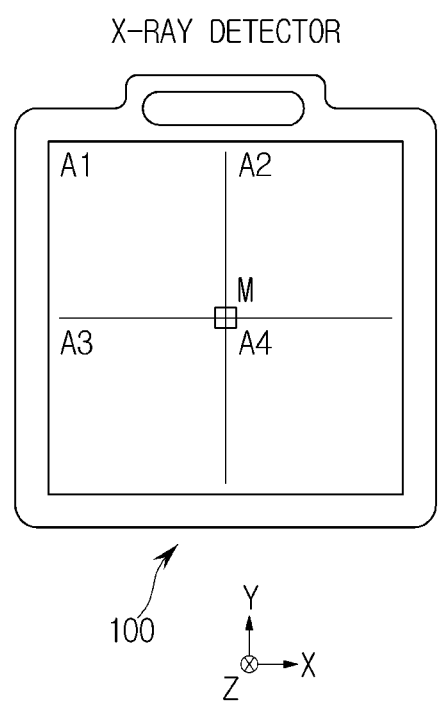
FIGS. 13 A, 13B, 13C, 13D and 13E ("FIG. 13") are diagrams illustrating an example of a detector detecting unit including a linear magnetic sensor.

As illustrated in, FIG. 13A, the X-ray detector 100 may include the detector detecting unit 140 having the single linear magnetic sensor M. While the single X-ray detector 100 is exemplified in FIG. 13, the plurality of X-ray detectors 100 may be provided as described above. When the plurality of X-ray detectors 100 are provided, all of the X-ray detectors 100 have the single linear magnetic sensor M at the same positions.

The X-ray detector 100 may be divided into four virtual regions, that is, A1, A2, A3, and A4, with respect to the single linear magnetic sensor M. A1, A2, A3, and A4 may have the same shape and size or different shapes and sizes. Each of the table mounting unit 310 and the stand mounting unit 320 may be divided into four virtual regions to correspond to shapes and sizes of A1, A2, A3, and A4. Here, the divided regions of the table mounting unit 310 are defined as B1, B2, B3, and B4, and the divided regions of the stand mounting unit 320 are defined as C1, C2, C3, and C4.

A magnet may be mounted in the table mounting unit 310 and the stand mounting unit 320. In the table mounting unit 310, the magnet may be mounted in, for example, an inside of the housing 15, and a front surface or a rear surface of the accommodating plate 16. Similarly, in the stand mounting unit 320, the magnet may be mounted in an inside of the housing 25, and a front surface or a rear surface of the accommodating plate 26.

Figure 13C:
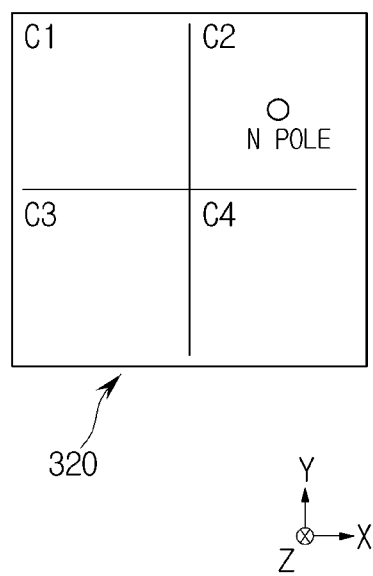

The magnet of the table mounting unit 310 and the magnet of the stand mounting unit 320 may be mounted in positions that correspond or do not correspond to each other. The magnet of the table mounting unit 310 and the magnet of the stand mounting unit 320 may be aligned by different polarities. For example, as illustrated in FIGS. 13B and 13C, the magnet of the table mounting unit 310 may be mounted in the region B2, and the magnet of the stand mounting unit 320 may be mounted in the region C2. Also, the magnet of the table mounting unit 310 may be aligned by an S pole and the magnet of the stand mounting unit 320 may be aligned by an N pole.

Figure 13D:
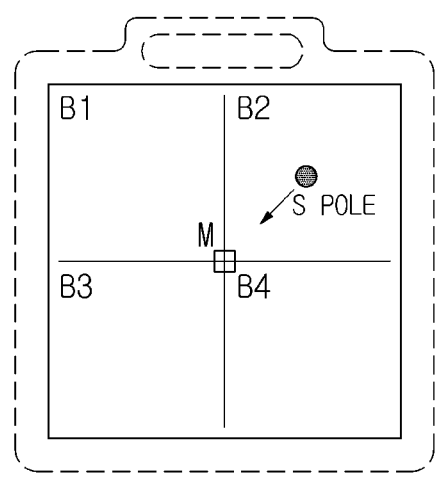
Figure 13E:
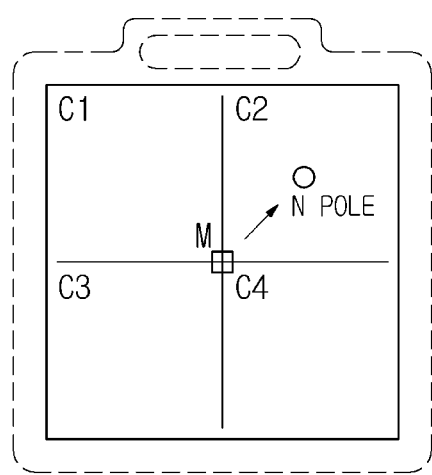

Accordingly, the linear magnetic sensor M detects a different magnetic field direction according to whether the X-ray detector 100 is mounted in the table mounting unit 310 or in the stand mounting unit 320. When the X-ray detector 100 is mounted in the table mounting unit 310, that is, when the X-ray detector 100 is implemented in a table type, the linear magnetic sensor M detects magnetic field lines output from the top right, as illustrated in FIG. 13D. On the other hand, when the X-ray detector 100 is mounted in the stand mounting unit 320, that is, when the X-ray detector 100 is implemented in a stand type, the linear magnetic sensor M detects magnetic field lines entering at the top right, as illustrated in FIG. 13E.

As illustrated in FIG. 14, when a magnetic field direction is expressed as a coordinate format of (x, y, z), if the X-ray detector 100 is implemented in a table type, the linear magnetic sensor M detects a magnetic field direction of (x, y, z)=(+, +, +), and if the X-ray detector 100 is implemented in a stand type, the linear magnetic sensor M detects a magnetic field direction of (x, y, z)=(−, −, +). That is, the linear magnetic sensor M detects different magnetic fields in an x axis direction and a y axis direction according to a mounting position.

Similarly, when the plurality of X-ray detectors 100 exemplified in FIG. 13 are provided, the linear magnetic sensor M of the X-ray detector 100 implemented in a table type and the linear magnetic sensor M of the X-ray detector 100 implemented in a stand type detect a different magnetic field direction.

The control unit 250 to be described may determine a mounting position of the X-ray detector 100 using a magnetic field direction detected by the linear magnetic sensor M in this manner. When the X-ray detector 100 is mounted, a sensor value of the linear magnetic sensor M may be stored in the detector storage unit 170 temporarily or non-temporarily.

FIGS. 15A, 15B, 15C, 15D, 15E, 15F and 15G ("FIG. 15") are diagrams illustrating another example of the detector detecting unit including the linear magnetic sensor. FIG. 16 is a diagram illustrating a magnetic field detected by the linear magnetic sensor of FIG. 14. When other embodiments of the detector detecting unit 140 including the embodiment illustrated in FIG. 15 are described, content that is the same as or similar to that of the above-described embodiment will not be repeated.

As illustrated in FIG. 15, the X-ray imaging apparatus 1 may further include the portable mounting unit 330 in addition to the table mounting unit 310 and the stand mounting unit 320.

As the same as in FIG. 13A, the detector detecting unit 140 of the X-ray detector 100 may include the single linear magnetic sensor M. When the plurality of X-ray detectors 100 are provided, all of the X-ray detectors 100 include the single linear magnetic sensor M at the same positions.

Also, the four virtual regions A1, A2, A3, and A4 of the X-ray detector 100, and the four regions B1, B2, B3, and B4 of the table mounting unit 310 and the four regions C1, C2, C3, and C4 of the stand mounting unit 320, which are defined to correspond thereto, are the same as those in FIG. 13. Similarly, the portable mounting unit 330 may be divided into four virtual regions to correspond to shapes and sizes of A1, A2, A3, and A4. The four regions of the portable mounting unit 330 may be defined as E1, E2, E3, and E4.

The magnet may be mounted in the table mounting unit 310, the stand mounting unit 320, and the portable mounting unit 330. In the portable mounting unit 330, the magnet may be mounted on, for example, an inner surface or an outer surface of the frame 332.

The magnet of the table mounting unit 310 and the magnet of the stand mounting unit 320 may be mounted in regions or positions that correspond to each other. The magnet of the table mounting unit 310 and the magnet of the stand mounting unit 320 may be aligned by different polarities. The magnet of the portable mounting unit 330 may be mounted in a region that does not correspond to the magnet of the table mounting unit 310 or the magnet of the stand mounting unit 320. The magnet of the portable mounting unit 330 may be aligned by the same polarity as the table mounting unit 310, or may be aligned by the same polarity as the stand mounting unit 320.

Figure 15A:
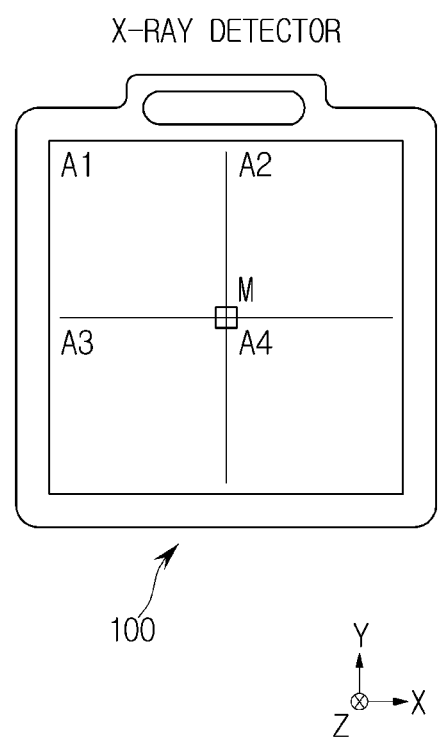
FIGS. 15A, 15B, 15C, 15D, 15E, 15F and 15G ("FIG. 15") are diagrams illustrating another example of the detector detecting unit including the linear magnetic sensor.
Figure 15B:
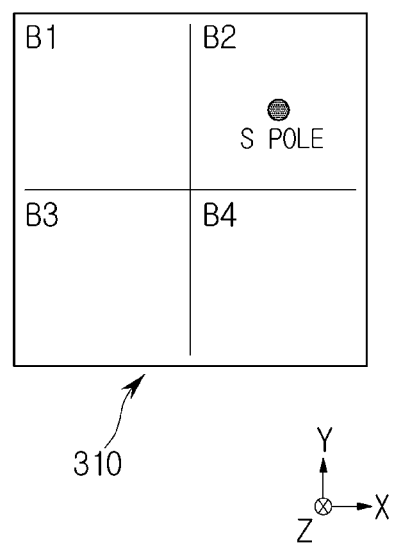
Figure 15C:
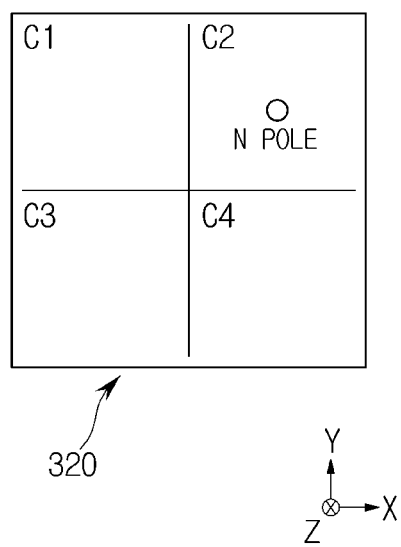
Figure 15D:
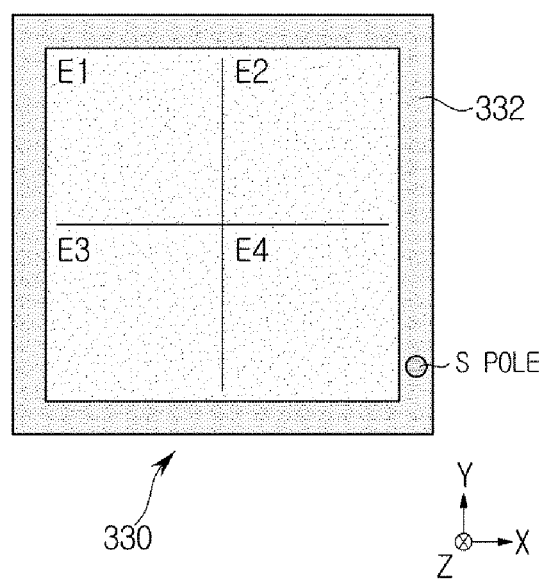

For example, as illustrated in FIGS. 15B, 15C and 15D, the magnet of the table mounting unit 310 may be mounted in the region B2, the magnet of the stand mounting unit 320 may be mounted in the region C2, and the magnet of the portable mounting unit 330 may be mounted in the region E4. Also, the magnet of the table mounting unit 310 and the magnet of the portable mounting unit 330 may be aligned by an S pole and the magnet of the stand mounting unit 320 may be aligned by an N pole.

Figure 15E:
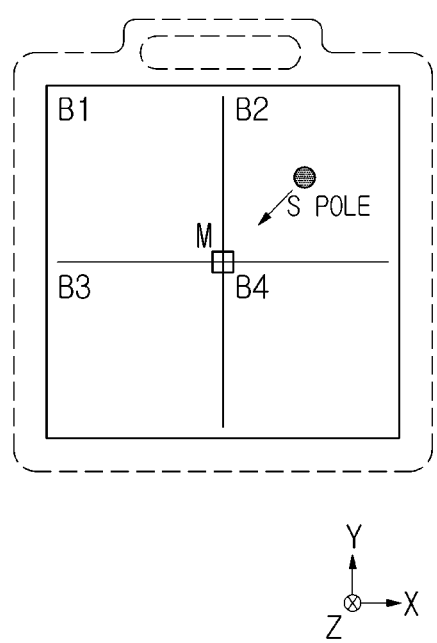
Figure 15F:
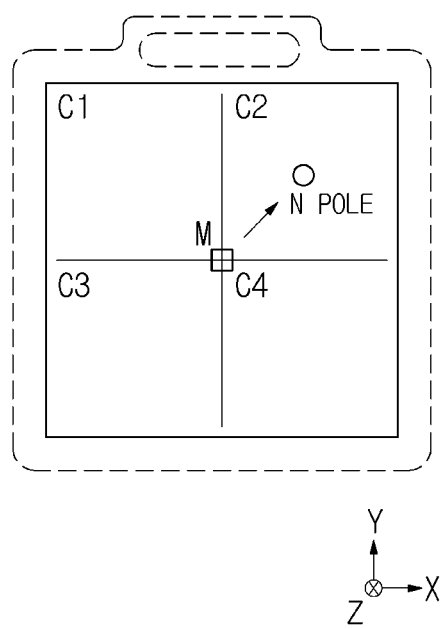
Figure 15G:
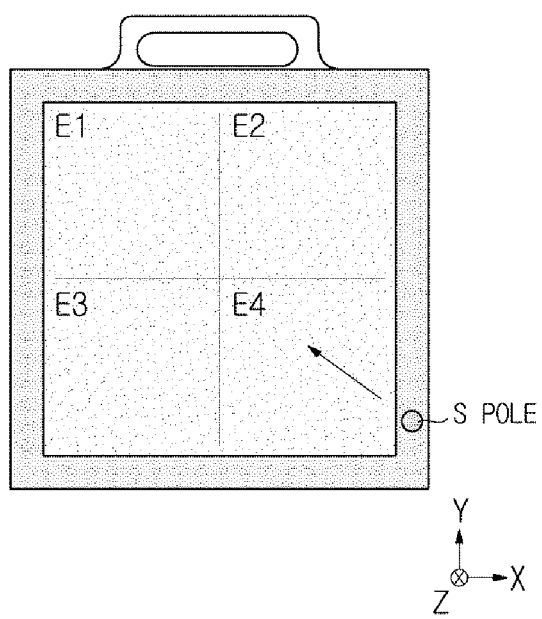

Accordingly, the linear magnetic sensor M detects a different magnetic field direction according to whether the X-ray detector 100 is mounted in the table mounting unit 310, the stand mounting unit 320, or the portable mounting unit 330. When the X-ray detector 100 is mounted in the table mounting unit 310, that is, when the X-ray detector 100 is implemented in a table type, the linear magnetic sensor M detects magnetic field lines output from the top right, as illustrated in FIG. 15E. On the other hand, when the X-ray detector 100 is mounted in the stand mounting unit 320, that is, when the X-ray detector 100 is implemented in a stand type, the linear magnetic sensor M detects magnetic field lines entering at the top right as illustrated in FIG. 15F. Also, when the X-ray detector 100 is mounted in the portable mounting unit 330, that is, when the X-ray detector 100 is implemented in a portable type, the linear magnetic sensor M detects magnetic field lines output from the bottom right as illustrated in FIG. 15G.

That is, as illustrated in FIG. 16, when the X-ray detector 100 is implemented in a table type, the linear magnetic sensor M detects a magnetic field direction of (x, y, z)=(+, +, +). When the X-ray detector 100 is implemented in a stand type, the linear magnetic sensor M detects a magnetic field direction of (x, y, z)=(−, −, +). When the X-ray detector 100 is implemented in a portable type, the linear magnetic sensor M detects a magnetic field direction of (x, y, z)=(+, −, +). That is, the linear magnetic sensor M detects a different magnetic field in an x axis direction or a y axis direction according to the mounting unit 300 in which the X-ray detector 100 is mounted.

Similarly, when the plurality of X-ray detectors 100 exemplified in FIG. 15 are provided, the linear magnetic sensor M of the X-ray detector 100 implemented in a table type, the linear magnetic sensor M of the X-ray detector 100 implemented in a stand type, or the linear magnetic sensor M of the X-ray detector 100 implemented in a portable type detects a different magnetic field direction.

FIG. 17 is a diagram illustrating still another example of the detector detecting unit including the linear magnetic sensor.

As illustrated in FIG. 17, the detector detecting unit 140 of the X-ray detector 100 and four virtual regions A1, A2, A3, and A4 of the X-ray detector 100 are the same as those in FIG. 13A. Also, four regions B1, B2, B3, and B4 of the table mounting unit 310 and four regions C1, C2, C3, and C4 of the stand mounting unit 320, which are defined to correspond to the regions A1, A2, A3, and A4, are the same as those in FIG. 13.

Figure 17A:
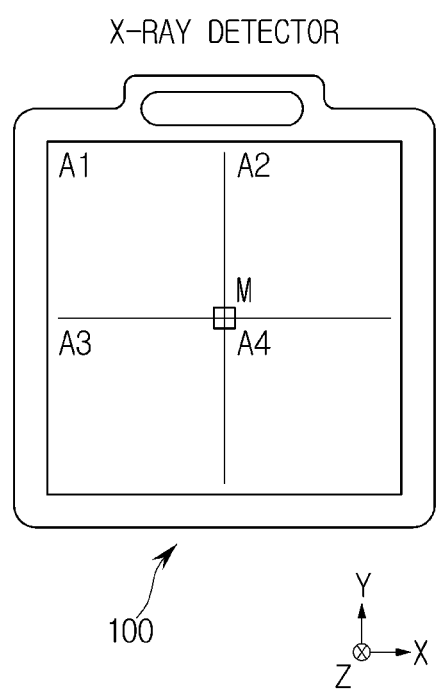
FIGS. 17A, 17B, 17C, 17D and 17E ("FIG. 17") are diagrams illustrating still another example of the detector detecting unit including the linear magnetic sensor.
Figure 17B:
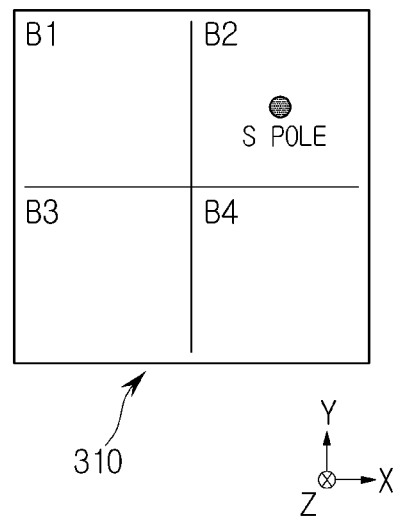
Figure 17C:
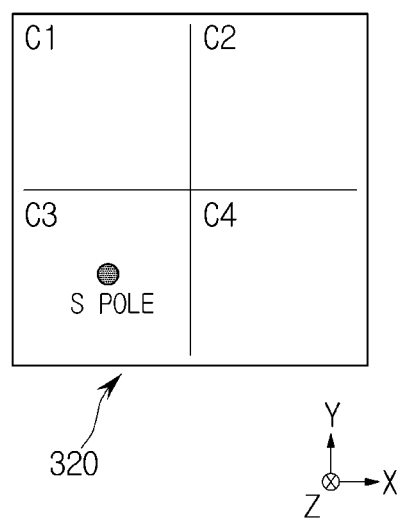

The magnet may be mounted in the table mounting unit 310 and the stand mounting unit 320. The magnet of the table mounting unit 310 and the magnet of the stand mounting unit 320 may be mounted in different regions. The magnet of the table mounting unit 310 and the magnet of the stand mounting unit 320 may be aligned by the same polarity. For example, as illustrated in FIGS. 17B and 17C, the magnet of the table mounting unit 310 may be mounted in the region B2, and the magnet of the stand mounting unit 320 may be mounted in the region C3. In addition, the magnet of the table mounting unit 310 and the magnet of the stand mounting unit 320 may be aligned by the same polarity, for example, an S pole.

Figure 17D:
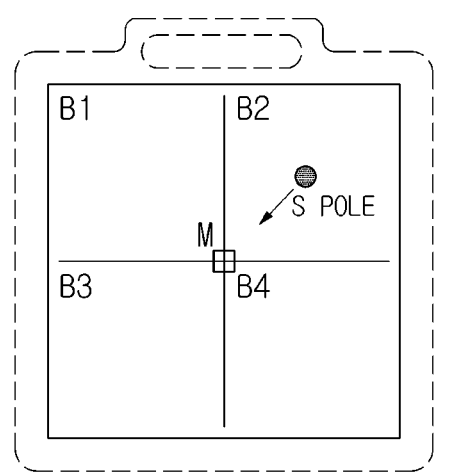
Figure 17E:
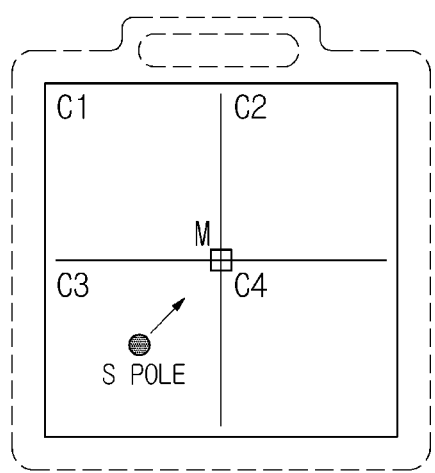

Accordingly, the linear magnetic sensor M detects a different magnetic field direction according to whether the X-ray detector 100 is mounted in the table mounting unit 310 or in the stand mounting unit 320. When the X-ray detector 100 is mounted in the table mounting unit 310, the linear magnetic sensor M detects the magnetic field from the top right as illustrated in FIG. 17D. On the other hand, when the X-ray detector 100 is mounted in the stand mounting unit 320, the linear magnetic sensor M detects the magnetic field from the bottom left as illustrated in FIG. 17E. That is, when the X-ray detector 100 is implemented in a table type, the linear magnetic sensor M detects a magnetic field direction of (x, y, z)=(+, +, +). When the X-ray detector 100 is implemented in a stand type, the linear magnetic sensor M detects a magnetic field direction of (x, y, z)=(−, −, +).

Similarly, when the plurality of X-ray detectors 100 exemplified in FIG. 17 are provided, the linear magnetic sensor M of the X-ray detector 100 implemented in a table type and the linear magnetic sensor M of the X-ray detector 100 implemented in a stand type detect different magnetic field directions.

FIGS. 18A, 18B, 18C, 18D, 18E, 18F and 18G (FIG. 18″) are diagrams illustrating still another example of the detector detecting unit including the linear magnetic sensor. As illustrated in FIG. 18, the X-ray imaging apparatus 1 may further include the portable mounting unit 330 in addition to the table mounting unit 310 and the stand mounting unit 320.

The detector detecting unit 140 of the X-ray detector 100 and four virtual regions A1, A2, A3, and A4 of the X-ray detector 100 are the same as those in FIG. 13A or 15A. Also, four regions B1, B2, B3, and B4 of the table mounting unit 310, four regions C1, C2, C3, and C4 of the stand mounting unit 320, and four regions E1, E2, E3, and E4 of the portable mounting unit 330, which are defined to correspond to the regions A1, A2, A3, and A4, are the same as those in FIG. 13 or 15.

The magnet may be mounted in the table mounting unit 310, the stand mounting unit 320, and the portable mounting unit 330. The magnet of the table mounting unit 310, the magnet of the stand mounting unit 320, and the magnet of the portable mounting unit 330 may be mounted in different regions. Each of the magnet of the table mounting unit 310, the magnet of the stand mounting unit 320, and the magnet of the portable mounting unit 330 may be aligned by the same polarity.

Figure 18A:
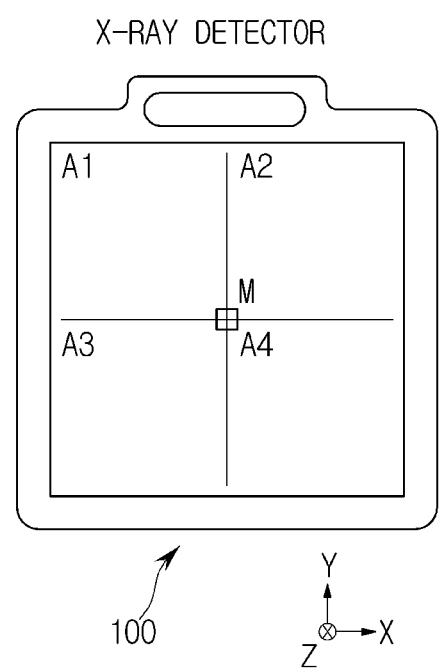
FIGS. 18A, 18B, 18C, 18D, 18E, 18F and 18G ("FIG. 18") are diagrams illustrating still another example of the detector detecting unit including the linear magnetic sensor.
Figure 18B:
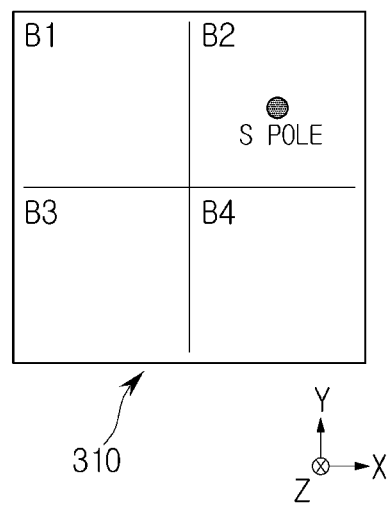
Figure 18C:
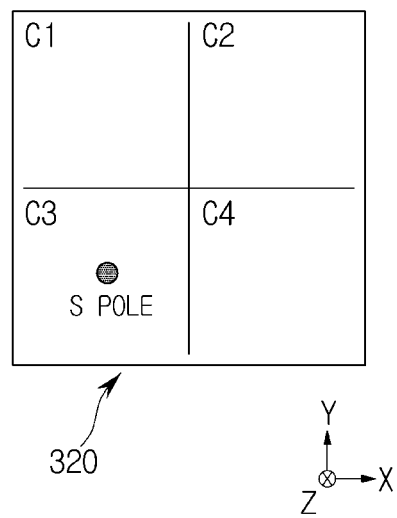
Figure 18D:
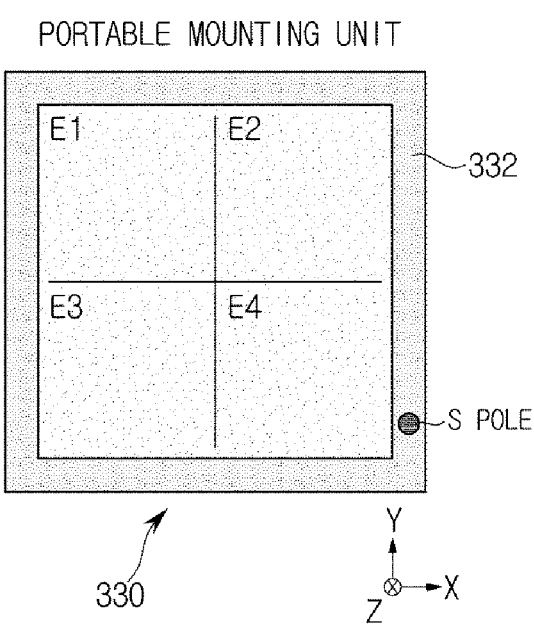

For example, as illustrated in FIGS. 18B to 18D, the magnet of the table mounting unit 310 may be mounted in the region B2, the magnet of the stand mounting unit 320 may be mounted in the region C3, and the magnet of the portable mounting unit 330 may be mounted in the region E4. Also, each of the magnet of the table mounting unit 310, the magnet of the stand mounting unit 320, and the magnet of the portable mounting unit 330 may be aligned by an S pole.

Accordingly, the linear magnetic sensor M detects a different magnetic field direction according to whether the X-ray detector 100 is mounted in the table mounting unit 310, in the stand mounting unit 320, or in the portable mounting unit 330.

Figure 18E:
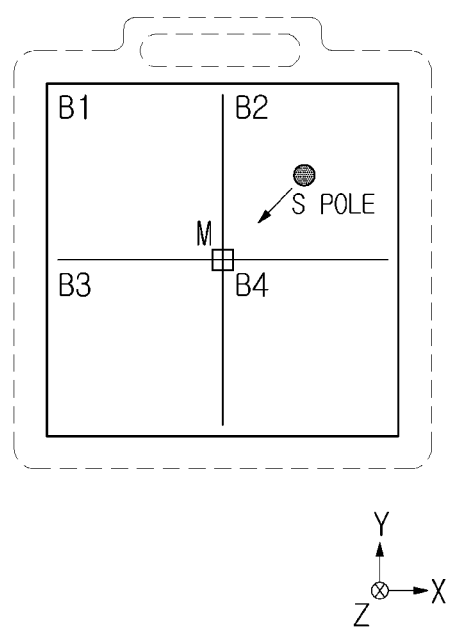
Figure 18F:
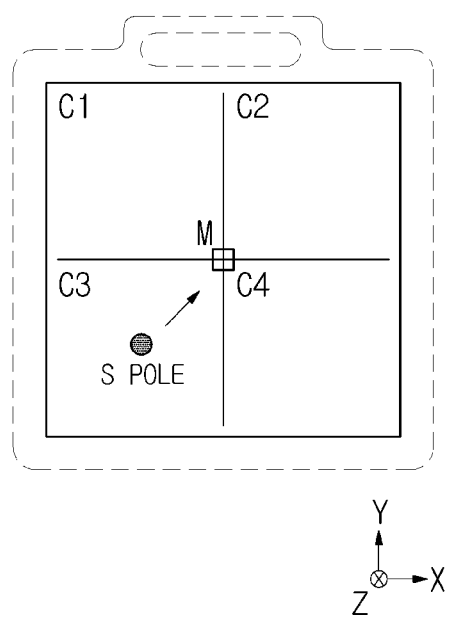
Figure 18G:
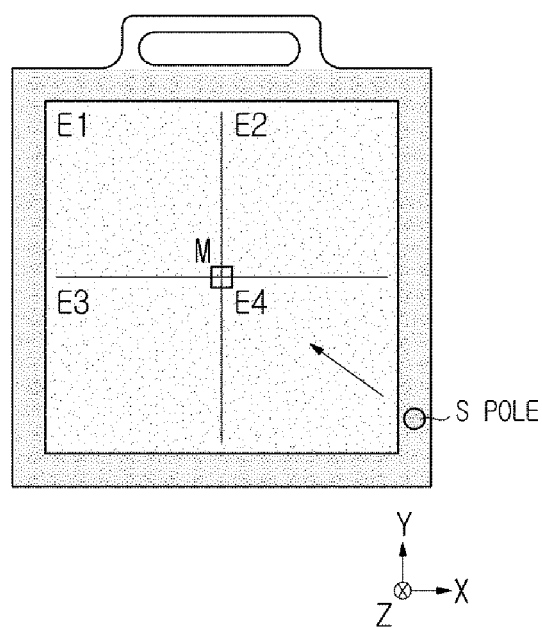

When the X-ray detector 100 is mounted in the table mounting unit 310, the linear magnetic sensor M detects a magnetic field from the top right as illustrated in FIG. 18E. That is, the linear magnetic sensor M detects a magnetic field direction of (x, y, z)=(+, +, +). When the X-ray detector 100 is mounted in the stand mounting unit 320, the linear magnetic sensor M detects a magnetic field from the bottom right as illustrated in FIG. 18F. That is, the linear magnetic sensor M detects a magnetic field direction of (x, y, z)=(−, −, +). Also, when the X-ray detector 100 is mounted in the portable mounting unit 330, the linear magnetic sensor M detects the magnetic field from the bottom left as illustrated in FIG. 18G. That is, the linear magnetic sensor M detects a magnetic field direction of (x, y, z)=(+, −, +).

Similarly, when the plurality of X-ray detectors 100 exemplified in FIG. 18 are provided, the linear magnetic sensor M of the X-ray detector 100 implemented in a table type, the linear magnetic sensor M of the X-ray detector 100 implemented in a stand type, or the linear magnetic sensor M of the X-ray detector 100 implemented in a portable type detects a different magnetic field direction.

While the detector detecting unit 140 including the single linear magnetic sensor M is exemplified in FIGS. 13 to 18, the detector detecting unit 140 may also include a plurality of linear magnetic sensors M.

Figure 19A:
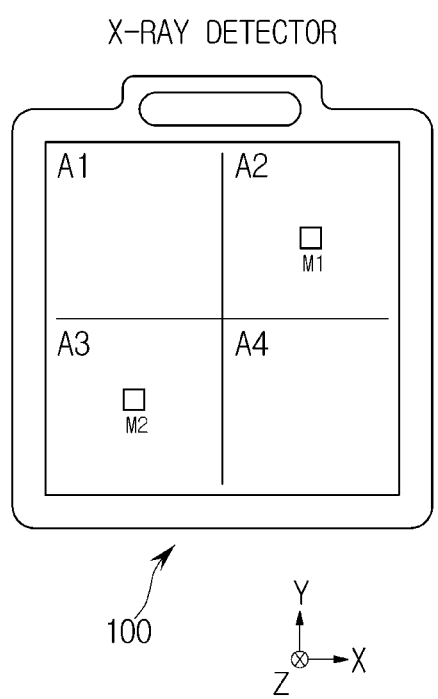
FIGS. 19A, 19B, 19C, 19D and 19E ("FIG. 19") are diagrams illustrating an example of a detector detecting unit including a plurality of linear magnetic sensors.
Figure 19B:
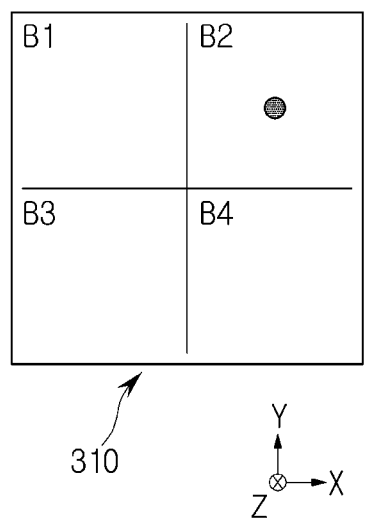
Figure 19C:
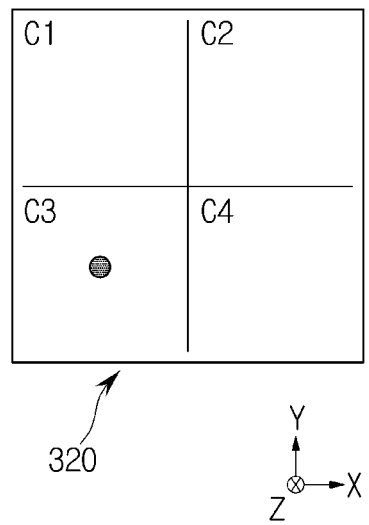

FIGS. 19A, 19 B, 19C, 19D and 19E (FIG. 19″) are diagrams illustrating an example of a detector detecting unit including a plurality of linear magnetic sensors.

As illustrated in FIG. 19, the X-ray detector 100 may include the detector detecting unit 140 having two linear magnetic sensors M1 and M2. In this case, the two linear magnetic sensors M1 and M2 may be a predetermined distance from each other. While the single X-ray detector 100 is exemplified in FIG. 19, the plurality of X-ray detectors 100 may be provided. In this case, all of the X-ray detectors 100 have the same number of linear magnetic sensors M1 and M2 at the same positions.

The two linear magnetic sensors may be distinguished as the first linear magnetic sensor M1 and the second linear magnetic sensor M2. The X-ray detector 100 may be divided into a plurality of virtual regions such that the first linear magnetic sensor M1 and the second linear magnetic sensor M2 are separated. As exemplified in FIG. 19A, the X-ray detector 100 may be divided into four virtual regions, that is, A1, A2, A3, and A4.

A1, A2, A3, and A4 may have the same shape and size or different shapes and sizes. Each of the table mounting unit 310 and the stand mounting unit 320 may be divided into four virtual regions to correspond to shapes and sizes of A1, A2, A3, and A4. The table mounting unit 310 may be divided into four regions B1, B2, B3, and B4, and the stand mounting unit 320 may be divided into four regions C1, C2, C3, and C4.

The magnet may be mounted in the table mounting unit 310 and the stand mounting unit 320. The magnet of the table mounting unit 310 and the magnet of the stand mounting unit 320 may be mounted in different regions. One of the magnet of the table mounting unit 310 and the magnet of the stand mounting unit 320 may be provided in a region or a position corresponding to the first linear magnetic sensor M1, and the other magnet may be provided in a region or a position corresponding to the second linear magnetic sensor M2. As exemplified in FIGS. 19B and 19C, the magnet of the table mounting unit 310 may be provided in the region B2, and the magnet of the stand mounting unit 320 may be provided in the region C3. The magnet of the table mounting unit 310 may be provided to correspond to a position of the first linear magnetic sensor M1, and the magnet of the stand mounting unit 320 may be provided to correspond to a position of the second linear magnetic sensor M2.

The magnet of the table mounting unit 310 and the magnet of the stand mounting unit 320 may be aligned by the same polarity. Both the magnet of the table mounting unit 310 and the magnet of the stand mounting unit 320 may be aligned by an S pole or an N pole.

Accordingly, the two linear magnetic sensors M1 and M2 detect different magnetic fields according to a mounting position of the X-ray detector 100. A magnetic field strength detected by the first linear magnetic sensor M1 and a magnetic field strength detected by the second linear magnetic sensor M2 become different according to whether the X-ray detector 100 is mounted in the table mounting unit 310 or in the stand mounting unit 320.

Figure 19D:
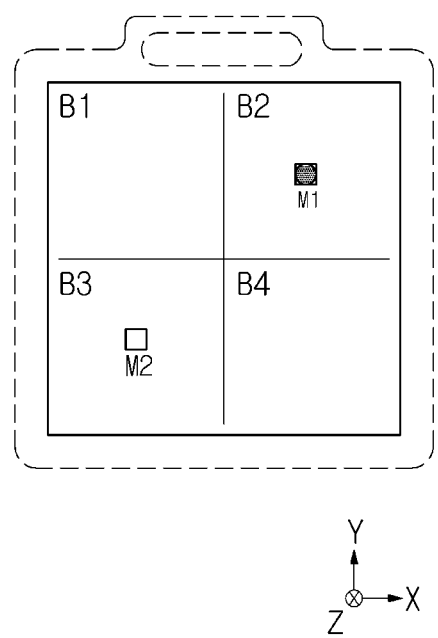
Figure 19E:
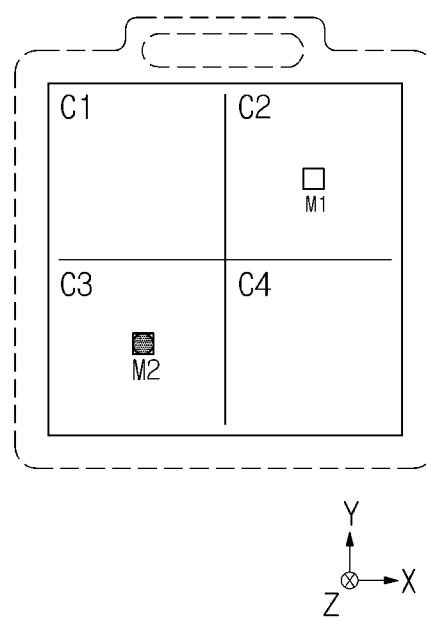

When the X-ray detector 100 is mounted in the table mounting unit 310 in FIG. 19D, that is, when the X-ray detector 100 is implemented in a table type, the first linear magnetic sensor M1 detects a magnetic field strength that is relatively greater than that of the second linear magnetic sensor M2. On the other hand, when the X-ray detector 100 is mounted in the stand mounting unit 320 in FIG. 19E, that is, when the X-ray detector 100 is implemented in a stand type, the second linear magnetic sensor M2 detects a magnetic field strength that is relatively greater than that of the first linear magnetic sensor M1.

Similarly, when the plurality of X-ray detectors 100 exemplified in FIG. 19 are provided, the linear magnetic sensors M1 and M2 of the X-ray detector 100 implemented in a table type and the linear magnetic sensors M1 and M2 of the X-ray detector 100 implemented in a stand type detect different magnetic fields.

The control unit 250 to be described may determine a position in which the X-ray detector 100 is mounted using a magnetic field strength detected by the plurality of linear magnetic sensors M in this manner. When the X-ray detector 100 is mounted, sensor values of the plurality of linear magnetic sensors M may be stored in the detector storage unit 170 temporarily or non-temporarily.

FIGS. 20A, 20B, 20C, 20D, 20E, 20F and 20G ("FIG. 20") are diagrams illustrating another example of the detector detecting unit including the plurality of linear magnetic sensors.

As illustrated in FIG. 20, the X-ray imaging apparatus 1 may further include the portable mounting unit 330 in addition to the table mounting unit 310 and the stand mounting unit 320.

The X-ray detector 100 may include the detector detecting unit 140 having three linear magnetic sensors M1, M2, and M3. In this case, the three linear magnetic sensors M1, M2, and M3 may be a predetermined distance from each other. For example, the detector detecting unit 140 includes the above-described first linear magnetic sensor M1 and second linear magnetic sensor M2, and may include another linear magnetic sensor M3 that is separated from the first linear magnetic sensor M1 and the second linear magnetic sensor M2. In this case, another linear magnetic sensor M3 may be called a third linear magnetic sensor. When the plurality of X-ray detectors 100 are provided, all of the X-ray detectors 100 include the same number of linear magnetic sensors M1 and M2 at the same positions.

The X-ray detector 100 may be divided into a plurality of virtual regions such that the first linear magnetic sensor M1, the second linear magnetic sensor M2, and the third linear magnetic sensor M3 are separated. As exemplified in FIG. 20A, the X-ray detector 100 is divided into four virtual regions, that is, A1, A2, A3, and A4. The first linear magnetic sensor M1 may be included in the region A2. The second linear magnetic sensor M2 may be included in the region A3. The third linear magnetic sensor M3 may be included in the region A4.

A1, A2, A3, and A4 may have the same shape and size or different shapes and sizes. Each of the table mounting unit 310, the stand mounting unit 320, and the portable mounting unit 330 may be divided into four virtual regions to correspond to shapes and sizes of A1, A2, A3, and A4. The table mounting unit 310 may be divided into four regions B1, B2, B3, and B4. The stand mounting unit 320 may be divided into four regions C1, C2, C3, and C4. The portable mounting unit 330 may be divided into E1, E2, E3, and E4.

The magnet may be mounted in the table mounting unit 310, the stand mounting unit 320, and the portable mounting unit 330. The magnet of the table mounting unit 310, the magnet of the stand mounting unit 320, and the magnet of the portable mounting unit 330 may be mounted in different regions. One of the magnet of the table mounting unit 310, the magnet of the stand mounting unit 320, and the magnet of the portable mounting unit 330 may be provided in a region or a position corresponding to the first linear magnetic sensor M1, another magnet may be provided in a region or a position corresponding to the second linear magnetic sensor M2, and the other magnet may be provided in a region or a position corresponding to the third linear magnetic sensor M3.

Figure 20A:
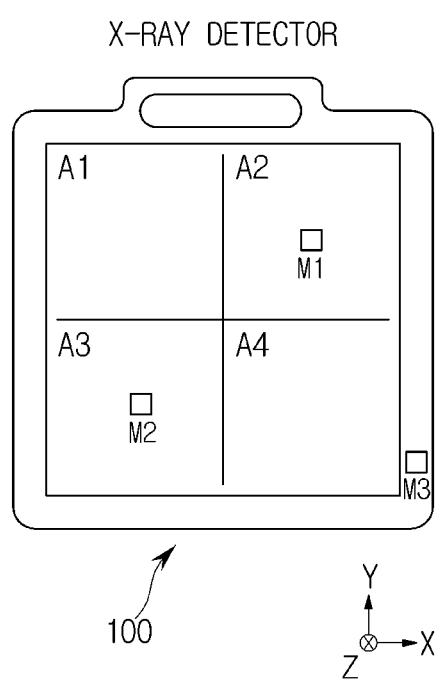
FIGS. 20A, 20B, 20C, 20D, 20E, 20F and 20G ("FIG. 20") are diagrams illustrating another example of the detector detecting unit including the plurality of linear magnetic sensors.
Figure 20B:
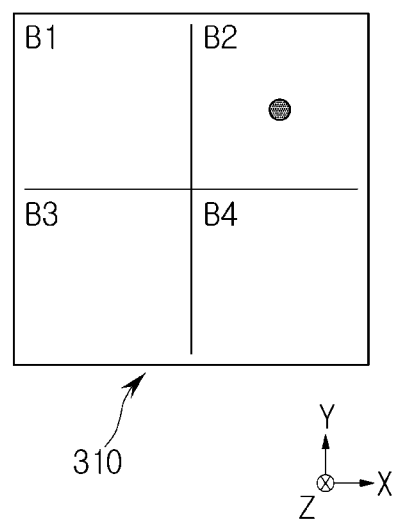
Figure 20C:
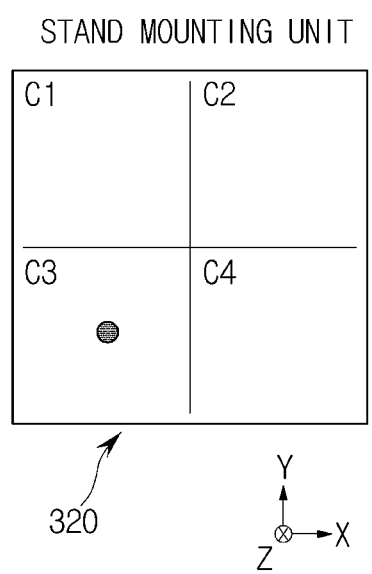
Figure 20D:
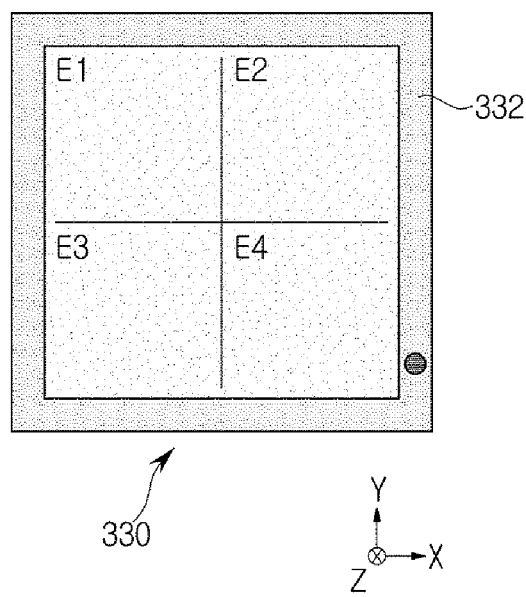
Figure 20E:
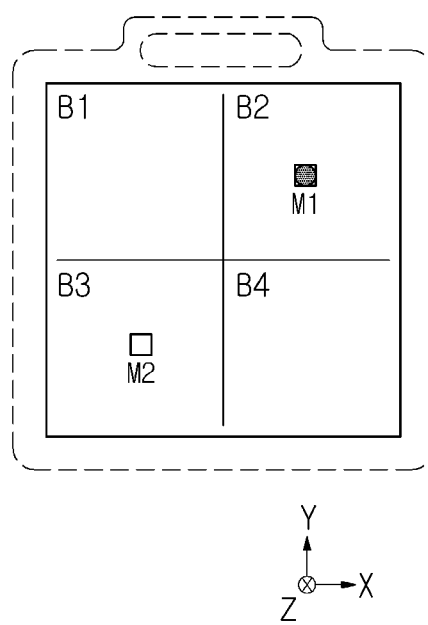
Figure 20F:
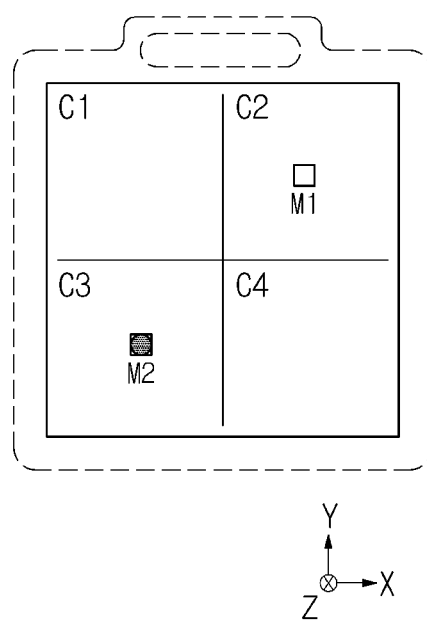
Figure 20G:
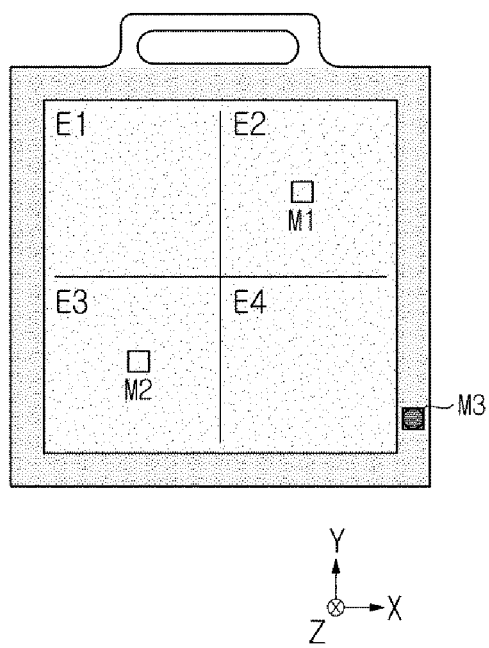

As exemplified in FIGS. 20B to 20D, the magnet of the table mounting unit 310 may be provided in the region B2, the magnet of the stand mounting unit 320 may be provided in the region C3, and the magnet of the portable mounting unit 330 may be provided in the region E4. The magnet of the table mounting unit 310 may be provided to correspond to a position of the first linear magnetic sensor M1, the magnet of the stand mounting unit 320 may be provided to correspond to a position of the second linear magnetic sensor M2, and the magnet of the portable mounting unit 330 may be provided to correspond to a position of the third linear magnetic sensor M3.

The magnet of the table mounting unit 310, the magnet of the stand mounting unit 320, and the magnet of the portable mounting unit 330 may be aligned by the same polarity. The magnet of the table mounting unit 310, the magnet of the stand mounting unit 320, and the magnet of the portable mounting unit 330 may be aligned by an S pole or an N pole.

Accordingly, the three linear magnetic sensors M1, M2, and M3 detect different magnetic fields according to a mounting position of the X-ray detector 100. A magnetic field strength detected by the first linear magnetic sensor M1, a magnetic field strength detected by the second linear magnetic sensor M2, and a magnetic field strength detected by the third linear magnetic sensor M3 become different according to whether the X-ray detector 100 is mounted in the table mounting unit 310, in the stand mounting unit 320, or in the portable mounting unit 330.

When the X-ray detector 100 is mounted in the table mounting unit 310, that is, when the X-ray detector 100 is implemented in a table type, the first linear magnetic sensor M1 detects a magnetic field strength that is relatively greater than that of the second linear magnetic sensor M2 or the third linear magnetic sensor M3. When the X-ray detector 100 is mounted in the stand mounting unit 320, that is, when the X-ray detector 100 is implemented in a stand type, the second linear magnetic sensor M2 detects a magnetic field strength that is relatively greater than that of the first linear magnetic sensor M1 or the third linear magnetic sensor M3. Also, when the X-ray detector 100 is mounted in the portable mounting unit 330, that is, when the X-ray detector 100 is implemented in a portable type, the third linear magnetic sensor M3 detects a magnetic field strength that is relatively greater than that of the first linear magnetic sensor M1 or the second linear magnetic sensor M2.

Similarly, when the plurality of X-ray detectors 100 exemplified in FIG. 20 are provided, the linear magnetic sensors M1, M2, and M3 of the X-ray detector 100 implemented in a table type, the linear magnetic sensors M1, M2, and M3 of the X-ray detector 100 implemented in a stand type, or the linear magnetic sensors M1, M2, and M3 of the X-ray detector 100 implemented in a portable type detect different magnetic fields.

FIGS. 21A, 21B, 21C, 21D and 21E ("FIG. 21") are diagrams illustrating still another example of the detector detecting unit including the plurality of linear magnetic sensors.

As illustrated in FIG. 21, the X-ray detector 100 may include the detector detecting unit 140 including four linear magnetic sensors M1, M2, M3, and M4. In this case, the four linear magnetic sensors M1, M2, M3, and M4 may be a predetermined distance from each other. The four linear magnetic sensors M1, M2, M3, and M4 may be distinguished as the first linear magnetic sensor M1, the second linear magnetic sensor M2, the third linear magnetic sensor M3, and the fourth linear magnetic sensor M4.

The X-ray detector 100 may be divided into a plurality of virtual regions, for example, A1, A2, A3, and A4, such that the first linear magnetic sensor M1, the second linear magnetic sensor M2, the third linear magnetic sensor M3, and the fourth linear magnetic sensor M4 are separated.

Each of the table mounting unit 310 and the stand mounting unit 320 may be divided into four virtual regions to correspond to shapes and sizes of A1, A2, A3, and A4. The table mounting unit 310 may be divided into four regions B1, B2, B3, and B4, and the stand mounting unit 320 may be divided into four regions C1, C2, C3, and C4.

The magnet may be mounted in the table mounting unit 310 and the stand mounting unit 320. Also, the magnet of the table mounting unit 310 and the magnet of the stand mounting unit 320 may be mounted in different regions. As exemplified in FIGS. 20B to 20C, the magnet of the table mounting unit 310 may be provided in the region B2, and the magnet of the stand mounting unit 320 may be provided in the region C3. The magnet of the table mounting unit 310 may be provided to correspond to a position of the first linear magnetic sensor M1, and the magnet of the stand mounting unit 320 may be provided to correspond to a position of the second linear magnetic sensor M2. Also, the magnet of the table mounting unit 310 and the magnet of the stand mounting unit 320 may be aligned by the same polarity.

Accordingly, the four linear magnetic sensors M1, M2, M3, and M4 detect different magnetic fields according to whether the X-ray detector 100 is mounted in the table mounting unit 310 or in the stand mounting unit 320. For example, when the X-ray detector 100 is implemented in a table type, the first linear magnetic sensor M1 detects a magnetic field strength that is relatively greater than that of the remaining sensors, that is, the second to fourth linear magnetic sensors M2, M3, and M4. On the other hand, when the X-ray detector 100 is implemented in a stand type, the second linear magnetic sensor M2 detects a magnetic field strength that is relatively greater than that of the remaining sensors, that is, the first, third, and fourth linear magnetic sensors M1, M3, and M4.

Similarly, when the plurality of X-ray detectors 100 exemplified in FIG. 21 are provided, the linear magnetic sensors M1, M2, M3, and M4 of the X-ray detector 100 implemented in a table type and the linear magnetic sensors M1, M2, M3, and M4 of the X-ray detector 100 implemented in a stand type detect different magnetic fields.

FIGS. 22A, 22B, 22C, 22D, 22E, 22F and 22G ("FIG. 22") are diagrams illustrating still another example of the detector detecting unit including the plurality of linear magnetic sensors. As illustrated in FIG. 22, the X-ray imaging apparatus 1 may further include the portable mounting unit 330 in addition to the table mounting unit 310 and the stand mounting unit 320.

Figure 21A:
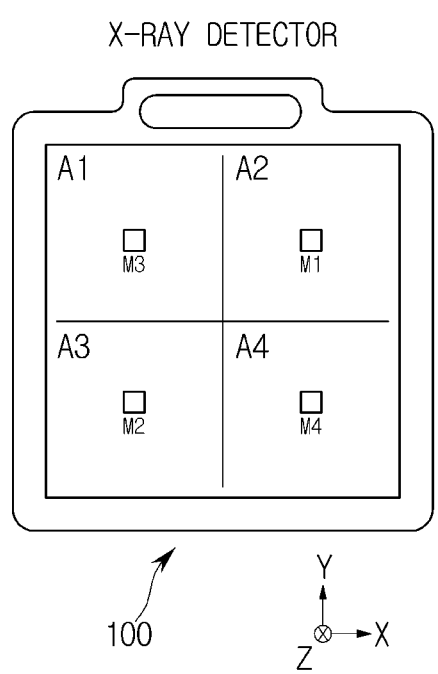
FIGS. 21A, 21B, 21C, 21D and 21E ("FIG. 21") are diagrams illustrating still another example of the detector detecting unit including the plurality of linear magnetic sensors.
Figure 21B:
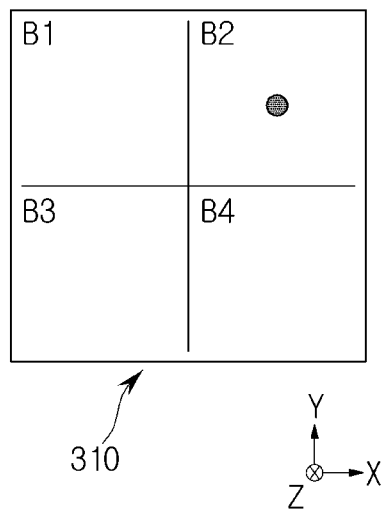
Figure 21C:
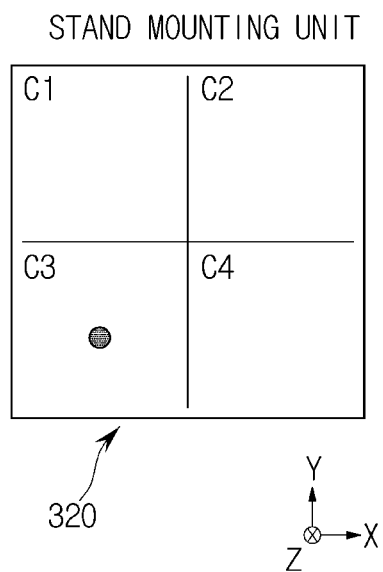
Figure 21D:
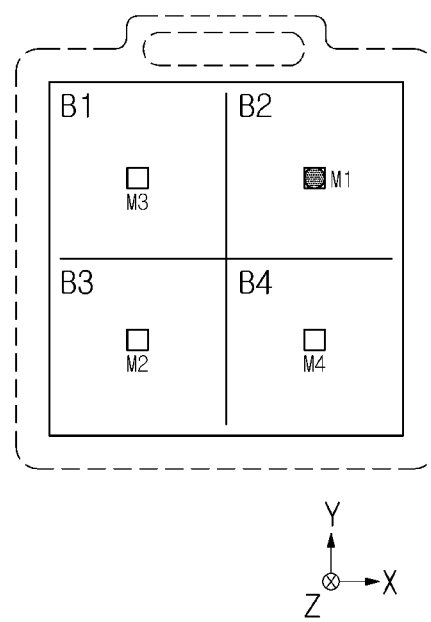
Figure 21E:
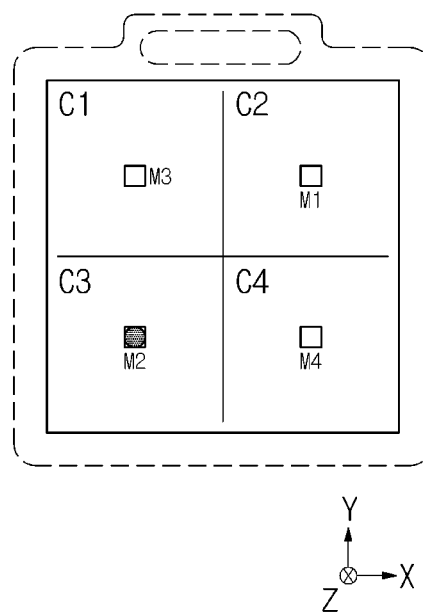

The detector detecting unit 140 of the X-ray detector 100 is the same as in FIG. 21A. Also, four virtual regions A1, A2, A3, and A4 of the X-ray detector 100, and four regions B1, B2, B3, and B4 of the table mounting unit 310 and four regions C1, C2, C3, and C4 of the stand mounting unit 320, which are defined to correspond thereto, are the same as those in FIG. 13. Similarly, the portable mounting unit 310 may be divided into four virtual regions to correspond to shapes and sizes of A1, A2, A3, and A4. The four regions of the portable mounting unit 330 may be defined as E1, E2, E3, and E4.

Figure 22A:
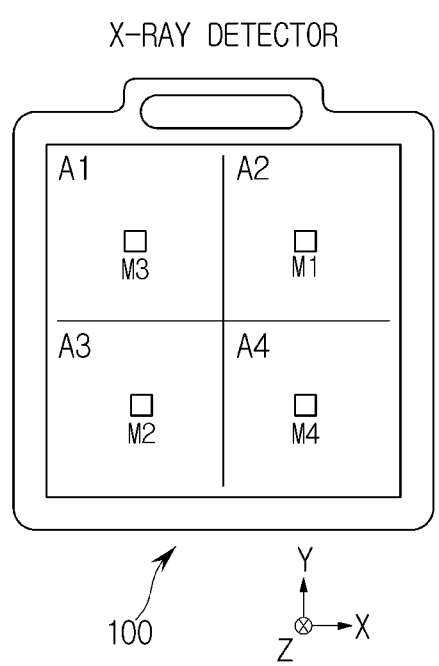
FIGS. 22 A, 22B, 22C, 22D, 22E, 22F and 22G ("FIG. 22") are diagrams illustrating still another example of the detector detecting unit including the plurality of linear magnetic sensors.
Figure 22B:
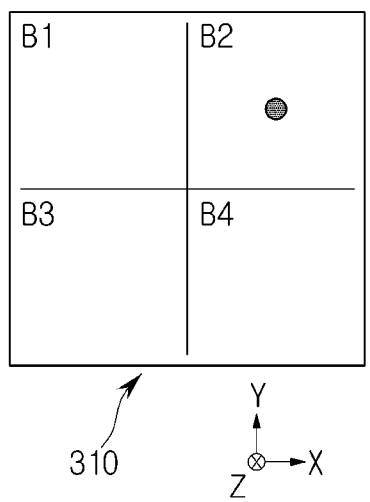
Figure 22C:
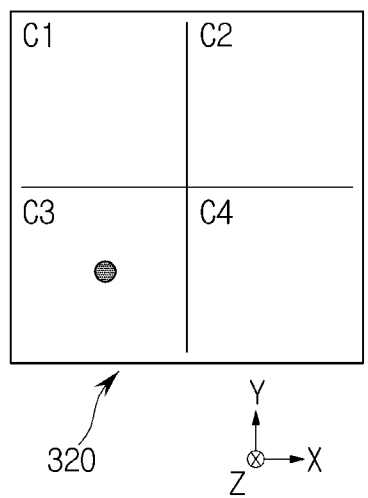
Figure 22D:
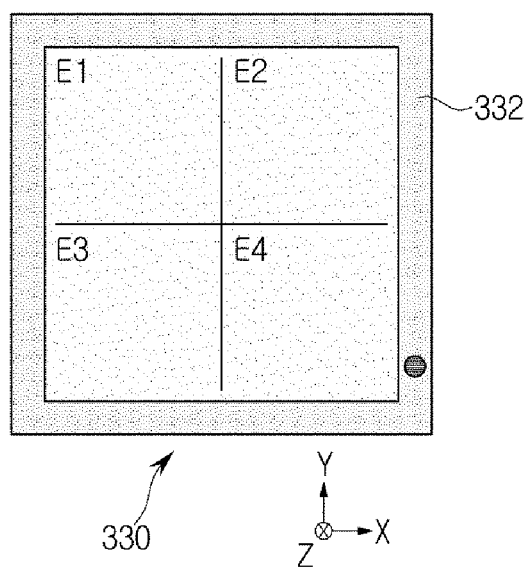
Figure 22E:
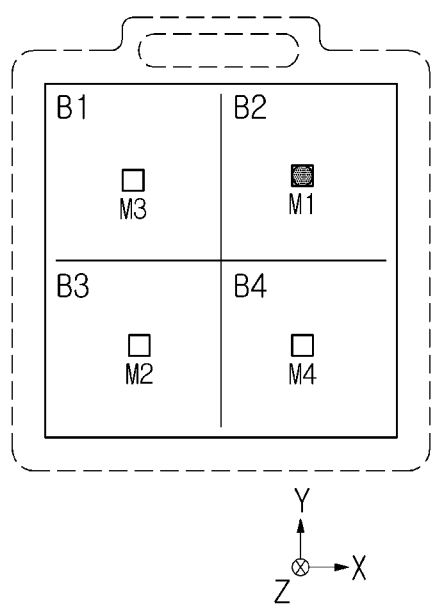
Figure 22F:
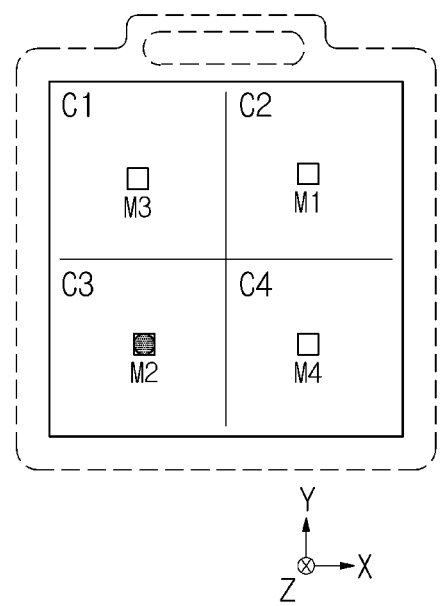
Figure 22G:
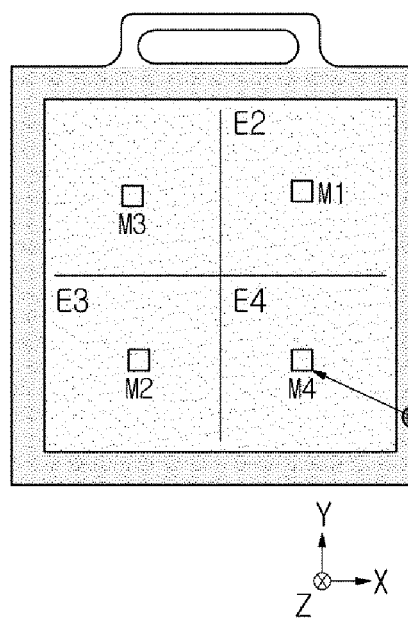

The magnet may be mounted in the table mounting unit 310, the stand mounting unit 320, and the portable mounting unit 330. The magnet of the table mounting unit 310, the magnet of the stand mounting unit 320, and the magnet of the portable mounting unit 330 may be mounted in different regions. For example, as illustrated in FIGS. 22B, 22C and 22D, the magnet of the table mounting unit 310 may be mounted in the region B2, the magnet of the stand mounting unit 320 may be mounted in the region C3, and the magnet of the portable mounting unit 330 may be mounted in the region E4. Also, all of the magnet of the table mounting unit 310, the magnet of the stand mounting unit 320, and the magnet of the portable mounting unit 330 may be aligned by the same polarity.

Accordingly, the four linear magnetic sensors M1, M2, M3, and M4 detect different magnetic fields according to whether the X-ray detector 100 is mounted in the table mounting unit 310, in the stand mounting unit 320, or in the portable mounting unit 330. For example, when the X-ray detector 100 is implemented in a table type, the first linear magnetic sensor M1 detects a magnetic field strength that is relatively greater than that of the remaining sensors, that is, the second, third and fourth linear magnetic sensors M2, M3, and M4. When the X-ray detector 100 is implemented in a stand type, the second linear magnetic sensor M2 detects a magnetic field strength that is relatively greater than that of the remaining sensors, that is, the first, third, and fourth linear magnetic sensors M1, M3, and M4. Also, when the X-ray detector 100 is implemented in a portable type, the fourth linear magnetic sensor M4 detects a magnetic field strength that is relatively greater than that of the remaining sensors, that is, the first, second and third linear magnetic sensors M1, M2, and M3.

Similarly, when the plurality of X-ray detectors 100 exemplified in FIG. 22 are provided, the linear magnetic sensors M1, M2, M3, and M4 of the X-ray detector 100 implemented in a table type, the linear magnetic sensors M1, M2, M3, and M4 of the X-ray detector 100 implemented in a stand type, or the linear magnetic sensors M1, M2, M3, and M4 of the X-ray detector 100 implemented in a portable type detect different magnetic fields.

As described in FIGS. 19A to 22G, the detector detecting unit 140 may include the plurality of linear magnetic sensors M. In this case, the plurality of linear magnetic sensors M may also be grouped.

Figure 23A:
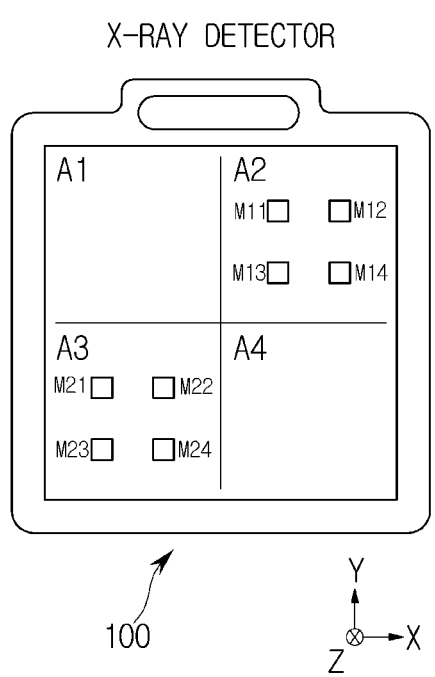
FIGS. 23A, 23B, 23C, 23D and 23E ("FIG. 23") are diagrams illustrating an example of a detector detecting unit including grouped linear magnetic sensors.
Figure 23B:
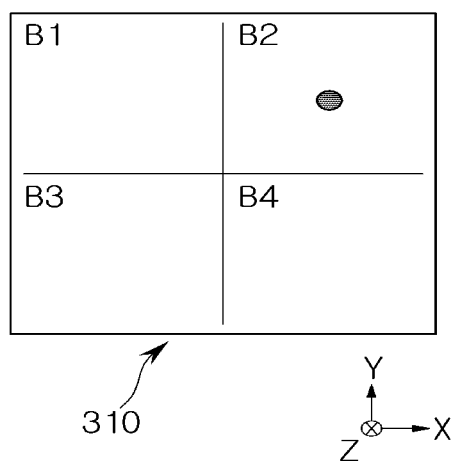
Figure 23C:
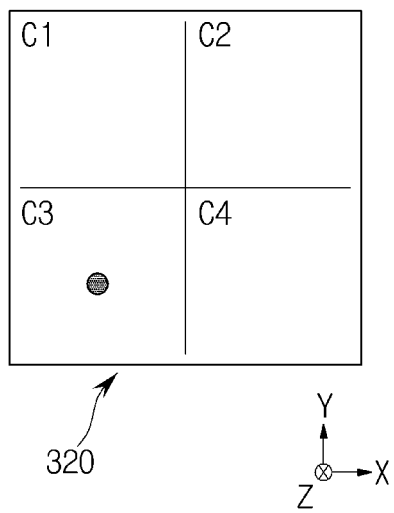
Figure 23D:
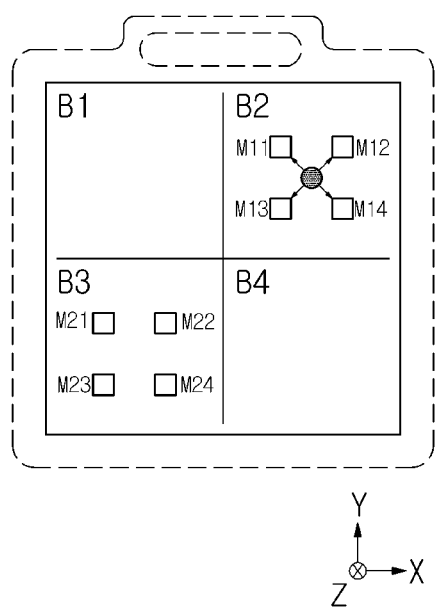
Figure 23E:
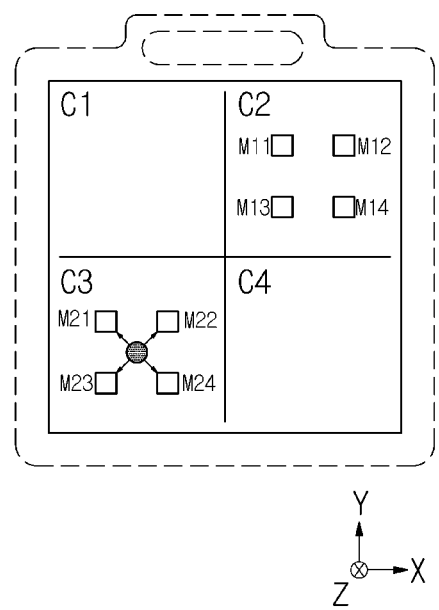
Figure 25A:
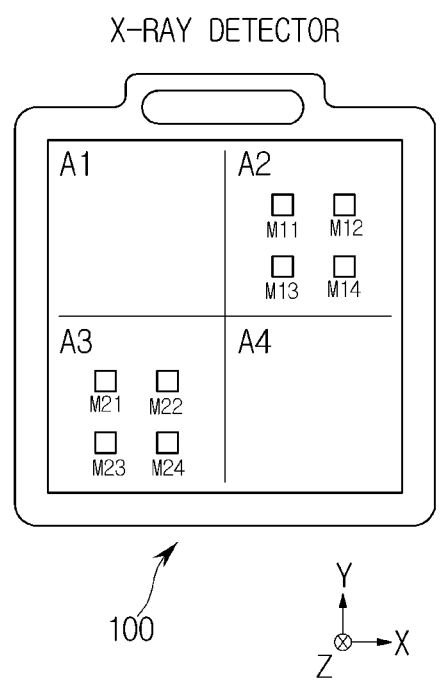
FIGS. 25A, 25B, 25C, 25D, 25E, 25F and 25G ("FIG. 25") are diagrams illustrating another example of the detector detecting unit including the grouped linear magnetic sensors.
Figure 25B:
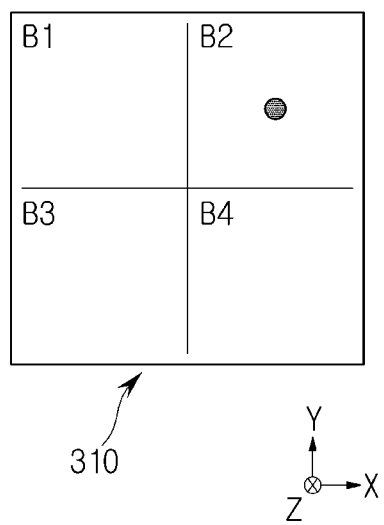
Figure 25C:
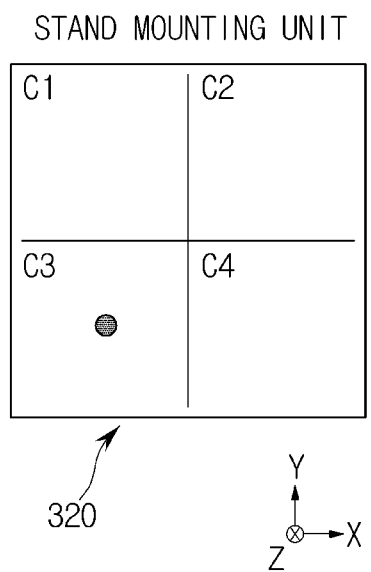
Figure 25D:
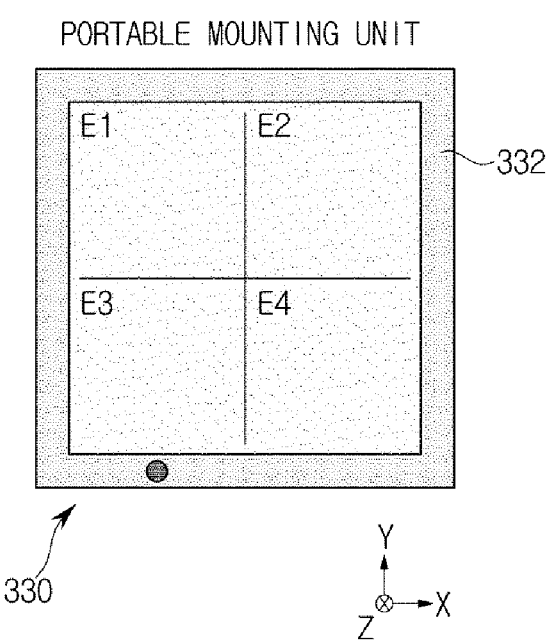
Figure 25E:
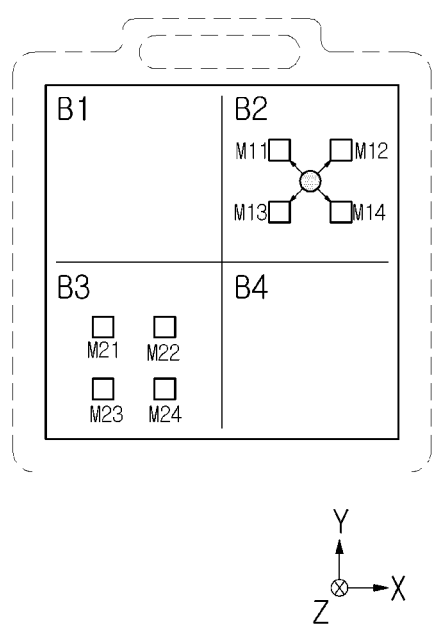
Figure 25F:
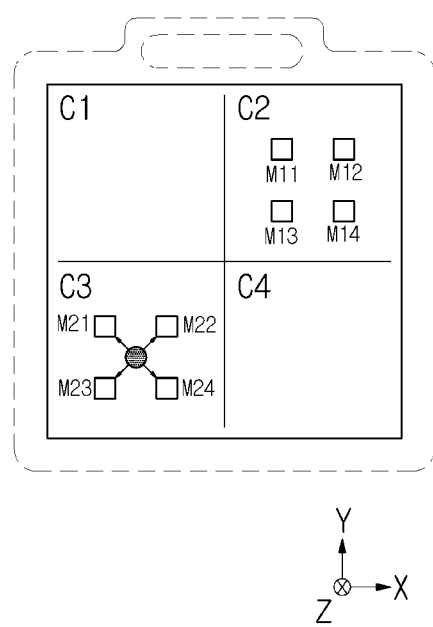
Figure 25G:
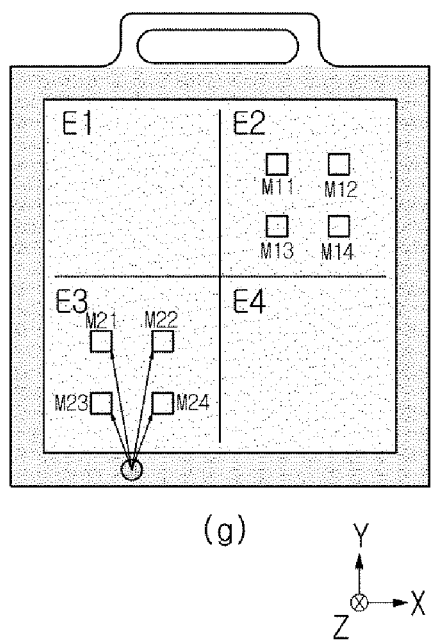
Figure 27A:
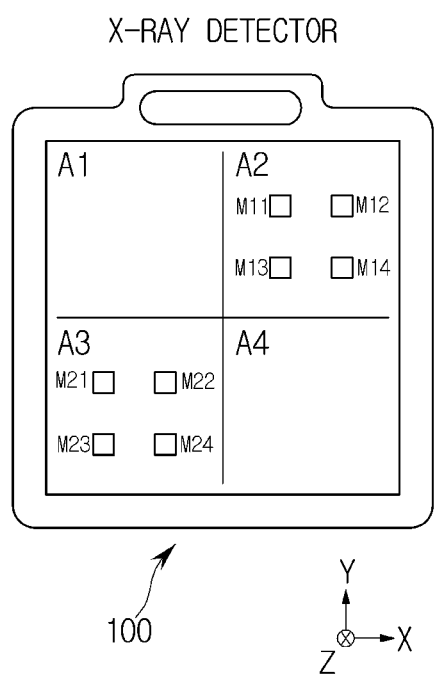
FIGS. 27A, 27B, 27C, 27D and 27E ("FIG. 27") are diagrams illustrating still another example of the detector detecting unit including the grouped linear magnetic sensors.
Figure 27B:
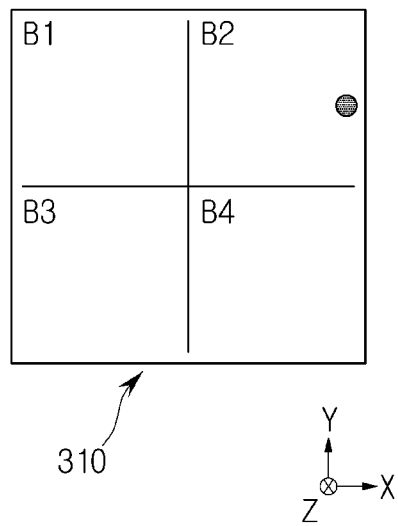
Figure 27C:
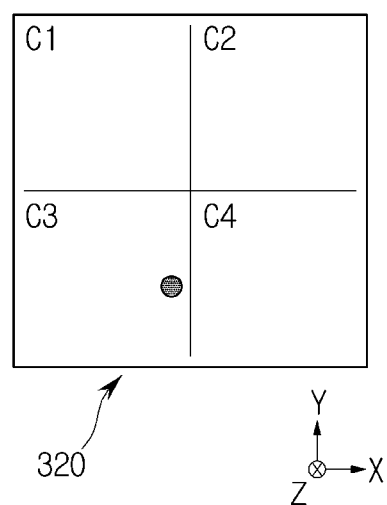
Figure 27D:
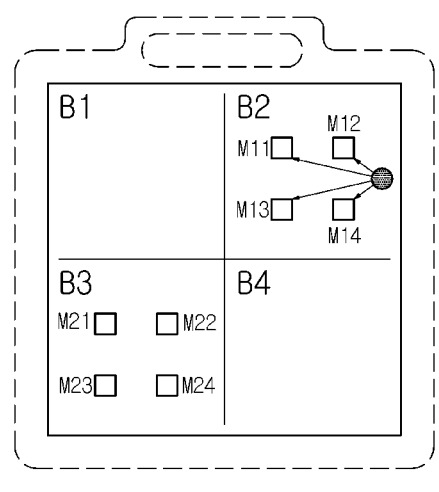
Figure 27E:
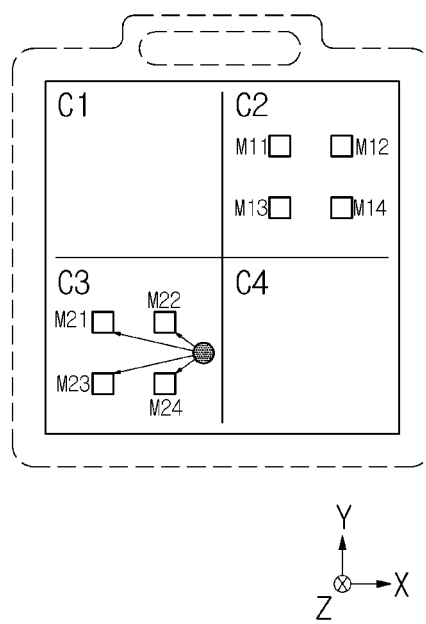

FIGS. 23A. 23B. 23C. 23D and 23E ("FIG. 23") are diagrams illustrating an example of a detector detecting unit including grouped linear magnetic sensors. FIGS. 24A and 24B are diagrams illustrating a magnetic field detected by the linear magnetic sensors of FIG. 23.

As illustrated in FIGS. 23A to 23E, the X-ray detector 100 includes the detector detecting unit 140 having a plurality of linear magnetic sensors M11, M12, M13, M14, M21, M22, M23, and M24. The plurality of linear magnetic sensors M11, M12, M13, M14, M21, M22, M23, and M24 may be grouped as a plurality of sensor groups. The plurality of linear magnetic sensors M11, M12, M13, M14, M21, M22, M23, and M24 may be grouped as a first sensor group and a second sensor group. The first sensor group may include the four linear magnetic sensors M11, M12, M13, and M14, and the second sensor group may include the remaining four linear magnetic sensors M21, M22, M23, and M24. While the single X-ray detector 100 is exemplified in FIG. 23, the plurality of X-ray detectors 100 may also be provided. In this case, all of the X-ray detectors 100 include the same sensor group at the same positions.

The X-ray detector 100 may be divided into a plurality of virtual regions such that the plurality of sensor groups are separated. As exemplified in FIG. 19A, the X-ray detector 100 may be divided into four virtual regions, that is, A1, A2, A3, and A4. A1, A2, A3, and A4 may have the same shape and size or different shapes and sizes. Each of the table mounting unit 310 and the stand mounting unit 320 may be divided into four virtual regions to correspond to shapes and sizes of A1, A2, A3, and A4. The table mounting unit 310 may be divided into four regions B1, B2, B3, and B4, and the stand mounting unit 320 may be divided into four regions C1, C2, C3, and C4.

The magnet may be mounted in the table mounting unit 310 and the stand mounting unit 320. The magnet of the table mounting unit 310 and the magnet of the stand mounting unit 320 may be mounted in different regions. One of the magnet of the table mounting unit 310 and the magnet of the stand mounting unit 320 may be provided in a region or a position corresponding to the first sensor group, and the other magnet may be provided in a region or a position corresponding to the second sensor group. As exemplified in FIGS. 23B and 23C, the magnet of the table mounting unit 310 may be provided in the region B2, and the magnet of the stand mounting unit 320 may be provided in the region C3. The magnet of the table mounting unit 310 may be provided to correspond to a center position of the first sensor group, and the magnet of the stand mounting unit 320 may be provided to correspond to a center position of the second sensor group.

The magnet of the table mounting unit 310 and the magnet of the stand mounting unit 320 may be aligned by the same polarity. Each of the magnet of the table mounting unit 310 and the magnet of the stand mounting unit 320 may be aligned by an S pole or an N pole.

Accordingly, the first sensor group and the second sensor group detect different magnetic fields according to a mounting position of the X-ray detector 100.

A magnetic field strength detected by the first sensor group and a magnetic field strength detected by the second sensor group become different according to whether the X-ray detector 100 is mounted in the table mounting unit 310 or in the stand mounting unit 320. When the X-ray detector 100 is mounted in the table mounting unit 310 as in FIG. 23D, the first sensor group of M11, M12, M13, and M14 detects a magnetic field that is relatively greater than that of the second sensor group of M21, M22, M23, and M24. On the other hand, when the X-ray detector 100 is mounted in the stand mounting unit 320 as in FIG. 23E, the second sensor group of M21, M22, M23, and M24 detects a magnetic field that is relatively greater than that of the first sensor group of M11, M12, M13, and M14.

Also, a magnetic field direction detected by the first sensor group and a magnetic field direction detected by the second sensor group become different according to whether the X-ray detector 100 is mounted in the table mounting unit 310 or in the stand mounting unit 320. When the X-ray detector 100 is mounted in the table mounting unit 310, among the first sensor group, the sensor M11 detects (x, y, z)=(+, −, +), the sensor M12 detects (x, y, z)=(−, −, +), the sensor M13 detects (x, y, z)=(+, +, +), and the sensor M14 detects (x, y, z)=(−, +, +), as illustrated in FIG. 24A. All sensors M21, M22, M23, and M24 of the second sensor group detect (x, y, z)=(+, +, +). On the other hand, when the X-ray detector 100 is mounted in the stand mounting unit 320, all sensors M11, M12, M13, and M14 of the first sensor group detect (x, y, z)=(−, −, +), and among the second sensor group, the sensor M21 detects (x, y, z)=(+, −, +), the sensor M22 detects (x, y, z)=(−, −, +), the sensor M23 detects (x, y, z)=(+, +, +), and the sensor M24 detects (x, y, z)=(−, +, +), as illustrated in FIG. 24B.

Similarly, when the plurality of X-ray detectors 100 exemplified in FIG. 23 are provided, the plurality of sensor groups of the X-ray detector 100 implemented in a table type and the plurality of sensor groups of the X-ray detector 100 implemented in a stand type detect different magnetic field directions and different magnetic field strengths.

The control unit 250 to be described may determine a mounting position of the X-ray detector 100 using a magnetic field direction or a magnetic field strength detected by the plurality of sensor groups in this manner. When the X-ray detector 100 is mounted, a sensor value of each sensor group may be stored in the detector storage unit 170 temporarily or non-temporarily.

FIGS. 25A, 25B, 25C, 25D, 25E, 25F and 25G ("FIG. 25") are diagrams illustrating another example of the detector detecting unit including the grouped linear magnetic sensors. FIGS. 26A to 26C are diagrams illustrating a magnetic field detected by the linear magnetic sensor of FIG. 25.

As illustrated in FIG. 25, the X-ray imaging apparatus 1 may further include the portable mounting unit 330 in addition to the table mounting unit 310 and the stand mounting unit 320.

The detector detecting unit 140 of the X-ray detector 100 includes the plurality of linear magnetic sensors M11, M12, M13, M14, M21, M22, M23, and M24 as illustrated in FIG. 23A. The plurality of linear magnetic sensors M11, M12, M13, M14, M21, M22, M23, and M24 may be grouped as a first sensor group of M11, M12, M13, and M14 and a second sensor group of M21, M22, M23, and M24.

Also, four virtual regions A1, A2, A3, and A4 of the X-ray detector 100, and four regions B1, B2, B3, and B4 of the table mounting unit 310 and four regions C1, C2, C3, and C4 of the stand mounting unit 320, which are defined to correspond thereto, are the same as those in FIG. 23. Similarly, the portable mounting unit 310 may be divided into four virtual regions to correspond to shapes and sizes of A1, A2, A3, and A4, and the four regions of the portable mounting unit 330 may be defined as E1, E2, E3, and E4.

The magnet may be mounted in the table mounting unit 310, the stand mounting unit 320, and the portable mounting unit 330. The magnet of the table mounting unit 310, the magnet of the stand mounting unit 320, and the magnet of the portable mounting unit 330 may be mounted in different regions or different positions. As exemplified in FIGS. 25B, 25C and 25D, the magnet of the table mounting unit 310 may be provided in the region B2, the magnet of the stand mounting unit 320 may be provided in the region C3, and the magnet of the portable mounting unit 330 may be provided in the region E3. The magnet of the table mounting unit 310 may be provided to correspond to a center position of the first sensor group, the magnet of the stand mounting unit 320 may be provided to correspond to a center position of the second sensor group, and the magnet of the portable mounting unit 330 may be provided below the second sensor group. In this case, each of the magnet of the table mounting unit 310, the magnet of the stand mounting unit 320, and the magnet of the portable mounting unit 330 may be aligned by the same polarity.

Accordingly, the first sensor group and the second sensor group detect different magnetic fields according to a mounting position of the X-ray detector 100.

A magnetic field strength detected by the first sensor group and a magnetic field strength detected by the second sensor group become different according to whether the X-ray detector 100 is mounted in the table mounting unit 310, in the stand mounting unit 320, or in the portable mounting unit 330. When the X-ray detector 100 is mounted in the table mounting unit 310 as in FIG. 25E, the first sensor group of M11, M12, M13, and M14 detects a magnetic field that is relatively greater than that of the second sensor group of M21, M22, M23, and M24. When the X-ray detector 100 is mounted in the stand mounting unit 320 or in the portable mounting unit 330 as in FIG. 25F or 25G, the second sensor group of M21, M22, M23, and M24 detects a magnetic field that is relatively greater than that of the first sensor group of M11, M12, M13, and M14.

Also, a magnetic field direction detected by the first sensor group and a magnetic field direction detected by the second sensor group become different according to whether the X-ray detector 100 is mounted in the table mounting unit 310, in the stand mounting unit 320, or in the portable mounting unit 330. When the X-ray detector 100 is mounted in the table mounting unit 310, among the first sensor group, the sensor M11 detects (x, y, z)=(+, −, +), the sensor M12 detects (x, y, z)=(−, −, +), the sensor M13 detects (x, y, z)=(+, +, +), and the sensor M14 detects (x, y, z)=(−, +, +), and all sensors M21, M22, M23, and M24 of the second sensor group detect (x, y, z)=(+, +, +), as illustrated in FIG. 26A. When the X-ray detector 100 is mounted in the stand mounting unit 320, all sensors M11, M12, M13, and M14 of the first sensor group detect (x, y, z)=(−, −, +), and among the second sensor group, the sensor M21 detects (x, y, z)=(+, −, +), the sensor M22 detects (x, y, z)=(−, −, +), the sensor M23 detects (x, y, z)=(+, +, +), and the sensor M24 detects (x, y, z)=(−, +, +), as illustrated in FIG. 26B. When the X-ray detector 100 is mounted in the portable mounting unit 330, all sensors M11, M12, M13, and M14 of the first sensor group detect (x, y, z)=(−, −, +), and among the second sensor group, the sensor M21 detects (x, y, z)=(+, +, +), the sensor M22 detects (x, y, z)=(−, −, +), the sensor M23 detects (x, y, z)=(+, +, +), and the sensor M24 detects (x, y, z)=(−, −, +), as illustrated in FIG. 26C.

Similarly, when the plurality of X-ray detectors 100 exemplified in FIG. 25 are provided, the plurality of sensor groups of the X-ray detector 100 implemented in a table type, the plurality of sensor groups of the X-ray detector 100 implemented in a stand type, or the plurality of sensor groups of the X-ray detector 100 implemented in a portable type detect different magnetic field directions and different magnetic field strengths.

FIGS. 27A, 27B, 27C, 27D and 27E ("FIG. 27") are diagrams illustrating still another example of the detector detecting unit including the grouped linear magnetic sensors. FIGS. 28A and 28B are diagrams illustrating a magnetic field detected by the linear magnetic sensor of FIG. 27.

As illustrated in FIG. 27, the detector detecting unit 140 of the X-ray detector 100, and four virtual regions A1, A2, A3, and A4 of the X-ray detector 100 are the same as those in FIG. 23A. Also, four regions B1, B2, B3, and B4 of the table mounting unit 310 and four regions C1, C2, C3, and C4 of the stand mounting unit 320, which are defined to correspond to the regions A1, A2, A3, and A4, are the same as those in FIG. 13.

The magnet may be mounted in the table mounting unit 310 and the stand mounting unit 320. The magnet of the table mounting unit 310 and the magnet of the stand mounting unit 320 may be mounted in different regions. As exemplified in FIGS. 27B and 27C, the magnet of the table mounting unit 310 may be provided in the region B2 and the magnet of the stand mounting unit 320 may be provided in the region C3. The magnet of the table mounting unit 310 may be provided to be positioned at the right of the first sensor group, and the magnet of the stand mounting unit 320 may be provided to be positioned at the right of the second sensor group. Also, each of the magnet of the table mounting unit 310 and the magnet of the stand mounting unit 320 may be aligned by the same polarity.

Accordingly, a magnetic field strength detected by the first sensor group and a magnetic field strength detected by the second sensor group become different according to a mounting position of the X-ray detector 100. When the X-ray detector 100 is mounted in the table mounting unit 310 as in FIG. 27D, the first sensor group of M11, M12, M13, and M14 may detect a magnetic field that is relatively greater than that of the second sensor group of M21, M22, M23, and M24. On the other hand, when the X-ray detector 100 is mounted in the stand mounting unit 320 as in FIG. 27E, the second sensor group of M21, M22, M23, and M24 may detect a magnetic field that is relatively greater than that of the first sensor group of M11, M12, M13, and M14.

Also, a magnetic field direction detected by the first sensor group and a magnetic field direction detected by the second sensor group become different according to a mounting position of the X-ray detector 100. When the X-ray detector 100 is mounted in the table mounting unit 310, among the first sensor group, the sensor M11 detects (x, y, z)=(+, −, +), the sensor M12 detects (x, y, z)=(+, −, +), the sensor M13 detects (x, y, z)=(+, +, +), and the sensor M14 detects (x, y, z)=(+, +, +), and all sensors M21, M22, M23, and M24 of the second sensor group detect (x, y, z)=(+, +, +), as illustrated in FIG. 28A. On the other hand, when the X-ray detector 100 is mounted in the stand mounting unit 320, all sensors M11, M12, M13, and M14 of the first sensor group detect (x, y, z)=(−, −, +), and among the second sensor group, the sensor M21 detects (x, y, z)=(+, −, +), the sensor M22 detects (x, y, z)=(+, −, +), the sensor M23 detects (x, y, z)=(+, +, +), and the sensor M24 detects (x, y, z)=(+, +, +), as illustrated in FIG. 28B.

Similarly, when the plurality of X-ray detectors 100 exemplified in FIG. 27 are provided, the plurality of sensor groups of the X-ray detector 100 implemented in a table type and plurality of sensor groups of the X-ray detector 100 implemented in a stand type detect different magnetic field directions and different magnetic field strengths.

Figure 29A:
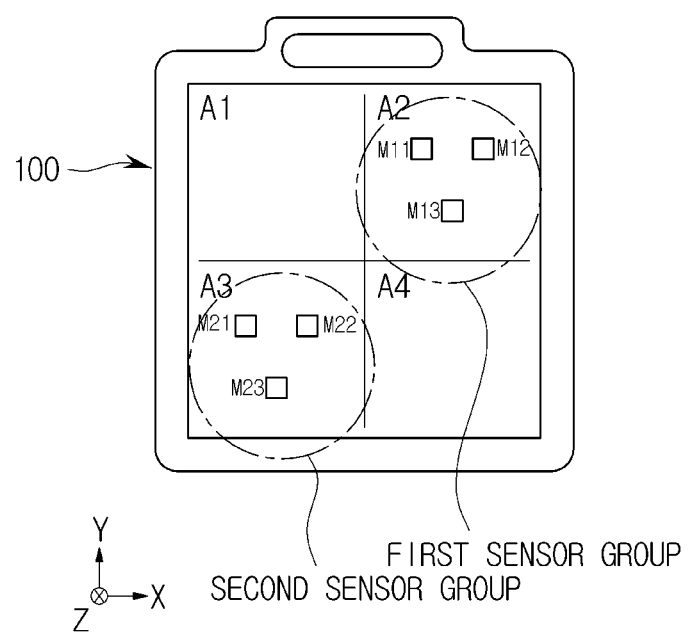
FIGS. 29A, 29B and 29C are diagrams illustrating still another example of the detector detecting unit including the grouped linear magnetic sensors.
Figure 29B:
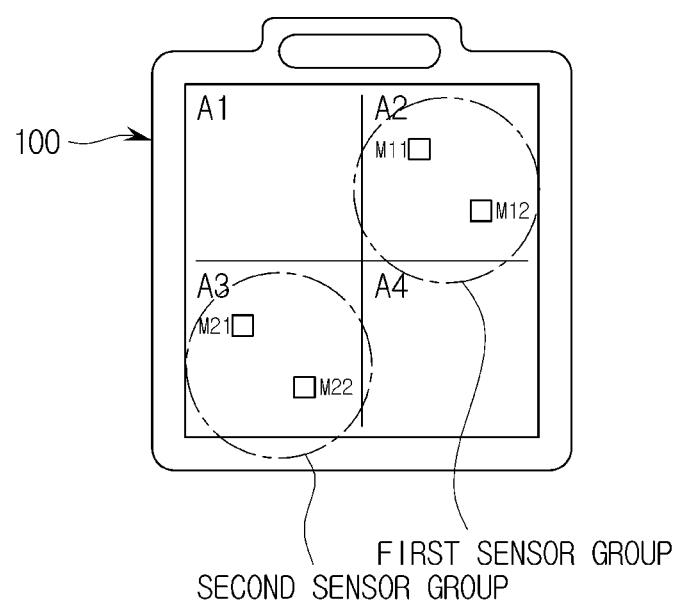
Figure 29C:
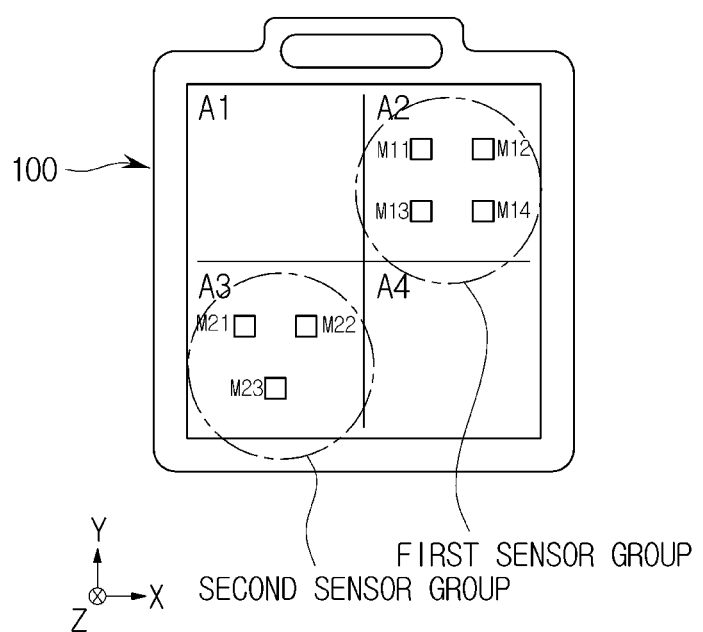

FIGS. 29A, 29B and 29C ("FIG. 29") are diagrams illustrating still another example of the detector detecting unit including the grouped linear magnetic sensors.

The detector detecting unit 140 of the X-ray detector 100 includes a plurality of linear magnetic sensors M11, M12, M13, M21, M22, and M23 as exemplified in FIG. 29A. The plurality of linear magnetic sensors M11, M12, M13, M21, M22, and M23 may be grouped as a first sensor group of M11, M12, and M13 and a second sensor group of M21, M22, and M23. Also, the detector detecting unit 140 of the X-ray detector 100 includes a plurality of linear magnetic sensors M11, M12, M21, and M22 as exemplified in FIG. 29B. The plurality of linear magnetic sensors M11, M12, M21, and M22 may be grouped as a first sensor group of M11 and M12 and a second sensor group of M21 and M22. That is, the number of linear magnetic sensors of the detector detecting unit 140 and the number of linear magnetic sensors of each sensor group may be different.

Also, the number of linear magnetic sensors of each sensor group may differ for each sensor group. As exemplified in FIG. 29C, the first sensor group may include the linear magnetic sensors M11, M12, M13, and M14, and the second sensor group may include the linear magnetic sensors M21, M22, and M23.

Figure 30A:
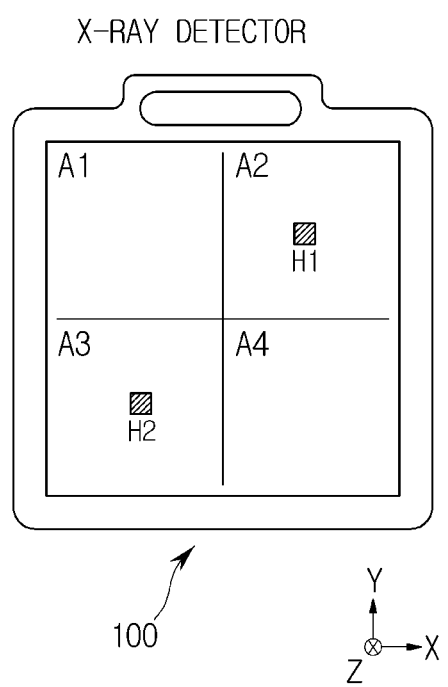
FIGS. 30A, 30B and 30C are diagrams illustrating an example of a detector detecting unit including a non-linear magnetic sensor.
Figure 30B:
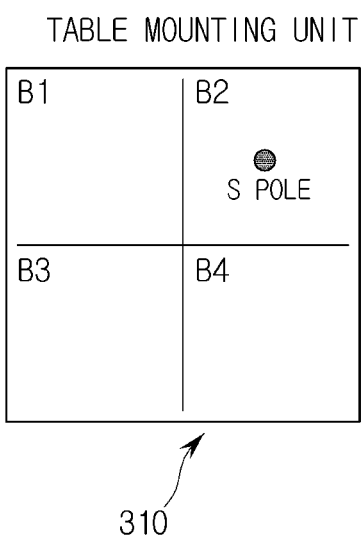
Figure 30C:
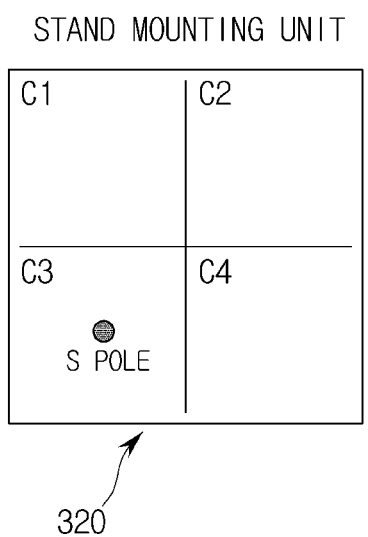
Figure 31A:
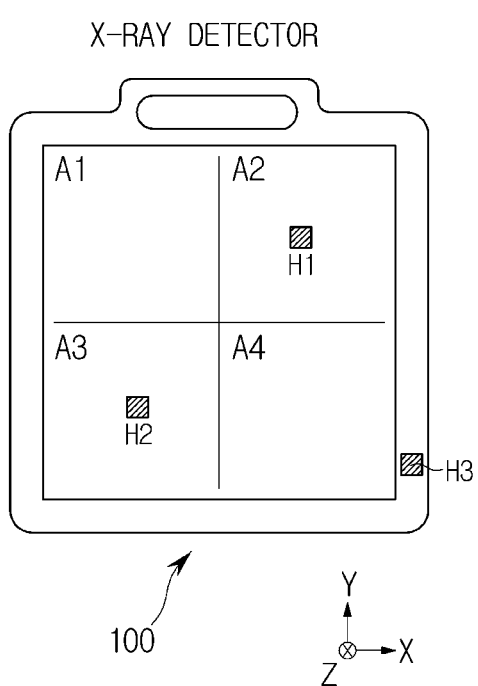
FIGS. 31A, 31B, 31C and 31D are diagrams illustrating another example of the detector detecting unit including the non-linear magnetic sensor.
Figure 31B:
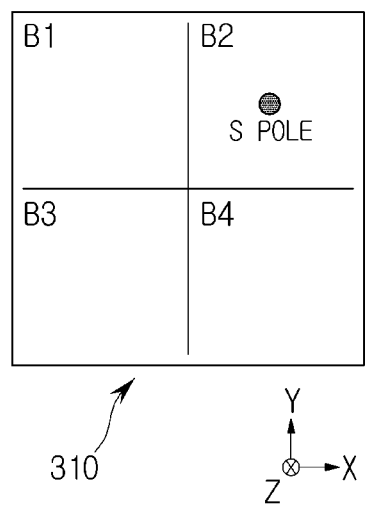
Figure 31C:
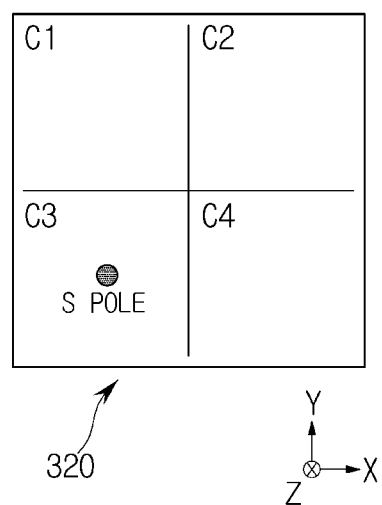
Figure 31D:
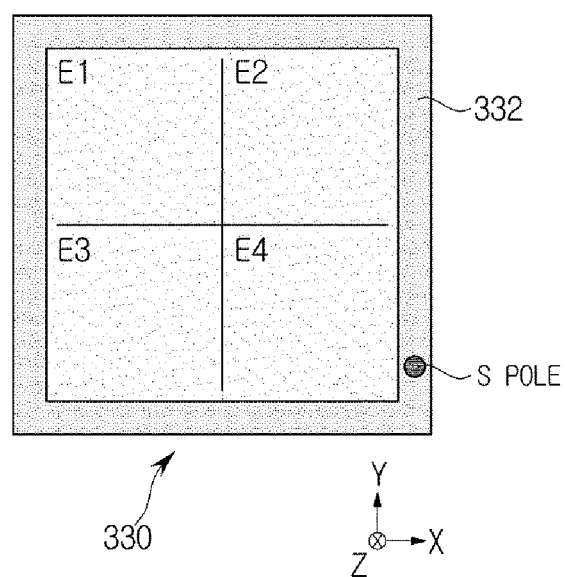

FIGS. 30A, 30B and 30C ("FIG. 30") are diagrams illustrating an example of a detector detecting unit including a non-linear magnetic sensor.

As illustrated in FIG. 30A, the X-ray detector 100 may include the detector detecting unit 140 having two nonlinear magnetic sensors H1 and H2. In this case, the two nonlinear magnetic sensors H1 and H2 may be a predetermined distance from each other. While the single X-ray detector 100 is exemplified in FIG. 30, the plurality of X-ray detectors 100 may be provided. In this case, all of the X-ray detectors 100 may include the same number of nonlinear magnetic sensors H1 and H2 at the same positions.

The two nonlinear magnetic sensors may be distinguished as the first nonlinear magnetic sensor H1 and the second nonlinear magnetic sensor H2. The X-ray detector 100 may be divided into a plurality of virtual regions, for example, regions A1, A2, A3, and A4, such that the first nonlinear magnetic sensor H1 and the second nonlinear magnetic sensor H2 are separated. A1, A2, A3, and A4 may have the same shape and size or different shapes and sizes. The table mounting unit 310 may be divided into regions B1, B2, B3, and B4 and the stand mounting unit 320 may be divided into regions C1, C2, C3, and C4 to correspond to shapes and sizes of A1, A2, A3, and A4.

The magnet may be mounted in the table mounting unit 310 and the stand mounting unit 320. The magnet of the table mounting unit 310 and the magnet of the stand mounting unit 320 may be mounted in different regions. One of the magnet of the table mounting unit 310 and the magnet of the stand mounting unit 320 may be provided in a region or a position corresponding to the first nonlinear magnetic sensor H1, and the other magnet may be provided in a region or a position corresponding to the second nonlinear magnetic sensor H2. As exemplified in FIGS. 30B and 30C, the magnet of the table mounting unit 310 may be provided in the region B2, and the magnet of the stand mounting unit 320 may be provided in the region C3. The magnet of the table mounting unit 310 may be provided to correspond to a position of the first nonlinear magnetic sensor H1, and the magnet of the stand mounting unit 320 may be provided to correspond to a position of the second nonlinear magnetic sensor H2.

The magnet of the table mounting unit 310 and the magnet of the stand mounting unit 320 may be aligned by the same polarity. Each of the magnet of the table mounting unit 310 and the magnet of the stand mounting unit 320 may be aligned by an S pole or an N pole.

Accordingly, the nonlinear magnetic sensors H1 and H2 detect different magnetic fields according to a mounting position of the X-ray detector 100. The first nonlinear magnetic sensor H1 and the second nonlinear magnetic sensor H2 output on or off according to whether the X-ray detector 100 is mounted in the table mounting unit 310 or in the stand mounting unit 320. When the X-ray detector 100 is mounted in the table mounting unit 310, the first nonlinear magnetic sensor H1 detecting a magnetic field of a threshold value or greater outputs on, and the second nonlinear magnetic sensor H2 outputs off. On the other hand, when the X-ray detector 100 is mounted in the stand mounting unit 320, the second nonlinear magnetic sensor H2 detecting a magnetic field of a threshold value or greater outputs on, and the first nonlinear magnetic sensor outputs off.

Similarly, when the plurality of X-ray detectors 100 exemplified in FIG. 30 are provided, the nonlinear magnetic sensors H1 and H2 of the X-ray detector 100 implemented in a table type and the nonlinear magnetic sensors H1 and H2 of the X-ray detector 100 implemented in a stand type detect different magnetic fields.

The control unit 250 to be described may determine a mounting position of the X-ray detector 100 using the magnetic field detected by the nonlinear magnetic sensors H1 and H2 in this manner. When the X-ray detector 100 is mounted, sensor values of the nonlinear magnetic sensors H1 and H2 may be stored in the detector storage unit 170 temporarily or non-temporarily. Also, FIG. 30 exemplifies only a configuration of the nonlinear magnetic sensor, and the number of nonlinear magnetic sensors or a position thereof is not limited thereto.

FIGS. 31A, 31B, 31C and 31D ("FIG. 31") are diagrams illustrating another example of the detector detecting unit including the non-linear magnetic sensor. As illustrated in FIG. 31, the X-ray imaging apparatus 1 may further include the portable mounting unit 330 in addition to the table mounting unit 310 and the stand mounting unit 320.

The X-ray detector 100 may include the detector detecting unit 140 including three nonlinear magnetic sensors H1, H2, and H3. In this case, the three nonlinear magnetic sensors H1, H2, and H3 may be a predetermined distance from each other. For example, the detector detecting unit 140 includes the above-described first nonlinear magnetic sensor H1 and second linear magnetic sensor H2, and may include another nonlinear magnetic sensor H3 that is separated from the first nonlinear magnetic sensor H1 and the second linear magnetic sensor H2. In this case, the nonlinear magnetic sensor H3 may be called a third nonlinear magnetic sensor. When the plurality of X-ray detectors 100 are provided, all of the X-ray detectors 100 may have the same number of nonlinear magnetic sensors H1, H2, and H3 at the same positions.

The X-ray detector 100 may be divided into a plurality of virtual regions, for example, regions A1, A2, A3, and A4, such that the first nonlinear magnetic sensor H1, the second nonlinear magnetic sensor H2, and the third nonlinear magnetic sensor H3 are separated. A1, A2, A3, and A4 may have the same shape and size or different shapes and sizes. The table mounting unit 310 may be divided into regions B1, B2, B3, and B4, the stand mounting unit 320 may be divided into regions C1, C2, C3, and C4, and the portable mounting unit 330 may be divided into regions E1, E2, E3, and E4 to correspond to shapes and sizes of A1, A2, A3, and A4.

The magnet may be mounted in the table mounting unit 310, the stand mounting unit 320, and the portable mounting unit 330. The magnet of the table mounting unit 310, the magnet of the stand mounting unit 320, and the magnet of the portable mounting unit 330 may be mounted in different regions. As exemplified in FIGS. 31B, 31c and 31D, the magnet of the table mounting unit 310 may be provided in the region B2, the magnet of the stand mounting unit 320 may be provided in the region C3, and the magnet of the portable mounting unit 330 may be provided in the region E4. The magnet of the table mounting unit 310 may be provided to correspond to a position of the first nonlinear magnetic sensor H1, the magnet of the stand mounting unit 320 may be provided to correspond to a position of the second nonlinear magnetic sensor H2, and the magnet of the portable mounting unit 330 may be provided to correspond to a position of the third nonlinear magnetic sensor H3. Also, each of the magnet of the table mounting unit 310, the magnet of the stand mounting unit 320, and the magnet of the portable mounting unit 330 may be aligned by the same polarity.

Accordingly, the three nonlinear magnetic sensors H1, H2, and H3 detect different magnetic fields according to a mounting position of the X-ray detector 100. The first nonlinear magnetic sensor H1, the second nonlinear magnetic sensor H2, and the third nonlinear magnetic sensor H3 output on or off according to whether the X-ray detector 100 is mounted in the table mounting unit 310, in the stand mounting unit 320, or in the portable mounting unit 330.

When the X-ray detector 100 is mounted in the table mounting unit 310, the first nonlinear magnetic sensor H1 detecting a magnetic field of a threshold value or greater outputs on, and the second nonlinear magnetic sensor H2 and the third nonlinear magnetic sensor H3 output off. When the X-ray detector 100 is mounted in the stand mounting unit 320, the second nonlinear magnetic sensor H2 detecting a magnetic field of a threshold value or greater outputs on, and the first nonlinear magnetic sensor H1 and the third nonlinear magnetic sensor H3 output off. Also, when the X-ray detector 100 is mounted in the portable mounting unit 330, the third nonlinear magnetic sensor H3 detecting a magnetic field of a threshold value or greater outputs on, and the first nonlinear magnetic sensor H1 and the second nonlinear magnetic sensor H2 output off.

Similarly, when the plurality of X-ray detectors 100 exemplified in FIG. 31 are provided, the nonlinear magnetic sensors H1, H2, and H3 of the X-ray detector 100 implemented in a table type, the nonlinear magnetic sensors H1, H2, and H3 of the X-ray detector 100 implemented in a stand type, or the nonlinear magnetic sensors H1, H2, and H3 of the X-ray detector 100 implemented in a portable type detect different magnetic fields.

Figure 32:
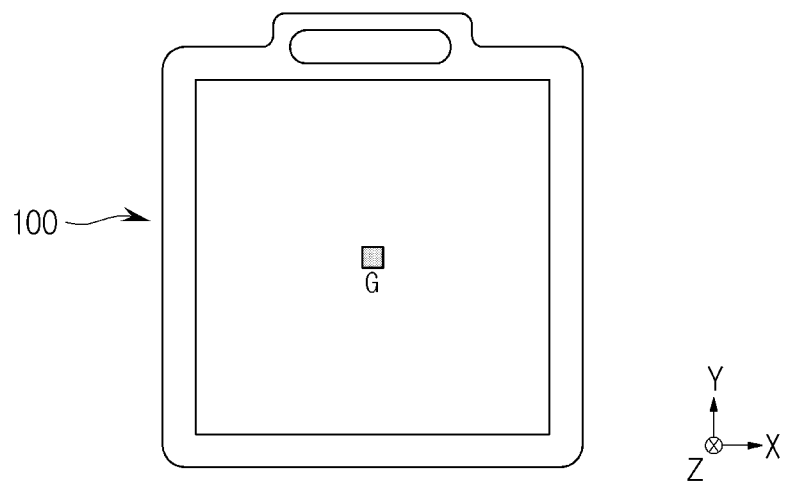
FIG. 32 is a diagram illustrating an example of a detector detecting unit including a tilt sensor.

FIG. 32 is a diagram illustrating an example of a detector detecting unit including a tilt sensor.

The X-ray detector 100 may include the detector detecting unit 140 having a tilt sensor G. While a configuration of the single tilt sensor G is exemplified in FIG. 32, the number of tilt sensors G or a position thereof is not limited thereto, as long as a tilt or a degree of a tilt of the X-ray detector 100 may be detected. Also, while the single X-ray detector 100 is exemplified in FIG. 32, the plurality of X-ray detectors 100 may be provided. In this case, all of the X-ray detectors 100 include the detector detecting unit 140 having the same configuration.

As described in FIG. 4, the X-ray detector 100 is mounted in the table mounting unit 310 in parallel with the bottom surface. Accordingly, when the X-ray detector 100 is mounted in the table mounting unit 310, the tilt sensor G detects a horizontal state or detects a tilt about 0°.

As described in FIGS. 5A and 5B, the stand mounting unit 320 may rotate in the seventh direction D7. Accordingly, when the X-ray detector 100 is mounted in the stand mounting unit 320, the X-ray detector 100 may be mounted perpendicular to the bottom surface or mounted in parallel with the bottom surface. That is, when the X-ray detector 100 is mounted in the stand mounting unit 320, the tilt sensor G may detect a horizontal state (or may detect a tilt of about 90°), and may also detect a vertical state (or may detect a tilt of about 0°).

The control unit 250 to be described may determine a mounting position of the X-ray detector 100 using a tilt detected by the tilt sensor 252 in this manner. When the X-ray detector 100 is mounted, a sensor value of the tilt sensor G may be stored in the detector storage unit 170 temporarily or non-temporarily.

While the detector detecting unit 140 including sensors of the same type has been exemplified above, the detector detecting unit 140 may include a combination of sensors of different types.

Figure 33A:
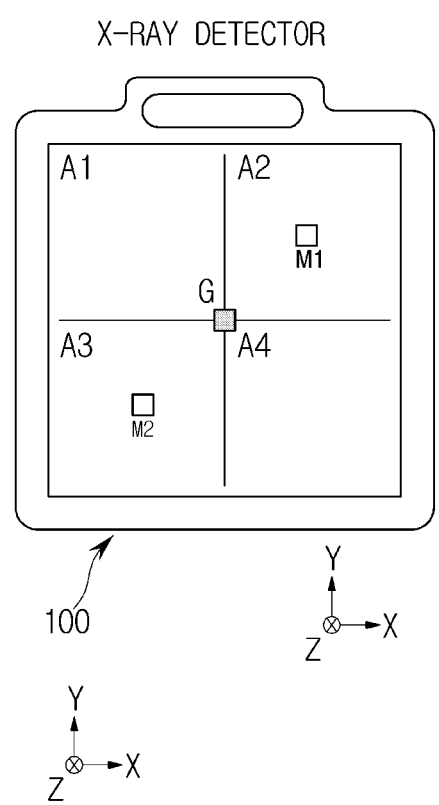
FIGS. 33A, 33B and 33C are diagrams illustrating an example of a detector detecting unit including a linear magnetic sensor and a tilt sensor.
Figure 33B:
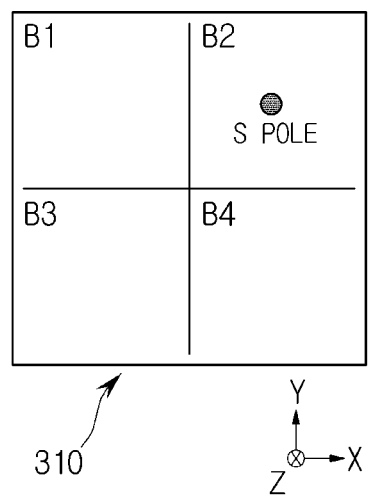
Figure 33C:
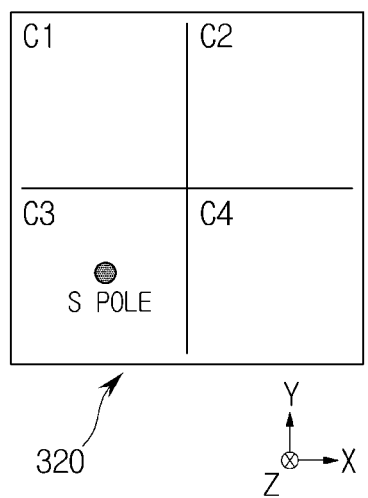

FIGS. 33A, 33B and 33C ("FIG. 33") are diagrams illustrating an example of a detector detecting unit including a linear magnetic sensor and a tilt sensor.

As illustrated in FIG. 33, the X-ray detector 100 may include the detector detecting unit 140 having a combination of two linear magnetic sensors M1 and M2 and a tilt sensor G. In this case, the two linear magnetic sensors M1 and M2 may be the same as the first linear magnetic sensor M1 and the second linear magnetic sensor M2 as described in FIG. 19. Also, the magnet may be mounted in the table mounting unit 310 and the stand mounting unit 320. For example, the magnet of the table mounting unit 310 may be mounted to correspond to a position of the first linear magnetic sensor M1, and the magnet of the stand mounting unit 320 may be mounted to correspond to a position of the second linear magnetic sensor M2. The magnet of the table mounting unit 310 and the magnet of the stand mounting unit 320 may be aligned by the same polarity, for example, an S pole.

Accordingly, the detector detecting unit 140 detects a tilt through the tilt sensor G or detects a magnetic field through linear magnetic sensors M1 and M2. For example, when the X-ray detector 100 is mounted in the table mounting unit 310, the tilt sensor G detects a horizontal state or detects a tilt of about 0°. Also, the first linear magnetic sensor M1 detects a magnetic field strength that is relatively greater than that of the second linear magnetic sensor M2. When the X-ray detector 100 is mounted in the stand mounting unit 320, the tilt sensor G may detect a horizontal state (or may detect a tilt of about 90°), and may also detect a vertical state (or may detect a tilt of about 0°). However, the second linear magnetic sensor M2 detects a magnetic field strength that is relatively greater than that of the first linear magnetic sensor M1. When the X-ray detector 100 is not mounted but implemented in a portable type, the first linear magnetic sensor M1 and the second linear magnetic sensor M2 do not detect a magnetic field. However, the tilt sensor G detects a predetermined tilt.

The control unit 250 to be described may determine a mounting position of the X-ray detector 100 using sensor values of the linear magnetic sensors M1 and M2 and the tilt sensor G in this manner. When the X-ray detector 100 is mounted, the sensor values of the linear magnetic sensors M1 and M2 and the tilt sensor G may be stored in the detector storage unit 170 temporarily or non-temporarily.

FIG. 33 is only an example of the detector detecting unit 140 including the linear magnetic sensor and the tilt sensor. The number of linear magnetic sensors or a position thereof, or the number of tilt sensors or a position thereof is not limited thereto. Also, when the plurality of X-ray detectors 100 are provided, all of the X-ray detectors 100 include the detector detecting unit 140 having the same configuration, that is, the detector detecting unit 140 including the linear magnetic sensor and the tilt sensor. In this case, the number of linear magnetic sensors and a position thereof may be the same.

Figure 34A:
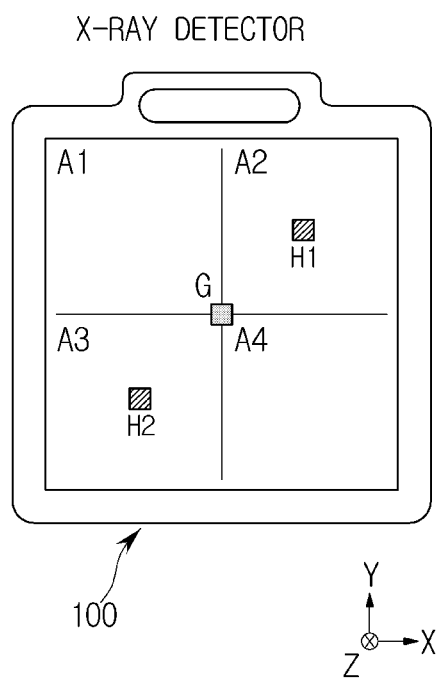
FIGS. 34A, 34B and 34C are diagrams illustrating an example of a detector detecting unit including a non-linear magnetic sensor and a tilt sensor.
Figure 34B:
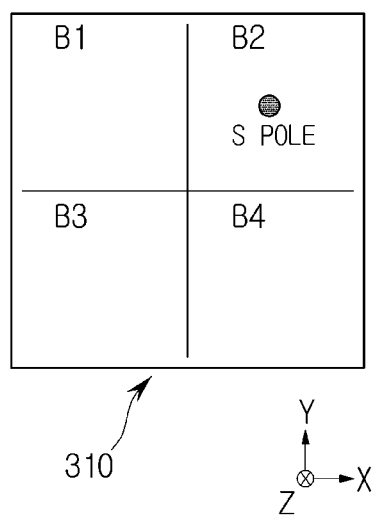
Figure 34C:
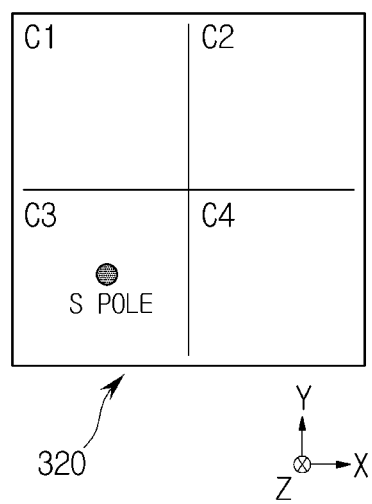

FIGS. 34A, 34B and 34C ("FIG. 34") are diagrams illustrating an example of a detector detecting unit including a non-linear magnetic sensor and a tilt sensor.

As illustrated in FIG. 34, the X-ray detector 100 may include the detector detecting unit 140 having a combination of two nonlinear magnetic sensors H1 and H2 and a tilt sensor G. In this case, the two nonlinear magnetic sensors H1 and H2 may be the same as the first nonlinear magnetic sensor H1 and the second nonlinear magnetic sensor H2 described in FIG. 30. Also, the magnet may be mounted in the table mounting unit 310 and the stand mounting unit 320. For example, the magnet of the table mounting unit 310 may be mounted to correspond to a position of the first nonlinear magnetic sensor H1, and the magnet of the stand mounting unit 320 may be mounted to correspond to a position of the second nonlinear magnetic sensor H2. The magnet of the table mounting unit 310 and the magnet of the stand mounting unit 320 may be aligned by the same polarity, for example, an S pole.

Accordingly, the detector detecting unit 140 detects a tilt through the tilt sensor G or detects a magnetic field through the nonlinear magnetic sensors H1 and H2. For example, when the X-ray detector 100 is mounted in the table mounting unit 310, the tilt sensor G detects a horizontal state or detects a tilt of about 0°. Also, the first nonlinear magnetic sensor H1 outputs on, and the second nonlinear magnetic sensor H2 outputs off. When the X-ray detector 100 is mounted in the stand mounting unit 320, the tilt sensor G may detect a horizontal state (or may detect a tilt of about 90°), and may also detect a vertical state (or may detect a tilt of about 0°). However, the second nonlinear magnetic sensor H2 outputs on, and the first nonlinear magnetic sensor H1 outputs off. When the X-ray detector 100 is not mounted but implemented in a portable type, the first nonlinear magnetic sensor M1 and the second nonlinear magnetic sensor M2 do not detect a magnetic field, but output off. However, the tilt sensor G detects a predetermined tilt.

The control unit 250 to be described may determine a mounting position of the X-ray detector 100 using sensor values of the nonlinear magnetic sensors H1 and H2 and the tilt sensor G in this manner. When the X-ray detector 100 is mounted, the sensor values of the nonlinear magnetic sensors H1 and H2 and the tilt sensor G may be stored in the detector storage unit 170 temporarily or non-temporarily.

FIG. 34 is only an example of the detector detecting unit 140 including the nonlinear magnetic sensor and the tilt sensor. The number of nonlinear magnetic sensors or a position thereof, or the number of tilt sensors or a position thereof is not limited thereto. Also, when the plurality of X-ray detectors 100 are provided, the X-ray detector 100 includes the detector detecting unit 140 having the same configuration, that is, the detector detecting unit 140 having the nonlinear magnetic sensor and the tilt sensor. In this case, the number of nonlinear magnetic sensors and a position thereof may be the same.

The detector storage unit 170 stores data and a program for operating the X-ray detector 100 temporarily or non-temporarily.

When the X-ray detector 100 is mounted, the detector storage unit 170 may store a sensor value output from the detector detecting unit 140. When the linear magnetic sensor M is included in the detector detecting unit 140, the detector storage unit 170 may store a magnetic field output from the linear magnetic sensor M, that is, a magnetic field direction or a magnetic field strength. When the nonlinear magnetic sensor H is included in the detector detecting unit 140, the detector storage unit 170 may store a magnetic field output from the nonlinear magnetic sensor H, that is, an output of on or off of the nonlinear magnetic sensor. When the tilt sensor G is included in the detector detecting unit 140, the detector storage unit 170 may store a tilt detected by the tilt sensor G.

The control unit 250 to be described may determine a position in which the X-ray detector 100 is mounted based on the sensor value in this manner, that is, a mounting position of the X-ray detector 100. Accordingly, the sensor value of the detector detecting unit 140 may be included in position information of the X-ray detector 100.

The detector storage unit 170 stores identification ("ID") information assigned to the X-ray detector 100. When the ID of the X-ray detector 100 is changed, the detector storage unit 170 stores the changed ID information. The control unit 250 to be described may determine which X-ray detector 100 is mounted or an X-ray detector 100 and a mounting position thereof based on the ID information. Detailed description thereof will be described below.

The detector storage unit 170 may include at least one type of a recording medium of a flash memory type, hard disk type, multimedia card micro type, and card type memory (for example, an SD or XD memory), a random access memory (RAM), a static random access memory (SRAM), a read-only memory (ROM), an electrically erasable programmable read-only memory (EEPROM), a programmable read-only memory (PROM), a magnetic memory, a magnetic disk, and an optical disk, but the embodiments are not limited thereto. The detector storage unit 170 may be implemented as any type known in the related art. Also, the X-ray detector 100 may operate a Web storage that performs a store function in the Internet.

The detector communication unit 160 transmits and receives various types of signals and data with the workstation 200 via wired and/or wireless communication. The detector communication unit 160 may transmit the sensor value output from the detector detecting unit 140 to the workstation 200. The detector communication unit 160 may receive ID information assigned to the X-ray detector 100 from the workstation 200. As described above, the assigned ID may be changed. When the ID of the X-ray detector 100 is changed in the workstation 200, the detector communication unit 160 may receive the changed ID information from the workstation 200.

For this purpose, the detector communication unit 160 may include various communication modules such as a wireless Internet module, a short-range communication module, and a mobile communication module.

The wireless Internet module refers to a module that is connected to an external network according to a communication protocol such as wireless LAN (WLAN), Wi-Fi, wireless broadband (Wibro), world interoperability for microwave access (Wimax), and high speed downlink packet access (HSDPA) and performs communication.

The short-range communication module refers to a module configured to perform communication with an external device located in a short-range according to a short-range communication method such as Bluetooth, radio frequency identification (RFID), Infrared Data Association (IrDA), ultra wideband (UWB), and ZigBee.

The mobile communication module refers to a module that accesses a mobile communication network according to various mobile communication standards such as 3rd generation (3G), 3rd generation partnership project (3GPP), and Long Term Evolution (LTE) and performs communication.

However, the embodiments are not limited thereto, but the detector communication unit 160 may use other types of communication modules other than the above-described modules, as long as it can communicate with the workstation 200.

Referring again to FIG. 9, the workstation 200 may include the user interface unit 210, the communication unit 260, the control unit 250, and the storage unit 270.

The control unit 250 controls overall operations of the workstation 200. The control unit 250 may control each component of the workstation 200, that is, the communication unit 260, the display unit 212, the storage unit 270, and the like.

The control unit 250 may assign or change the ID of the X-ray detector 100. The control unit 250 receives ID information and position information of the X-ray detector 100 from the X-ray detector 100, determines a mounting state and a mounting position of the X-ray detector 100 based on the ID information and position information, and may identify the mounted X-ray detector 100. In this case, the ID information includes the ID assigned to the X-ray detector 100, and the position information may include the sensor value of the detector detecting unit 140.

The control unit 250 may be various types of processors including at least one chip having an integrated circuit formed therein. The control unit 250 may be provided in a processor or separately provided in a plurality of processors.

Figure 35:
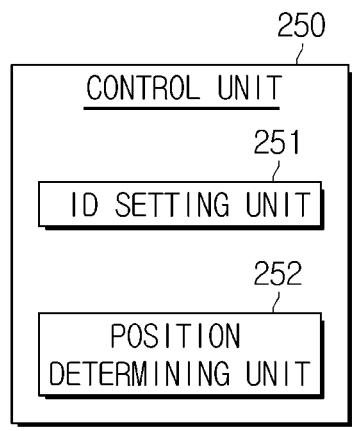
FIG. 35 is a diagram illustrating a configuration of a control unit according to an embodiment.

FIG. 35 is a diagram illustrating a configuration of a control unit according to an embodiment. As illustrated in FIG. 35, the control unit 250 may include an ID setting unit 251 and a position determining unit 252.

The ID setting unit 251 may set an ID according to usages. The ID setting unit 251 may set a table ID, a stand ID, and a portable ID. The ID setting unit 251 may set the ID based on a user input through the user interface unit 210 and may also automatically set the ID according to a system. Here, the ID may include an Internet protocol (IP) address, a media access control (MAC) address, and the like, but the embodiments are not limited thereto. The ID may include any type as long as it can identify the X-ray detector 100.

The set ID, that is, the table ID, the stand ID, and the portable ID may be stored in the storage unit 270.

The ID setting unit 251 may assign the ID to the X-ray detector 100. When the plurality of X-ray detectors 100 are provided, the ID setting unit 251 may assign the ID to each of the plurality of X-ray detectors 100. The ID assigned to the X-ray detector 100 may be stored in the storage unit 270.

The ID setting unit 251 may assign an ID based on the set ID after ID setting, or may set an ID based on the assigned ID after ID assigning. Also, ID setting and ID assigning may be performed before the X-ray detector 100 is mounted or after the X-ray detector 100 is mounted.

The ID setting unit 251 may keep or change the assigned ID according to a mounting position or an implemented type. For example, when the stand ID is assigned to the X-ray detector 100 mounted in the table mounting unit 310, the ID setting unit 251 changes the ID of the X-ray detector 100 to the table ID, and enables an object to be imaged in the imaging table 10. Further detailed description of ID changing will be described below with description of the position determining unit 252.

The position determining unit 252 may determine an X-ray detector 100 and a mounting position thereof based on ID information of the X-ray detector 100 and position information of the X-ray detector 100. In this case, the ID information includes the ID assigned to the X-ray detector 100, and the position information includes the sensor value of the detector detecting unit 140.

The position determining unit 252 may determine a mounting state and a mounting position of the X-ray detector 100 based on the position information of the X-ray detector 100 or the sensor value transmitted from the X-ray detector 100.

When the linear magnetic sensor M is included in the detector detecting unit 140, the position determining unit 252 may determine a mounting position of the X-ray detector 100 using a magnetic field detected by the linear magnetic sensor M. The position determining unit 252 may use either of or both a magnetic field direction and a magnetic field strength detected by the linear magnetic sensor M. The sensor value of the linear magnetic sensor M according to a mounting position may be stored in the storage unit 270 in advance. Here, the expression "in advance" refers to before determination by the position determining unit 252. This expression is considered to have the same meaning hereinafter.

In the examples of FIGS. 13 and 14, the storage unit 270 may store the table of FIG. 14 in advance. Accordingly, when the linear magnetic sensor M detects a magnetic field direction of (x, y, z)=(+, +, +), the position determining unit 252 determines that the X-ray detector 100 has been mounted in the table mounting unit 310. On the other hand, when the linear magnetic sensor M detects a magnetic field direction as (x, y, z)=(−, −, +), the position determining unit 252 determines that the X-ray detector 100 has been mounted in the stand mounting unit 320.

In the examples of FIGS. 15 and 16, the storage unit 270 may store the table of FIG. 16 in advance. Accordingly, when the linear magnetic sensor M detects a magnetic field direction as (x, y, z)=(+, +, +), the position determining unit 252 determines that the X-ray detector 100 has been mounted in the table mounting unit 310. When the linear magnetic sensor M detects a magnetic field direction as (x, y, z)=(−, −, +), the position determining unit 252 determines that the X-ray detector 100 has been mounted in the stand mounting unit 320. Also, when the linear magnetic sensor M detects a magnetic field direction as (x, y, z)=(+, −, +), the position determining unit 252 determines that the X-ray detector 100 has been mounted in the portable mounting unit 330.

In the example of FIG. 17, the storage unit 270 may store a sensor value of a table type as (x, y, z)=(+, +, +) and a sensor value of a stand type as (x, y, z)=(−, −, +) in advance. Accordingly, when the linear magnetic sensor M detects a magnetic field direction as (x, y, z)=(+, +, +), the position determining unit 252 determines that the X-ray detector 100 has been mounted in the table mounting unit 310. On the other hand, when the linear magnetic sensor M detects a magnetic field direction as (x, y, z)=(−, −, +), the position determining unit 252 determines that the X-ray detector 100 has been mounted in the stand mounting unit 320.

In the example of FIG. 18, the storage unit 270 may store a sensor value of a table type as (x, y, z)=(+, +, +), a sensor value of a stand type as (x, y, z)=(−, −, +), and a sensor value of a portable type as (x, y, z)=(+, −, +) in advance. Accordingly, when the linear magnetic sensor M detects a magnetic field direction as (x, y, z)=(+, +, +), the position determining unit 252 determines that the X-ray detector 100 has been mounted in the table mounting unit 310. When the linear magnetic sensor M detects a magnetic field direction as (x, y, z)=(−, −, +), the position determining unit 252 determines that the X-ray detector 100 has been mounted in the stand mounting unit 320. Also, when the linear magnetic sensor M detects a magnetic field direction as (x, y, z)=(+, −, +), the position determining unit 252 determines that the X-ray detector 100 has been mounted in the portable mounting unit 330.

The position determining unit 252 may also determine a mounting position of the X-ray detector 100 using a relative strength of a magnetic field detected by the linear magnetic sensor M.

In the example of FIG. 19, when the first linear magnetic sensor M1 detects a magnetic field strength that is relatively greater than that of the second linear magnetic sensor M2, the position determining unit 252 determines that the X-ray detector 100 has been mounted in the table mounting unit 310. On the other hand, when the second linear magnetic sensor M2 detects a magnetic field strength that is relatively greater than that of the first linear magnetic sensor M1, the position determining unit 252 determines that the X-ray detector 100 has been mounted in the stand mounting unit 320.

The position determining unit 252 may also determine a mounting position of the X-ray detector 100 using a relative strength and an absolute strength of a magnetic field detected by the linear magnetic sensor M. The linear magnetic sensor M may be affected by a factor forming the magnetic field in addition to the magnet of the mounting unit 300, that is, may be affected by an external magnetic field. Even when the X-ray detector 100 is not mounted in the table mounting unit 310 in FIG. 19, the first linear magnetic sensor M1 may detect a magnetic field that is relatively greater than that of the second linear magnetic sensor M2 due to the external magnetic field.

In order to remove an influence of the external magnetic field, the position determining unit 252 may determine a mounting position of the X-ray detector 100 by considering the absolute strength instead of comparing only a relative strength of a magnetic field. In the above-described example, even if the first linear magnetic sensor M1 detects a relatively greater magnetic field, only when the first linear magnetic sensor M1 detects a magnetic field of a predetermined threshold value or greater, the position determining unit 252 determines that the X-ray detector 100 has been mounted in the table mounting unit 310. In this case, setting of the threshold value and a resulting determining method of the position determining unit 252 will be described with reference to FIGS. 36A, 36B, 36C and 37.

Figure 36A:
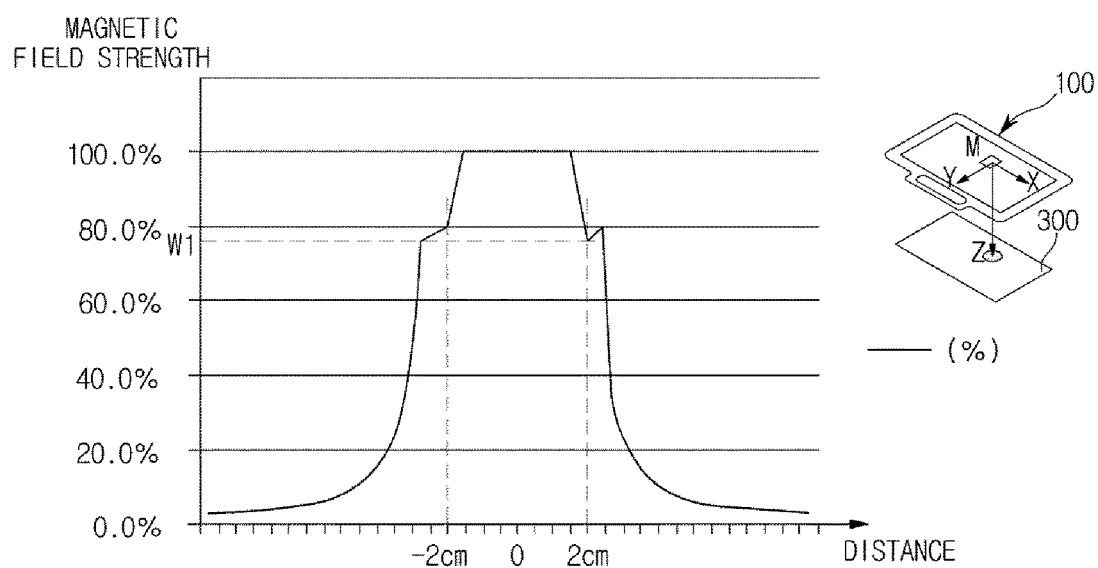
FIG. 36A to FIG. 36C are graphs illustrating an exemplary magnetic field strength detected by the linear magnetic sensor in three mutually orthogonal directions.
Figure 36B:
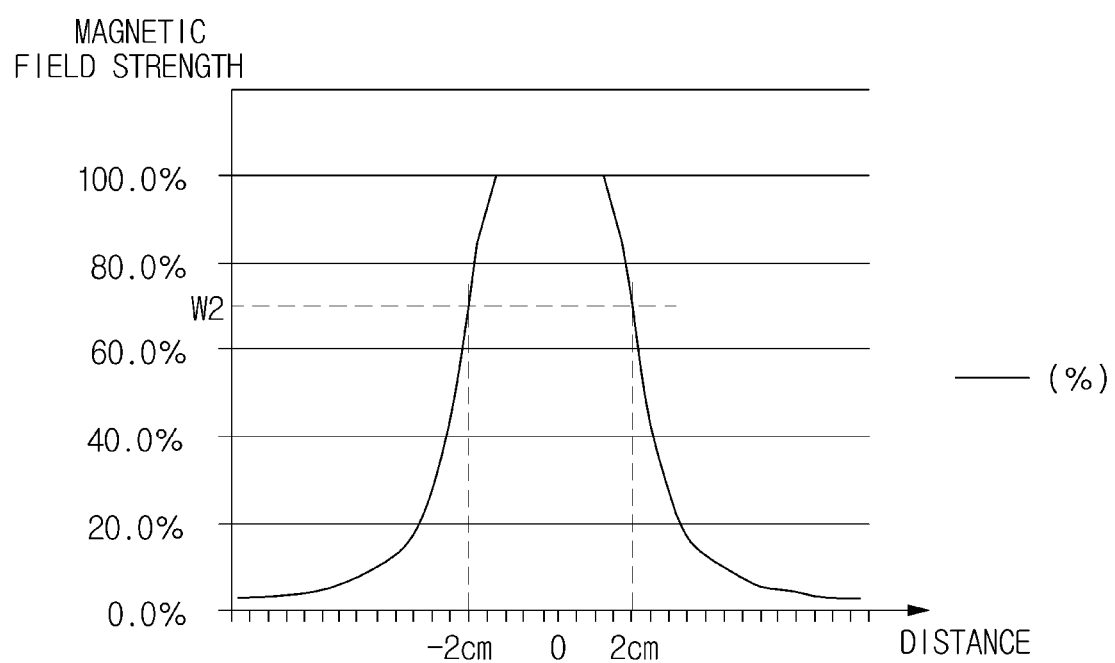
Figure 36C:
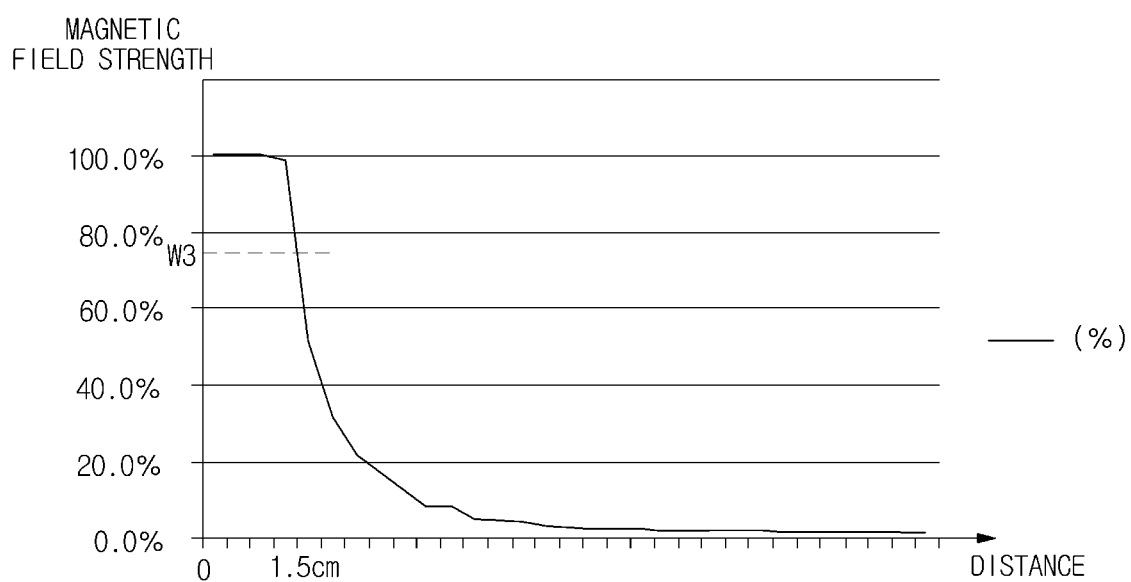

FIG. 36A to FIG. 36C are graphs illustrating an exemplary magnetic field strength detected by the linear magnetic sensor in three mutually orthogonal directions. Here, the three mutually orthogonal directions refer to x axis, y axis, and z axis directions set based on the linear magnetic sensor M. With respect to the linear magnetic sensor M, two axes, that is, an x axis and a y axis, that are perpendicular may be defined on a plane of the X-ray detector 100, and a z axis perpendicular the two axes may be defined.

FIG. 36A shows a measured value of a magnetic field strength detected by the linear magnetic sensor M while the magnet or the linear magnetic sensor M moves along only the x axis. FIG. 36B shows a measured value of a magnetic field strength detected by the linear magnetic sensor M while the magnet or the linear magnetic sensor M moves along only the y axis. Similarly, FIG. 36C shows a measured value of a magnetic field strength detected by the linear magnetic sensor M while the magnet or the linear magnetic sensor M moves along only the z axis.

A horizontal axis of the graph represents a distance between the linear magnetic sensor M and the magnet. A vertical axis of the graph represents a relative value of a magnetic field strength. Accordingly, when the linear magnetic sensor M and the magnet are provided in positions that correspond to each other, a magnetic field strength measured in each direction is 100%.

As illustrated in FIGS. 36A to 36C, a magnetic field strength detected by the linear magnetic sensor M is inversely proportional to a distance from the magnet. As the magnet becomes further from the linear magnetic sensor M in a positive direction or a negative direction of the x axis, a magnetic field strength detected by the linear magnetic sensor M decreases. In particular, the magnetic field strength is significantly changed at a reference distance of 2 cm. Similarly, as the magnet becomes further from the linear magnetic sensor M in a positive direction or a negative direction of the y axis, a magnetic field strength detected by the linear magnetic sensor M decreases. The magnetic field strength is significantly changed at a reference distance of 2 cm. Also, a magnetic field strength detected by the linear magnetic sensor M decreases as the magnet becomes further in a positive direction of the z axis. The magnetic field strength is significantly changed at a reference distance of 1.5 cm.

Accordingly, a threshold value for determining a mounting position of the X-ray detector 100 may be set using a reference distance in each direction. For example, a magnetic field strength W1 corresponding to about 2 cm is defined as an x axis reference value in FIG. 36A, a magnetic field strength W2 corresponding to 2 cm is defined as a y axis reference value in FIG. 36B, and a magnetic field strength W3 corresponding to 1.5 cm is defined as a z axis reference value in FIG. 36C. A total reference value W may be set as a sum of the reference value in each direction. Here, the x axis reference value W1, the y axis reference value W2, the z axis reference value W3, and the total reference value W may be converted into a magnetic field unit (AT/m). That is, the total reference value W=W1+W2+W3 is set, and the total reference value W becomes a threshold value for determining a mounting position of the X-ray detector 100.

The threshold value may be adjusted according to the number of linear magnetic sensors M provided in the X-ray detector 100 or a distance thereof. Conversely, the number of linear magnetic sensors M provided in the X-ray detector 100 or a distance thereof may be changed according to the threshold value.

For example, in FIG. 19, the threshold value may be set or adjusted in advance such that, when the X-ray detector 100 is mounted in the table mounting unit 310, only the first linear magnetic sensor M1 detects a magnetic field of a threshold value or greater, and when the X-ray detector 100 is mounted in the stand mounting unit 320, only the second linear magnetic sensor M2 detects a magnetic field of a threshold value or greater. Also, a distance between the first linear detect sensor M1 and the second linear detect sensor M2 may be set or adjusted in advance such that, when the X-ray detector 100 is mounted in the table mounting unit 310, only the first linear magnetic sensor M1 detects a magnetic field of a threshold value or greater, and when the X-ray detector 100 is mounted in the stand mounting unit 320, only the second linear magnetic sensor M2 detects a magnetic field of a threshold value or greater.

Accordingly, the position determining unit 252 may determine a mounting position of the X-ray detector 100 by comparing a magnetic field strength detected by the linear magnetic sensor M with the threshold value. The position determining unit 252 may determine a mounting position of the X-ray detector 100 from a position of a sensor detecting a magnetic field of a threshold value or greater.

In the example of FIG. 19 or 21, when the first linear magnetic sensor M1 detects a magnetic field of a threshold value or greater, the position determining unit 252 determines that the X-ray detector 100 has been mounted in the table mounting unit 310, and when the second linear magnetic sensor M2 detects a magnetic field of a threshold value or greater, the position determining unit 252 may determine that the X-ray detector 100 has been mounted in the stand mounting unit 320.

In the example of FIG. 20, when the first linear magnetic sensor M1 detects a magnetic field of a threshold value or greater, the position determining unit 252 determines that the X-ray detector 100 has been mounted in the table mounting unit 310, and when the second linear magnetic sensor M2 detects a magnetic field of a threshold value or greater, the position determining unit 252 may determine that the X-ray detector 100 has been mounted in the stand mounting unit 320. Also, when the third linear magnetic sensor M3 detects a magnetic field of a threshold value or greater, the position determining unit 252 may determine that the X-ray detector 100 has been mounted in the portable mounting unit 330.

In the example of FIG. 22, when the first linear magnetic sensor M1 detects a magnetic field of a threshold value or greater, the position determining unit 252 determines that the X-ray detector 100 has been mounted in the table mounting unit 310, and when the second linear magnetic sensor M2 detects a magnetic field of a threshold value or greater, the position determining unit 252 may determine that the X-ray detector 100 has been mounted in the stand mounting unit 320. Also, when the fourth linear magnetic sensor M4 detects a magnetic field of a threshold value or greater, the position determining unit 252 may determine that the X-ray detector 100 has been mounted in the portable mounting unit 330.

In the example of FIG. 23 or 27, when a sensor detecting a magnetic field of a threshold value or greater is included in the first sensor group of M11, M12, M13, and M14, the position determining unit 252 determines that the X-ray detector 100 has been mounted in the table mounting unit 310, and when a sensor detecting a magnetic field of a threshold value or greater is included in the second sensor group of M21, M22, M23, and M24, the position determining unit 252 may determine that the X-ray detector 100 has been mounted in the stand mounting unit 320.

A method of the position determining unit 252 determining a mounting position may differ according to adjustment of the threshold value. For example, in FIG. 23, the threshold value may be adjusted such that, when all sensors of the first sensor group of M11, M12, M13, and M14 detect a magnetic field of a threshold value or greater, it is determined that the X-ray detector 100 has been mounted in the table mounting unit 310, and when all sensors of the second sensor group of M21, M22, M23, and M24 detect a magnetic field of a threshold value or greater, it is determined that the X-ray detector 100 has been mounted in the stand mounting unit 320.

Figure 37A:
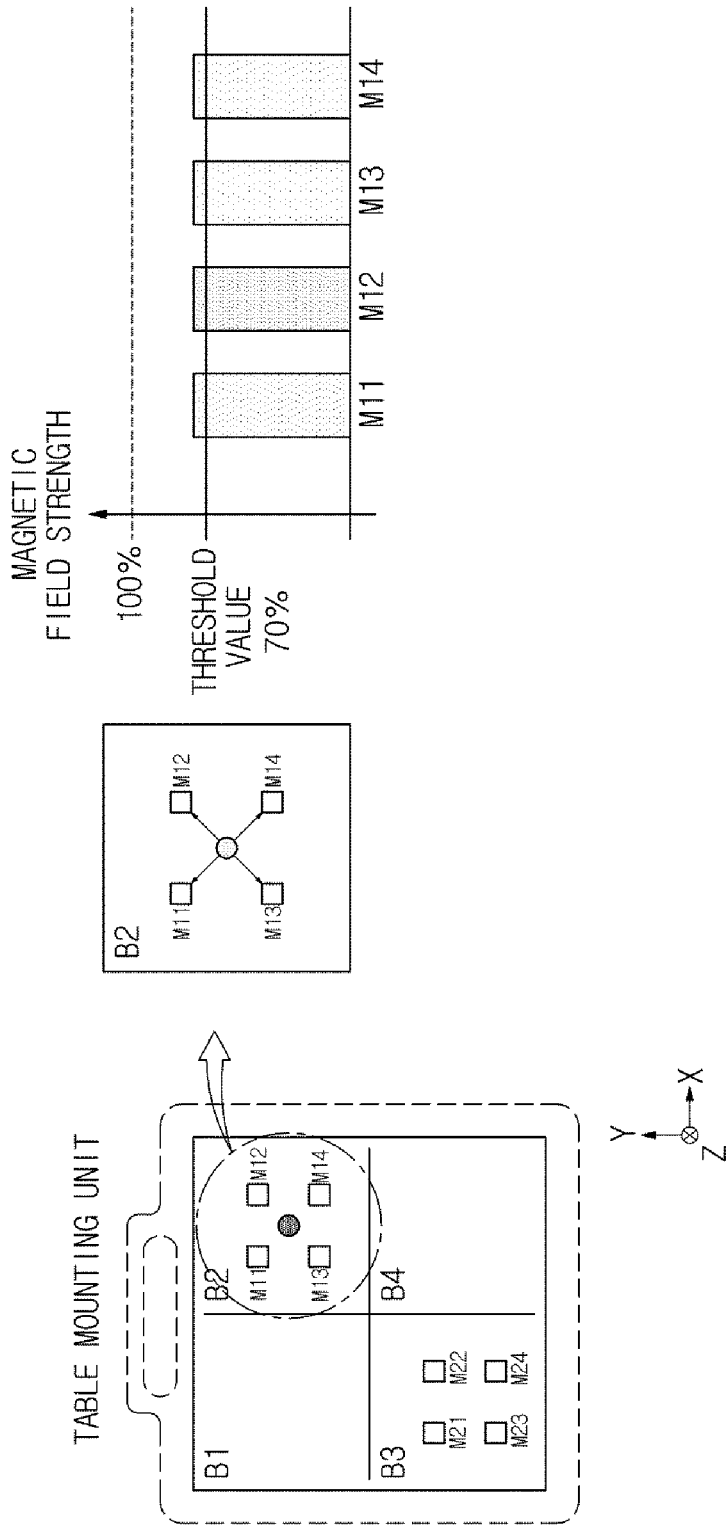
FIGS. 37A and 37B are diagrams illustrating adjustment of a threshold value according to a position of a magnet.
Figure 37B:
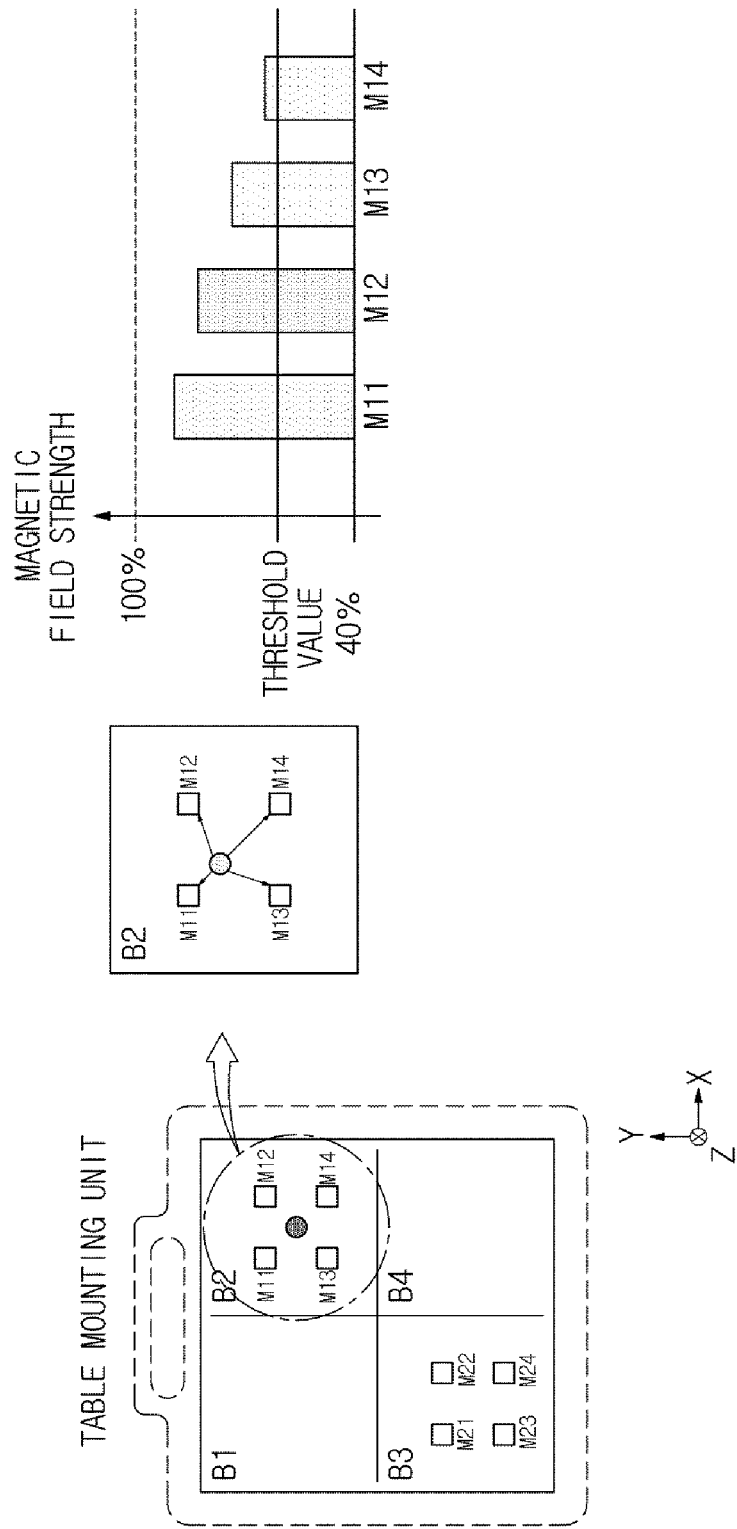

The threshold value may also be adjusted according to a position of the magnet provided in the mounting unit 300. FIGS. 37A and 37B ("FIG. 37") are diagrams illustrating adjustment of a threshold value according to a position of a magnet. FIG. 37A illustrates a state in which the X-ray detector 100 of FIG. 23 is mounted in the table mounting unit 310. FIG. 37B illustrates a state in which a position of the magnet of the table mounting unit 310 is changed due to an assembly tolerance and the like.

In FIG. 37A, the threshold value is set as a value corresponding to 70% such that, when all sensors of the first sensor group of M11, M12, M13, and M14 detect a magnetic field of a threshold value or greater, it is determined that the X-ray detector 100 has been mounted in the table mounting unit 310, and when all sensors of the second sensor group of M21, M22, M23, and M24 detect a magnetic field of a threshold value or greater, it is determined that the X-ray detector 100 has been mounted in the stand mounting unit 320.

In FIG. 37B, in order to retain a determining method that is the same as in FIG. 37A, the threshold value should be adjusted. In FIG. 37A, since the first magnet keeps the same distance with respect to all sensors of the first sensor group of M11, M12, M13, and M14, a magnetic field strength detected by each sensor becomes the same. On the other hand, in FIG. 37B, the first magnet becomes further from the sensor M14 as the first magnet becomes closer to the sensor M11. Therefore, a magnetic field strength detected by the sensor M14 becomes relatively smaller than that of the sensors M11, M12, and M13. Accordingly, the threshold value should be adjusted to a value corresponding to 40% based on the sensor M14 that is the furthest from the first magnet or detects the smallest magnetic field such that the same determining method may be applied.

The threshold value for determining a mounting position of the X-ray detector 100 may be set or adjusted through the user interface unit 210. Also, the set or adjusted threshold value may be stored in the storage unit 270 in advance before determination of the position determining unit 252.

The position determining unit 252 may determine a mounting position of the X-ray detector 100 using both a magnetic field direction and a magnetic field strength detected by the linear magnetic sensor M.

For example, in FIG. 23, when the first sensor group of M11, M12, M13, and M14 detects (x, y, z)=(+, −, +), (x, y, z)=(−, −, +), (x, y, z)=(+, +, +), and (x, y, z)=(−, +, +) according to the order of the sensors, and the first sensor group of M11, M12, M13, and M14 detects a magnetic field that is relatively greater than that of the second sensor group of M21, M22, M23, and M24, the position determining unit 252 may determine that the X-ray detector 100 has been mounted in the table mounting unit 310. On the other hand, when the second sensor group of M21, M22, M23, and M24 detects (x, y, z)=(+, −, +), (x, y, z)=(−, −, +), (x, y, z)=(+, +, +), and (x, y, z)=(−, +, +) according to the order of the sensors and the second sensor group of M21, M22, M23, and M24 detects a magnetic field that is relatively greater than that of the first sensor group of M11, M12, M13, and M14, the position determining unit 252 may determine that the X-ray detector 100 has been mounted in the stand mounting unit 320.

Also, in FIG. 25, when the first sensor group of M11, M12, M13, and M14 detects (x, y, z)=(+, −, +), (x, y, z)=(−, −, +), (x, y, z)=(+, +, +), and (x, y, z)=(−, +, +) according to the order of the sensors and the first sensor group of M11, M12, M13, and M14 detects a magnetic field that is relatively greater than that of the second sensor group of M21, M22, M23, and M24, the position determining unit 252 may determine that the X-ray detector 100 has been mounted in the table mounting unit 310. When the second sensor group of M21, M22, M23, and M24 detects (x, y, z)=(+, −, +), (x, y, z)=(−, −, +), (x, y, z)=(+, +, +), and (x, y, z)=(−, +, +) according to the order of the sensors and the second sensor group of M21, M22, M23, and M24 detects a magnetic field that is relatively greater than that of the first sensor group of M11, M12, M13, and M14, the position determining unit 252 may determine that the X-ray detector 100 has been mounted in the stand mounting unit 320. Also, when the second sensor group of M21, M22, M23, and M24 detects (x, y, z)=(+, +, +), (x, y, z)=(−, −, +), (x, y, z)=(+, +, +), and (x, y, z)=(−, −, +) according to the order of the sensors and the second sensor group of M21, M22, M23, and M24 detects a magnetic field that is relatively greater than that of the first sensor group of M11, M12, M13, and M14, the position determining unit 252 may determine that the X-ray detector 100 has been mounted in the portable mounting unit 330.

Even when both a magnetic field direction and a magnetic field strength are used, the position determining unit 252 may use an absolute strength of the magnetic field, that is, the threshold value.

For example, in FIG. 27, when the first sensor group of M11, M12, M13, and M14 detects (x, y, z)=(+, −, +), (x, y, z)=(+, −, +), (x, y, z)=(+, +, +), and (x, y, z)=(+, +, +) according to the order of the sensors and a sensor included in the first sensor group of M11, M12, M13, and M14 detects a magnetic field of a threshold value or greater, the position determining unit 252 may determine that the X-ray detector 100 has been mounted in the table mounting unit 310. On the other hand, when the second sensor group of M21, M22, M23, and M24 detects (x, y, z)=(+, −, +), (x, y, z)=(+, −, +), (x, y, z)=(+, +, +), and (x, y, z)=(+, +, +) according to the order of the sensors and a sensor included in the second sensor group of M21, M22, M23, and M24 detects a magnetic field of a threshold value or greater, the position determining unit 252 may determine that the X-ray detector 100 has been mounted in the stand mounting unit 320.

When the nonlinear magnetic sensor H is included in the detector detecting unit 140, the position determining unit 252 may determine a mounting position of the X-ray detector 100 based on an output of on or off of the nonlinear magnetic sensor H. A sensor value of the nonlinear magnetic sensor H according to a mounting position may store in the storage unit 270 in advance.

In the example of FIG. 30, when the first nonlinear magnetic sensor H1 outputs on and the second nonlinear magnetic sensor H2 outputs off, the position determining unit 252 may determine that the X-ray detector 100 has been mounted in the table mounting unit 310. On the other hand, when the second nonlinear magnetic sensor H2 outputs on and the first nonlinear magnetic sensor H1 outputs off, the position determining unit 252 may determine that the X-ray detector 100 has been mounted in the stand mounting unit 320.

In the example of FIG. 31, when the first nonlinear magnetic sensor H1 outputs on and the second nonlinear magnetic sensor H2 and the third nonlinear magnetic sensor H3 output off, the position determining unit 252 may determine that the X-ray detector 100 has been mounted in the table mounting unit 310. When the second nonlinear magnetic sensor H2 outputs on and the first nonlinear magnetic sensor H1 and the third nonlinear magnetic sensor H3 output off, the position determining unit 252 may determine that the X-ray detector 100 has been mounted in the stand mounting unit 320. Also, when the third nonlinear magnetic sensor H3 outputs on and the first nonlinear magnetic sensor H1 and the second nonlinear magnetic sensor H2 output off, the position determining unit 252 may determine that the X-ray detector 100 has been mounted in the portable mounting unit 330.

When the tilt sensor G is included in the detector detecting unit 140, the position determining unit 252 may determine a mounting position of the X-ray detector 100 using a tilt detected by the tilt sensor G. A sensor value of the tilt sensor G according to a mounting position may be stored in the storage unit 270 in advance.

As described above, when the X-ray detector 100 is mounted in the table mounting unit 310, the X-ray detector 100 is mounted in parallel with the bottom surface. However, when the X-ray detector 100 is mounted in the stand mounting unit 320, the X-ray detector 100 may be mounted perpendicular to the bottom surface or in parallel with the bottom surface.

Accordingly, if the tilt sensor G detects a vertical state (or detects a tilt of about 0°) when the X-ray detector 100 is mounted, the position determining unit 252 determines that the X-ray detector 100 has been mounted in the stand mounting unit 320. On the other hand, when the tilt sensor detects a horizontal state (or detects a tilt of about 90°), the position determining unit 252 determines a mounting position of the X-ray detector 100 after a user input. The user may input a mounting position of the X-ray detector 100 through the user interface unit 210 or the manipulation unit 80.

Figure 38A:
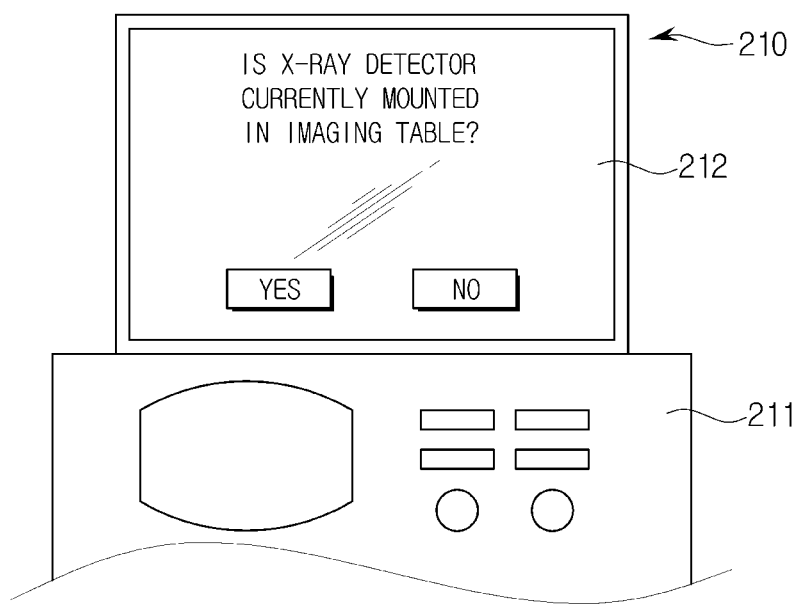
FIG. 38A is a front view of an exemplary user interface unit configured to receive a mounting position of the X-ray detector.

FIG. 38A is a front view of an exemplary user interface unit configured to receive a mounting position of the X-ray detector.

When the tilt sensor G detects a horizontal state, the position determining unit 252 may output a control signal for a user input to the user interface unit 210. The display unit 212 displays a popup window of "Is the X-ray detector currently mounted in the imaging table?" according to the control signal. When the user selects "Yes" through the input unit 211 or the display unit 212, the position determining unit 252 determines that the X-ray detector 100 has been mounted in the table mounting unit 310, and when the user selects "No," the position determining unit 252 determines that the X-ray detector 100 has been mounted in the stand mounting unit 320.

Figure 38B:
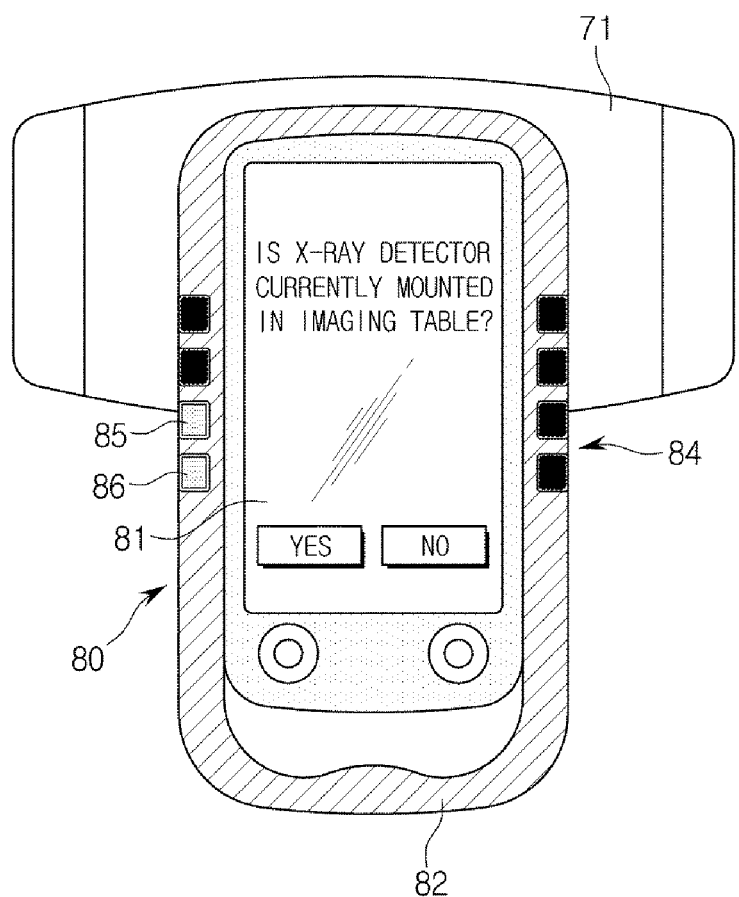
FIG. 38B is a front view of an exemplary manipulation unit configured to receive a mounting position of the X-ray detector.

FIG. 38B is a front view of an exemplary manipulation unit configured to receive a mounting position of the X-ray detector.

When the tilt sensor detects a horizontal state, the position determining unit 252 may output a control signal for a user input to the manipulation unit 80. A display panel 81 displays a popup window of "Is the X-ray detector currently mounted in the imaging table" according to the control signal. When the user selects "Yes" through the display panel 81 or the button 84, the position determining unit 252 determines that the X-ray detector 100 has been mounted in the table mounting unit 310, and when the user selects "No," the position determining unit 252 determines that the X-ray detector 100 has been mounted in the stand mounting unit 320.

In FIG. 38A or 38B, the user may also perform a selection through a terminal, a remote controller including an interface, and the like in remote. Also, when a mounting position of the X-ray detector 100 is input by the user, position information of the X-ray detector 100 may include a mounting position of the X-ray detector 100 input by the user.

When the detector detecting unit 140 includes a combination of sensors, for example, a combination of the linear magnetic sensor M and the tilt sensor G, the position determining unit 252 may determine a mounting position of the X-ray detector 100 using at least one of a magnetic field detected by the linear magnetic sensor M and a tilt detected by the tilt sensor G. A sensor value of the linear magnetic sensor M and a sensor value of the tilt sensor G according to a mounting position may be stored in the storage unit 270 in advance.

When a magnetic field detected by the linear magnetic sensor M and a tilt detected by the tilt sensor G are simultaneously used, the position determining unit 252 may determine a mounting position of the X-ray detector 100 without the user input through the user interface unit 210 or the manipulation unit 80.

As an example, in FIG. 33, even if the tilt sensor G detects a horizontal state, when the second linear magnetic sensor M2 detects a magnetic field that is relatively greater than that of the first linear magnetic sensor M1, the position determining unit 252 may determine that the X-ray detector 100 has been mounted in the stand mounting unit 320.

As another example, even if the tilt sensor G detects a horizontal state, when the second linear magnetic sensor M2 detects a magnetic field of a threshold value or greater, the position determining unit 252 may determine that the X-ray detector 100 has been mounted in the stand mounting unit 320.

Also, when a magnetic field detected by the linear magnetic sensor M and a tilt detected by the tilt sensor G are simultaneously used, the position determining unit 252 may determine whether the X-ray detector 100 is a portable type without providing the portable mounting unit 330. For example, both the first and second linear magnetic sensors M1 and M2 do not detect a magnetic field or detect a magnetic field less than a threshold value. On the other hand, when the tilt sensor G detects a predetermined tilt, the position determining unit 252 may determine that the X-ray detector 100 is a portable type.

When it is determined that the X-ray detector 100 is a portable type, the position determining unit 252 may determine a location of a desired imaging part using the tilt detected by the tilt sensor G.

FIG. 39 is a diagram illustrating determination of an imaging part. Since the portable type X-ray detector 100 is provided to move without being mounted in the imaging table 10 or the imaging stand 20, the portable type X-ray detector 100 moves on the imaging table 10 at various angles, and enables a chest or a part lower than the chest of the object to be imaged. When the part lower than the chest such as the abdomen, the pelvic region, and the lumbar region is imaged, X-ray imaging is possible while the object is lying as shown on the right in FIG. 39. The X-ray detector 100 is horizontally placed on a back of the object and imaging is performed. On the other hand, when the chest is imaged, X-ray imaging is performed while the object is in an upright state at a predetermined angle (θ) as on the left in FIG. 39 such that the heart of the object does not cover a lung. That is, imaging is performed while the X-ray detector 100 is inclined behind the back of the object at the predetermined angle (θ).

Accordingly, when the tilt sensor G detects a horizontal state (or detects about) 90°, the position determining unit 252 determines that the part lower than the chest is imaged. When the tilt sensor G detects a non-horizontal state, the position determining unit 252 may determine that the chest is imaged.

When the detector detecting unit 140 includes a combination of the nonlinear magnetic sensor H and the tilt sensor G, the position determining unit 252 may determine a mounting position of the X-ray detector 100 using at least one of an output of on or off of the nonlinear magnetic sensor H and a tilt detected by the tilt sensor G. A sensor value of the nonlinear magnetic sensor H and a sensor value of the tilt sensor G according to a mounting position may be stored in the storage unit 270 in advance.

When a magnetic field detected by the nonlinear magnetic sensor H and a tilt detected by the tilt sensor G are simultaneously used, the position determining unit 252 may determine a mounting position of the X-ray detector 100 without the user input through the user interface unit 210 or the manipulation unit 80. In the example of FIG. 34, even when the tilt sensor G detects a horizontal state, the second nonlinear magnetic sensor H2 outputs on, and when the first nonlinear magnetic sensor H1 outputs off, the position determining unit 252 may determine that the X-ray detector 100 has been mounted in the stand mounting unit 320.

Also, when a magnetic field detected by the nonlinear magnetic sensor H and a tilt detected by the tilt sensor G are simultaneously used, the position determining unit 252 may determine whether the X-ray detector 100 is a portable type without providing the portable mounting unit 330. For example, when both the first and second nonlinear magnetic sensors H1 and H2 output off, but the tilt sensor G detects a predetermined tilt, the position determining unit 252 may determine that the X-ray detector 100 is a portable type. When it is determined that the X-ray detector 100 is a portable type, the position determining unit 252 may determine a location of a desired imaging part using the tilt detected by the tilt sensor G.

As described above, the position determining unit 252 may determine a mounting position of the X-ray detector 100 based on a sensor value of the detector detecting unit 140, that is, position information of the X-ray detector 100.

The position determining unit 252 may determine an X-ray detector 100 and a mounting position thereof using position information of the X-ray detector 100 and ID information of the X-ray detector 100. The position determining unit 252 may simultaneously receive the position information of the X-ray detector 100 and the ID information of the X-ray detector 100 from the X-ray detector 100, and may determine an X-ray detector 100 and a mounting position thereof using the simultaneously received position information and ID information in this manner. Details thereof will be described with reference to FIGS. 40 and 41.

Figure 40:
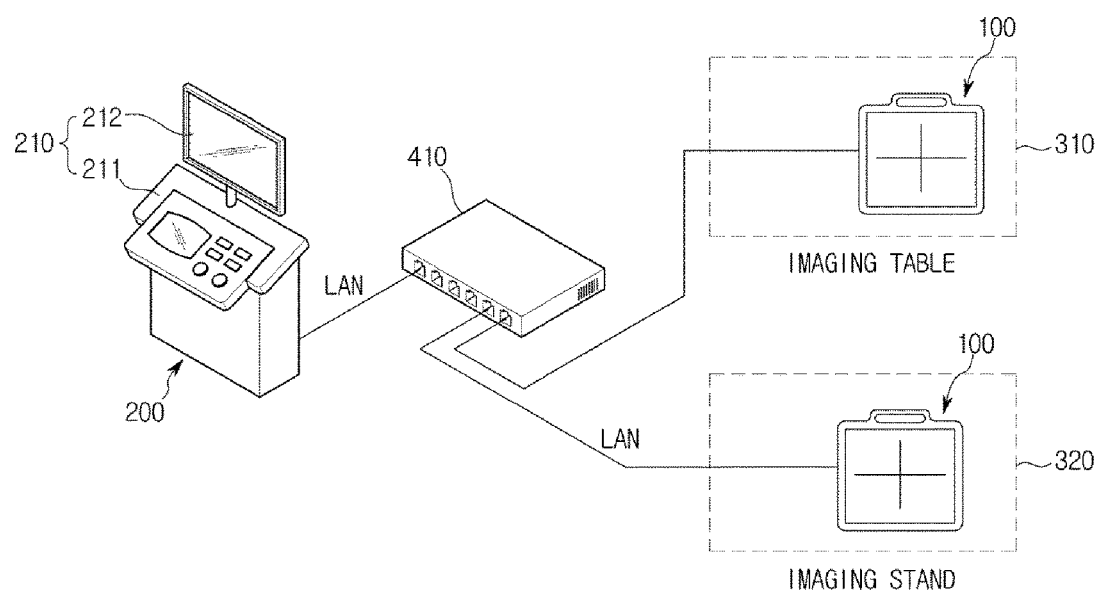
FIG. 40 is a diagram illustrating an example of a structure connecting the X-ray detector and a workstation.

FIG. 40 is a diagram illustrating an example of a structure connecting the X-ray detector and a workstation.

As described above, the plurality of X-ray detectors 100 may be provided. Each of the X-ray detectors 100 may be mounted in a different mounting unit or implemented in a different type.

As exemplified in FIG. 40, two X-ray detectors 100 are provided. One of the two X-ray detectors 100 may be mounted in the table mounting unit 310 and implemented in a table type. The other detector may be mounted in the stand mounting unit 320 and implemented in a stand type. Also, unlike the example of FIG. 40, three X-ray detectors 100 may be provided. One of the three X-ray detectors 100 may be implemented in a table type, another detector may be implemented in a stand type, and the other detector may be implemented in a portable type. In this case, the portable type X-ray detector 100 may be mounted in the portable mounting unit 330 and may also be provided without being mounted in the mounting unit 300.

Each of the plurality of X-ray detectors 100 implemented in different types is connected to the workstation 200 via the wired or wireless network 400. For example as illustrated in FIG. 40, each of the table type X-ray detector 100 and the stand type X-ray detector 100 may be connected to the workstation 200 via the wired network 400 including a cable and a network hub 410. The portable type X-ray detector 100 may be connected to the workstation 200 via the wireless network 400.

The communication unit 260 transmits a connection checking signal to each X-ray detector 100 according to a control signal of the position determining unit 252. In this case, the connection checking signal refers to a signal that requests to check whether the X-ray detector 100 is connected to the workstation, may include a packer Internet grouper (ping) signal, but the signal is not limited thereto.

The communication unit 260 transmits the connection checking signal to each X-ray detector 100 periodically, that is, at predetermined time intervals. When a response (ack) signal is received from at least one X-ray detector 100, the position determining unit 252 determines that there is the table type, stand type, or portable type X-ray detector 100 connected to the workstation 200.

In the example of FIG. 40, the communication unit 260 receives a response signal from each of the table type X-ray detector 100 and the stand type X-ray detector 100. When three X-ray detectors 100 implemented in a table type, a stand type, and a portable type are provided, the communication unit 260 receives a response signal from each of the table type X-ray detector 100, the stand type X-ray detector 100, and the portable type X-ray detector 100.

After the response signal is received, the communication unit 260 transmits an ID checking signal to each X-ray detector 100 according to a control signal of the position determining unit 252. In this case, the ID checking signal refers to a signal that requests to check whether which X-ray detector 100 is connected, that is, an inquiry of an ID.

The communication unit 260 receives ID information from the connected X-ray detector 100. At the same time, the communication unit 260 receives position information from the connected X-ray detector 100. The position determining unit 252 determines an X-ray detector 100 and a mounting position thereof based on the simultaneously received ID information and position information. In this case, the ID information includes the ID assigned to the X-ray detector 100, and the position information includes the sensor value of the detector detecting unit 140.

For detailed description thereof, the table ID set as ID1, the stand ID set as ID2, and the portable ID set as ID3 may be stored in the storage unit 270. In addition, FIG. 40 may exemplify a case in which ID2 is assigned as an ID of the table type X-ray detector and stored in the detector storage unit 170, and ID3 is assigned as an ID of the stand type X-ray detector and stored in the detector storage unit 170.

The position determining unit 252 determines that the X-ray detector 100 is mounted in the table mounting unit 310 from a sensor value output from the table type X-ray detector 100. The position determining unit 252 determines that the stand ID is assigned to the X-ray detector 100 mounted in the table mounting unit 310 from ID information received along with the sensor value, that is, ID2. That is, the position determining unit 252 may determine that the stand X-ray detector is mounted in the table mounting unit 310.

The position determining unit 252 determines that the X-ray detector 100 is mounted in the stand mounting unit 320 from a sensor value output from the stand type X-ray detector 100. The position determining unit 252 determines that the portable ID is assigned to the X-ray detector 100 mounted in the stand mounting unit 320 from ID information received along with the sensor value, that is, ID3. That is, the position determining unit 252 may determine that the portable X-ray detector is mounted in the stand mounting unit 320.

The ID setting unit 251 keeps or changes the ID of the X-ray detector 100 according to a mounting position or an implemented type based on determination of the position determining unit 252. In the above-described example, the ID setting unit 251 may change the ID of the X-ray detector mounted in the table mounting unit 310 to the table ID, that is, ID1, or change the ID of the X-ray detector mounted in the stand mounting unit 320 to the stand ID, that is, ID2. Such ID changing may be performed based on the user input through the user interface unit 210 or automatically performed according to a program stored in the storage unit 270.

Unlike the example of FIG. 40, when three X-ray detectors 100 implemented in a table type, a stand type, and a portable type are provided, a case in which ID1 is assigned as an ID of the table type X-ray detector and stored in the detector storage unit 170, ID3 is assigned as an ID of the stand type X-ray detector and stored in the detector storage unit 170, and ID2 is assigned as an ID of the portable type X-ray detector may be exemplified.

In this case, the position determining unit 252 determines that the table ID is assigned to the X-ray detector 100 mounted in the table mounting unit 310 based on the sensor value output from the table type X-ray detector 100 and ID information, that is, ID1. That is, it may be determined that the table X-ray detector is mounted in the table mounting unit 310. The position determining unit 252 determines that the portable ID is assigned to the X-ray detector 100 mounted in the stand mounting unit 320 based on the sensor value output from the stand type X-ray detector 100 and ID information, that is, ID3. That is, it may be determined that the portable X-ray detector is mounted in the stand mounting unit 320. Also, the position determining unit 252 determines that the stand ID is assigned to the X-ray detector 100 that is portably provided based on the sensor value output from the portable type X-ray detector 100 and ID information, that is, ID2. That is, it may be determined that the stand X-ray detector is portably provided.

The ID setting unit 251 may keep an ID of the X-ray detector mounted in the table mounting unit 310 as the table ID, that is, ID1, based on determination of the position determining unit 252. Also, an ID of the X-ray detector mounted in the stand mounting unit 320 may be changed to the stand ID, that is, ID2, or an ID of the X-ray detector that is portably provided may be changed to the portable ID, that is, ID3.

Figure 41:
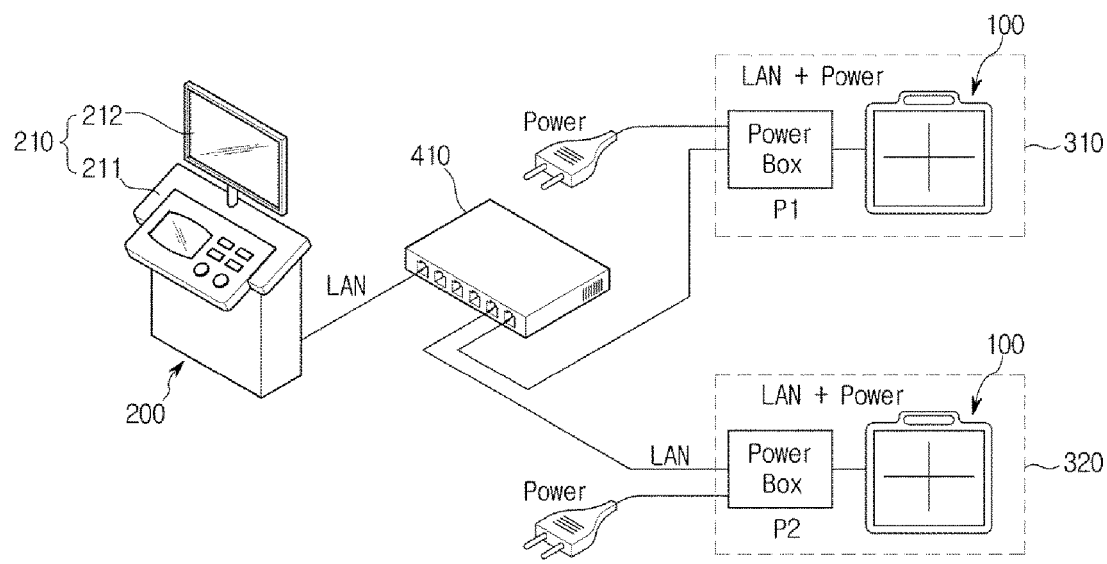
FIG. 41 is a diagram illustrating another example of the structure connecting the X-ray detector and the workstation.

FIG. 41 is a diagram illustrating another example of the structure connecting the X-ray detector and the workstation.

While a case in which the table type or stand type X-ray detector 100 is connected to the workstation 200 through the cable and the network hub 410 is exemplified in FIG. 40, a power box may be further included along a connection path as illustrated in FIG. 41. Accordingly, the power box supplies power and enables the X-ray detector 100 and the workstation 200 to share information. In this case, the power box provided in the imaging table 10 is called a first power box P1, and the power box provided in the imaging stand 20 is called a second power box P2.

Specifically, the table type X-ray detector 100 is combined with the first power box P1 or connected to the first power box P1 through the cable. The first power box P1 is connected to a power supply device and may supply power received from the power supply device to the table type X-ray detector 100. Also, the first power box P1 is connected to the workstation 200 through the cable and the network hub 410. Accordingly, the first power box P1 may output various command signals received from the workstation 200 to the table type X-ray detector 100 and output various types of data received from the table type X-ray detector 100 to the workstation 200.

The stand type X-ray detector 100 is combined with the second power box P2 or connected to the second power box P2 through the cable. The second power box P2 is connected to a power supply device and connected to the workstation 200 through the cable and the network hub 410. Accordingly, the second power box P2 may supply power received from the power supply device to the stand type X-ray detector 100. Also, the second power box P2 may output various command signals received from the workstation 200 to the stand type X-ray detector 100 and output various types of data received from the stand type X-ray detector 100 to the workstation 200.

Figure 42:
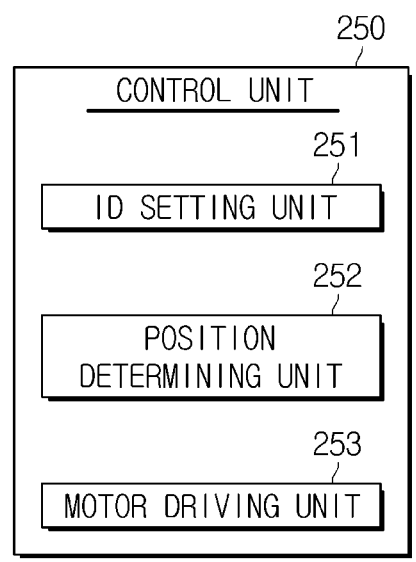
FIG. 42 is a diagram illustrating a configuration of the control unit according to another embodiment.

FIG. 42 is a diagram illustrating a configuration of the control unit according to another embodiment. As illustrated in FIG. 42, the control unit 250 may include an ID setting unit 251, a position determining unit 252, and a motor driving unit 253. Since the ID setting unit 251 and the position determining unit 252 are the same as or similar to those in FIGS. 35 to 41, descriptions thereof will not be repeated.

The motor driving unit 253 may drive the motor 90 based on a user input. In the automatic moving mode, when the user inputs a movement direction and a movement position of the X-ray source 70 through the user interface unit 210 or the manipulation unit 80, the motor driving unit 253 drives the motor and moves the X-ray source 70 according to the input movement direction and movement position.

Figure 43A:
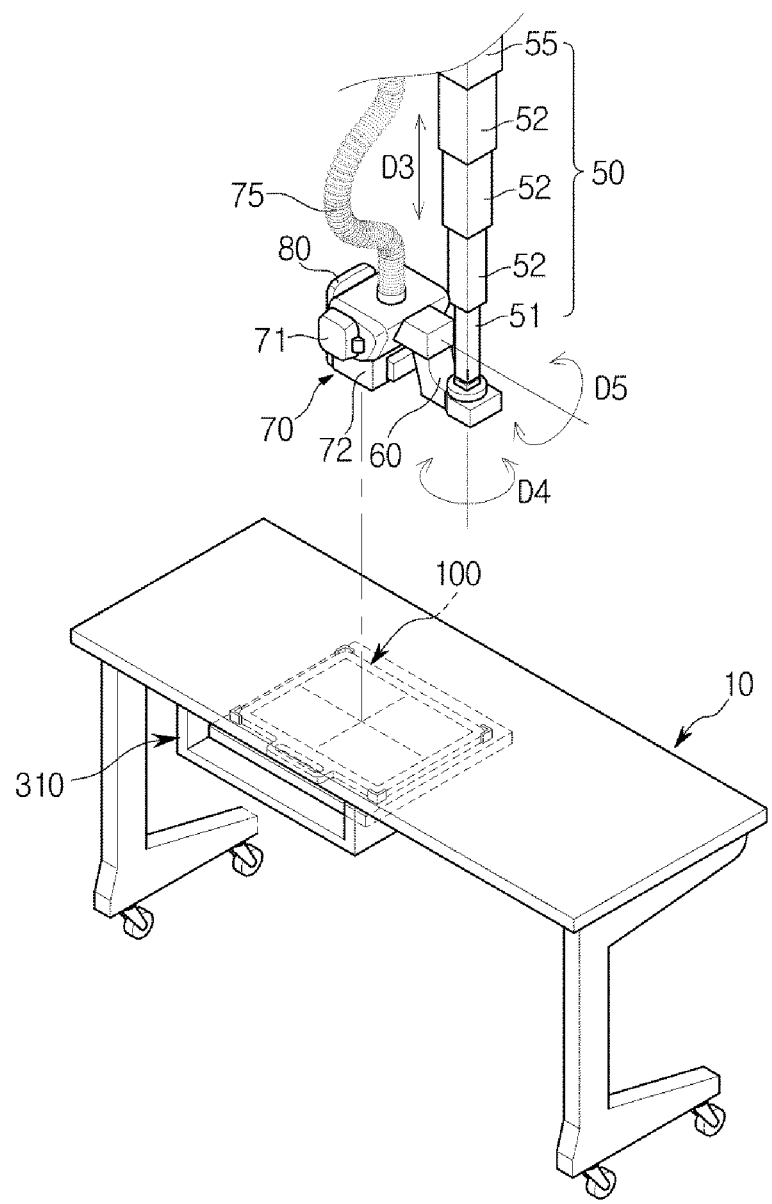
FIGS. 43A and 43B are diagrams illustrating movement of an X-ray source in an automatic moving mode.
Figure 43B:
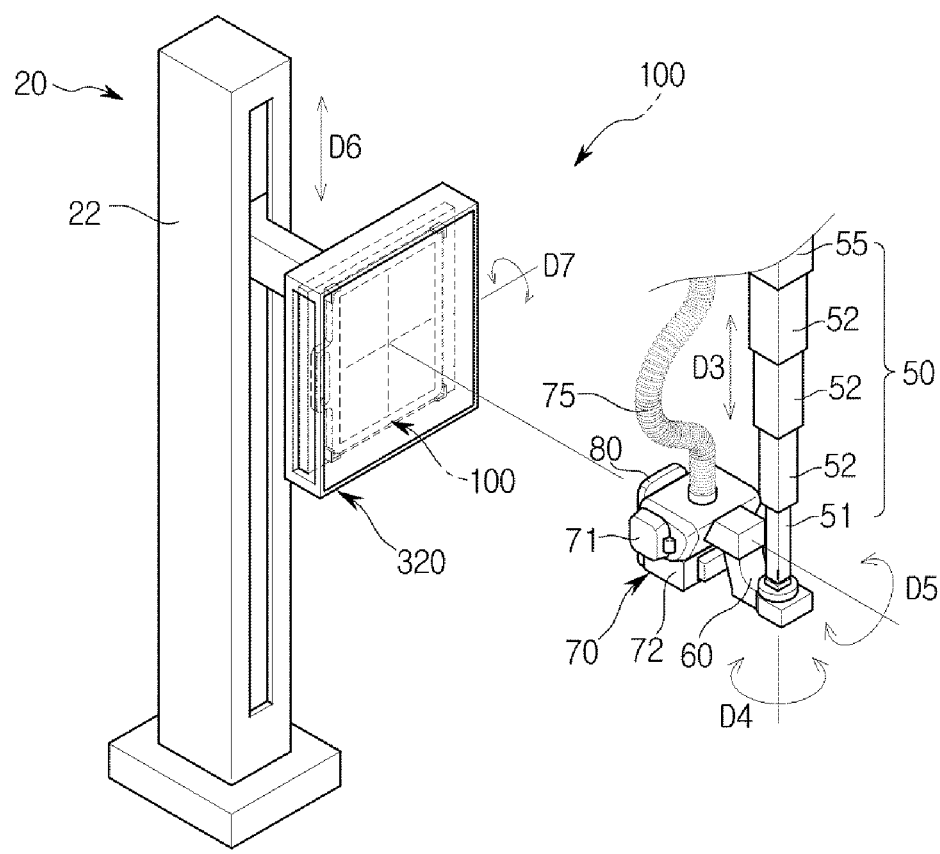

FIGS. 43A and 43B are diagrams illustrating movement of an X-ray source in an automatic moving mode.

As illustrated in FIG. 43A, when the table type X-ray detector 100 is provided, the user may select an imaging position as a "table" by pressing the button 84 or touching the display panel 81. According to the user's selection, the motor driving unit 253 calculates a current position of the X-ray source 70 and a position of the X-ray detector 100 mounted in the table mounting unit 310, and outputs a control signal to the motor 90 that needs to be driven. The X-ray source 70 moves according to driving of the motor 90. The position of the X-ray source 70 corresponds to a position of the table type X-ray detector 100.

The ID setting unit 251 may set (that is, assign or change) the table ID to the table type X-ray detector 100 before a movement command of the X-ray source 70 is input. Also, the ID setting unit 251 may set the table ID to the X-ray detector 100 while or after the X-ray source 70 moves. Therefore, X-ray imaging may be performed or an X-ray image may be obtained in the imaging table 10.

As illustrated in FIG. 43B, when the stand type X-ray detector 100 is provided, the user may select an imaging position as a "stand" by pressing the button 84 or touching the display panel 81. According to the user's selection, the motor driving unit 253 calculates a current position of the X-ray source 70 and a position of the X-ray detector 100 mounted in the stand mounting unit 320, and outputs a control signal to the motor 90 that needs to be driven. The X-ray source 70 moves according to driving of the motor 90. The position of the X-ray source 70 corresponds to a position of the stand type X-ray detector 100.

Before a movement command of the X-ray source 70 is input, the ID setting unit 251 may set the stand ID to the stand type X-ray detector 100. Also, the ID setting unit 251 may set the stand ID to the X-ray detector 100 while or after the X-ray source 70 moves. Therefore, X-ray imaging may be performed or an X-ray image may be obtained in the imaging stand 20.

Figure 44:
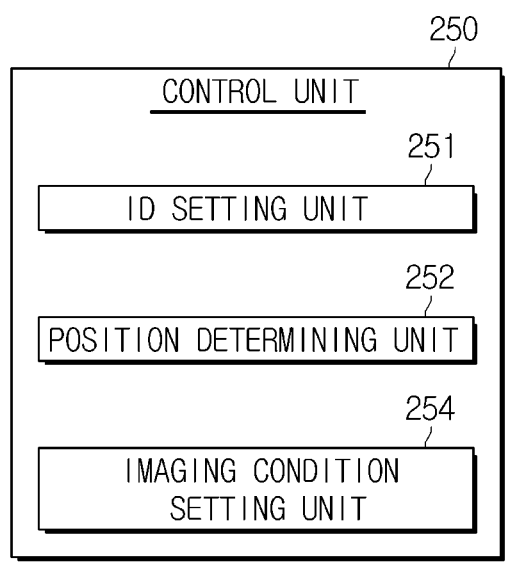
FIG. 44 is a diagram illustrating a configuration of a control unit according to another embodiment.

FIG. 44 is a diagram illustrating a configuration of a control unit according to another embodiment. As illustrated in FIG. 44, the control unit 250 may include an ID setting unit 251, a position determining unit 252, and an imaging condition setting unit 254. Since the ID setting unit 251 and the position determining unit 252 are the same as or similar to those in FIGS. 35 to 41, the imaging condition setting unit 254 will be described below.

A permeability or a degree of attenuation of X-rays differs according to a property of a material to be transmitted and a thickness of the material. In this case, a numerical expression of a degree of X-ray attenuation may be defined as an attenuation coefficient.

For example, when X-rays having the same energy are radiated, an attenuation coefficient of bone is greater than an attenuation coefficient of muscle, and an attenuation coefficient of muscle is greater than an attenuation coefficient of fat. That is, as the material becomes harder, the attenuation coefficient increases. Such an attenuation coefficient may be represented as the following [Equation 1].

$$I = I_0 \cdot e^{-\mu(E) \cdot T} \qquad \text{[Equation 1]}$$

Here, $I_0$ denotes an X-ray dose radiated to a material, I denotes an X-ray dose transmitting the material, and $\mu(E)$ denotes an attenuation coefficient of the material for X-rays having an energy E. T denotes a thickness of the material through which X-rays are transmitted.

According to [Equation 1], as the attenuation coefficient increases (that is, as the material becomes harder), and as the material becomes thicker, an X-ray dose to be transmitted becomes smaller. Accordingly, the X-ray dose should be differently radiated according to an imaging part of the object. For example, since a part lower than the chest (for example, a pelvis) is thicker than the chest and includes hard bones, a higher X-ray dose should be radiated when the part lower than the chest is imaged than when the chest is imaged.

The imaging condition setting unit 254 sets imaging conditions of the X-ray source 70, that is, an X-ray dose, according to an imaging position selected by the user or a position in which the X-ray detector 100 is mounted.

In general, imaging of the part lower than the chest is performed in the imaging table 10, and imaging of the chest is performed in the imaging stand 20. Accordingly, when the user selects the imaging table 10 as the imaging position or when the position determining unit 252 determines that there is the table type X-ray detector 100, the imaging condition setting unit 254 may set imaging conditions at an X-ray dose that is appropriate for the part lower than the chest. On the other hand, when the user selects the imaging stand 20 as the imaging position or when the position determining unit 252 determines that there is the stand type X-ray detector 100, the imaging condition setting unit 254 may set imaging conditions at an X-ray dose that is appropriate for the chest.

When the user selects portable imaging or when the position determining unit 252 determines that there is the portable type X-ray detector 100, the imaging condition setting unit 254 may set imaging conditions based on the sensor value of the detector detecting unit 140.

In the example of FIG. 33, when it is determined that X-ray detector 100 is a portable type, the position determining unit 252 may determine a desired imaging part using the tilt detected by the tilt sensor G. When the tilt sensor G detects a horizontal state (or detects about 90°), the position determining unit 252 determines that the part lower than the chest is imaged. When the tilt sensor G detects a non-horizontal state, the position determining unit 252 may determine that the chest is imaged.

Accordingly, the imaging condition setting unit 254 may set imaging conditions based on a tilt detected by the tilt sensor G or an imaging part determined by the position determining unit 252. In the above-described example, when the tilt sensor G detects a horizontal state or when the position determining unit 252 determines that the part lower than the chest is imaged, the imaging condition setting unit 254 sets imaging conditions at an X-ray dose that is appropriate for the part lower than the chest. On the other hand, when the tilt sensor G detects a non-horizontal state or when the position determining unit 252 determines that the chest is imaged, the imaging condition setting unit 254 may set imaging conditions at an X-ray dose that is appropriate for the chest.

For this purpose, the storage unit 270 may store imaging conditions, that is, the X-ray dose when the chest is imaged and the X-ray dose when the part lower than the chest is imaged.

The communication unit 260 may allow the workstation 200 to be connected to an external device via wired and/or wireless communication. The communication unit 260 may transmit and receive various types of signals and data with, for example, the X-ray source 70, the X-ray detector 100, the manipulation unit 80, a remote controller, a terminal, and the like.

The communication unit 260 may share a user command input through the user interface unit 210 with the manipulation unit 80 or may share a user command input to the manipulation unit 80 with the workstation 200.

In order to control the X-ray source 70, the communication unit 260 may transmit a user command input to the user interface unit 210 or a control signal of the control unit 250 to the X-ray source 70. For example, the communication unit 260 may transmit a movement command of the X-ray source 70 to the X-ray source 70.

The communication unit 260 may transmit and receive various types of signals and data with the X-ray detector 100. The communication unit 260 may transmit a connection checking signal to the X-ray detector 100 or receive a response signal from the X-ray detector 100. The communication unit 260 may transmit an ID checking signal to the X-ray detector 100. The communication unit 260 may transmit assigned or changed ID information to the X-ray detector 100. The communication unit 260 may receive ID information and position information of the X-ray detector 100. In this case, the ID information and the position information are simultaneously received.

The communication unit 260 may include various communication modules that can communicate with the external device, for example, various communication modules such as a wireless Internet module, a short-range communication module, a mobile communication module, and a GPS module. The wireless Internet module, the short-range communication module, and the mobile communication module are the same as those in the detector communication unit 160. The GPS module is a module configured to receive a GPS signal from GPS satellites and detect a position of the external device, for example, a current position of the X-ray source 70, and the like. However, the embodiments are not limited thereto, but the communication unit 260 may use other types of communication modules in addition to the above-described modules, as long as it can communicate with the X-ray detector 100 and the like.

The user interface unit 210 includes the input unit 211 and the display unit 212, and provides a user interface. The display unit 212 may display various pieces of information about X-ray imaging. The display unit 212 may display an X-ray detector and a mounting position thereof based on determination of the control unit 250.

Figure 45A:
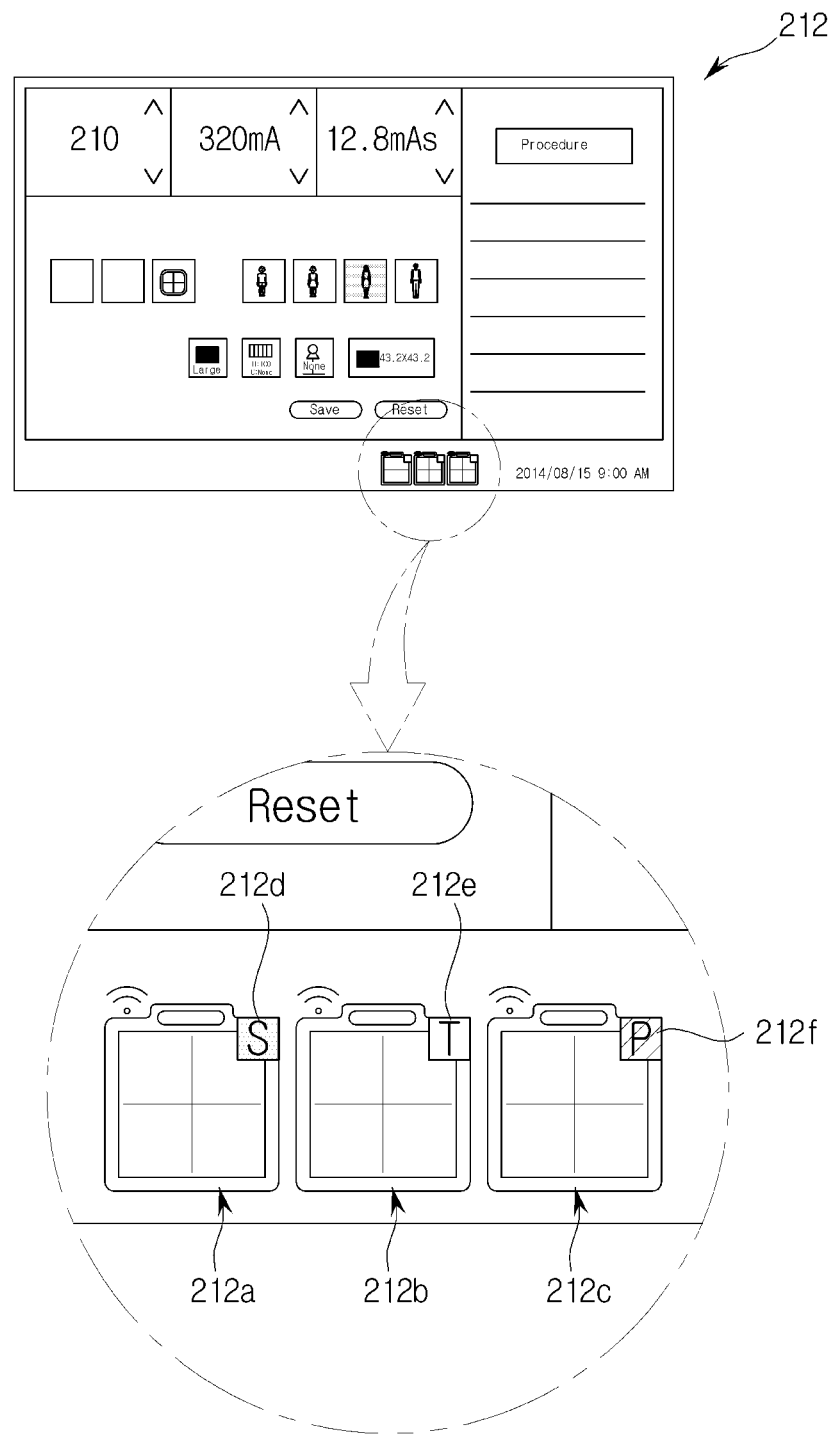
FIG. 45A is a diagram illustrating an example of a display unit screen.
Figure 45B:
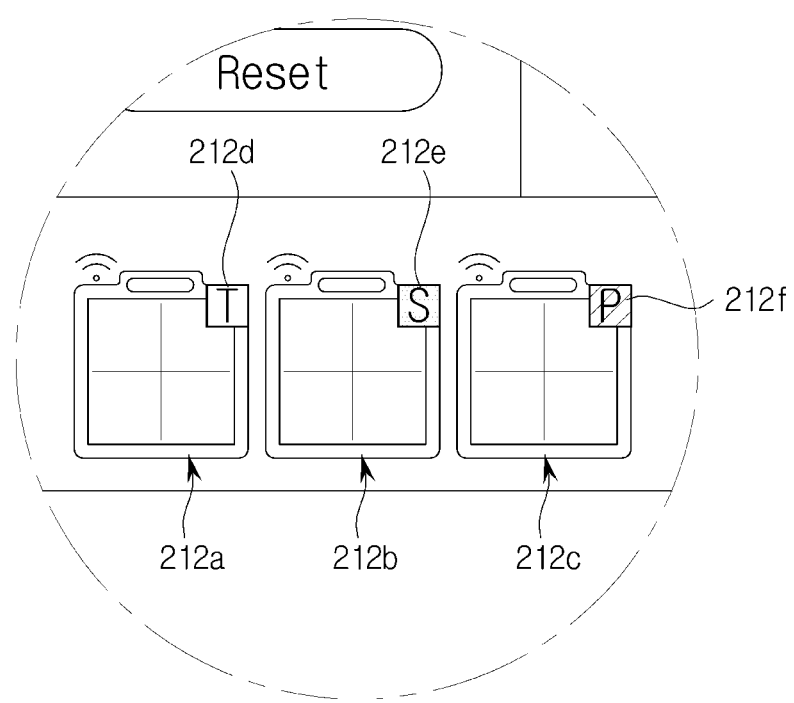
FIG. 45B is a diagram illustrating another example of the display unit screen.

FIG. 45A is a diagram illustrating an example of a display unit screen. FIG. 45B is a diagram illustrating another example of the display unit screen.

As illustrated in FIG. 45A, the display unit 212 may display current imaging conditions, imaging procedures, and the like at the top of a screen and may display an icon to set imaging conditions, an icon to save, and the like. The display unit 212 may display a mounting state and a mounting position of the X-ray detector 100, the number of mounted X-ray detectors 100, a usage of the mounted X-ray detector 100, and the like at the bottom of a screen. The display unit 212 may display an X-ray detector 100 and a mounting position thereof.

The display unit 212 may display a plurality of icons at the bottom. The display unit 212 may dispose a plurality of icons in the form of the X-ray detector 100 side by side. A first icon 212a (hereinafter referred to as a "first icon") may be set as an icon to display the stand type X-ray detector 100. A second icon 212b (hereinafter referred to as a "second icon") may be set as an icon to display the table type X-ray detector 100. A third icon 212c (hereinafter referred to as a "third icon") may be set as an icon to display the portable type X-ray detector 100.

When there is the stand type X-ray detector 100, the first icon 212a displays a mark 212d (hereinafter referred to as a "first mark") indicating a usage of the X-ray detector 100 so that presence of the stand type X-ray detector 100 may be displayed. In FIG. 45A, the user may check that the stand type X-ray detector 100 is provided and the stand ID is set to the stand type X-ray detector 100 through the first mark 212d.

When there is the table type X-ray detector 100, the second icon 212b displays a mark 212e (hereinafter referred to as a "second mark") indicating a usage of the X-ray detector 100 so that presence of the table type X-ray detector 100 may be displayed. In FIG. 45A, the user may check that the table type X-ray detector 100 is provided and the table ID is set to the table type X-ray detector 100 through the second mark 212e.

When there is the portable type X-ray detector 100, the third icon 212c displays a mark 212f (hereinafter referred to as a "third mark") indicating a usage of the X-ray detector 100 so that presence of the portable type X-ray detector 100 may be displayed. In FIG. 45A, the user may check that the portable type X-ray detector 100 is provided and the portable ID is set to the portable type X-ray detector 100 through the third mark 212f.

On the other hand, in FIG. 45B, the user may check that the stand type X-ray detector 100 is provided and the table ID is set to the stand type X-ray detector 100 through the first mark 212a. The user may check that the table type X-ray detector 100 is provided and the stand ID is set to the table type X-ray detector 100 through the second mark 212e. Similarly, the user may check that the portable type X-ray detector 100 is provided and the portable ID is set to the portable type X-ray detector 100 through the third mark 212f.

As described above, the display unit 212 may display a usage of the X-ray detector 100 and a mounting position thereof. As in FIG. 45B, when the ID of the X-ray detector 100 is not set according to a mounting position or an implemented type, the ID setting unit 251 changes the ID. Since details thereof have been described above, redundant descriptions will not be provided.

The storage unit 270 stores data and a program to manipulate the X-ray imaging apparatus 1 temporarily or non-temporarily.

The storage unit 270 may store the sensor value of the detector detecting unit 140 that is changed according to a mounting position of the X-ray detector 100 in advance. When the detector detecting unit 140 includes the linear magnetic sensor M, the storage unit 270 may store a magnetic field direction or a magnetic field strength that is changed according to a mounting position of the X-ray detector 100 in advance. When the detector detecting unit 140 includes the nonlinear magnetic sensor H, the storage unit 270 may store an output of on or off that is changed according to a mounting position of the X-ray detector 100 in advance. When the detector detecting unit 140 includes the tilt sensor G, the detector storage unit 270 may store a degree of a tilt that is changed according to a mounting position of the X-ray detector 100 in advance.

The storage unit 270 may store the threshold value that is set or adjusted to determine a position of the X-ray detector 100 in advance. The storage unit 270 may store the ID set according to the usage in advance. That is, the storage unit 270 may store the table ID, the stand ID, and the portable ID set according to the usage in advance.

The storage unit 270 may store a program to determine an X-ray detector and a mounting position thereof based on ID information and position information. The storage unit 270 may store a program to set an ID according to a usage, a program to assign an ID to the X-ray detector 100, a program to change an ID, and the like.

While embodiments of the X-ray detector, the X-ray imaging apparatus, and the method of controlling an X-ray imaging apparatus have been described above with reference to the exemplified drawings, it may be understood by those skilled in the art that the embodiments may be performed in other concrete forms without changing the technological scope and essential features. Therefore, the aforementioned embodiments should be considered as only examples in all aspects and not for purposes of limitation.

The storage unit 270 may include at least one type of a recording medium of a flash memory type, hard disk type, multimedia card micro type, and card type memory (for example, an SD or XD memory), a random access memory (RAM), a static random access memory (SRAM), a read-only memory (ROM), an electrically erasable programmable read-only memory (EEPROM), a programmable read-only memory (PROM), a magnetic memory, a magnetic disk, and an optical disk, but the embodiments are not limited thereto, and the storage unit 270 may be may be implemented as any type known in the related art. Also, the workstation 200 may operate a Web storage that performs a store function in the Internet.

Figure 46:
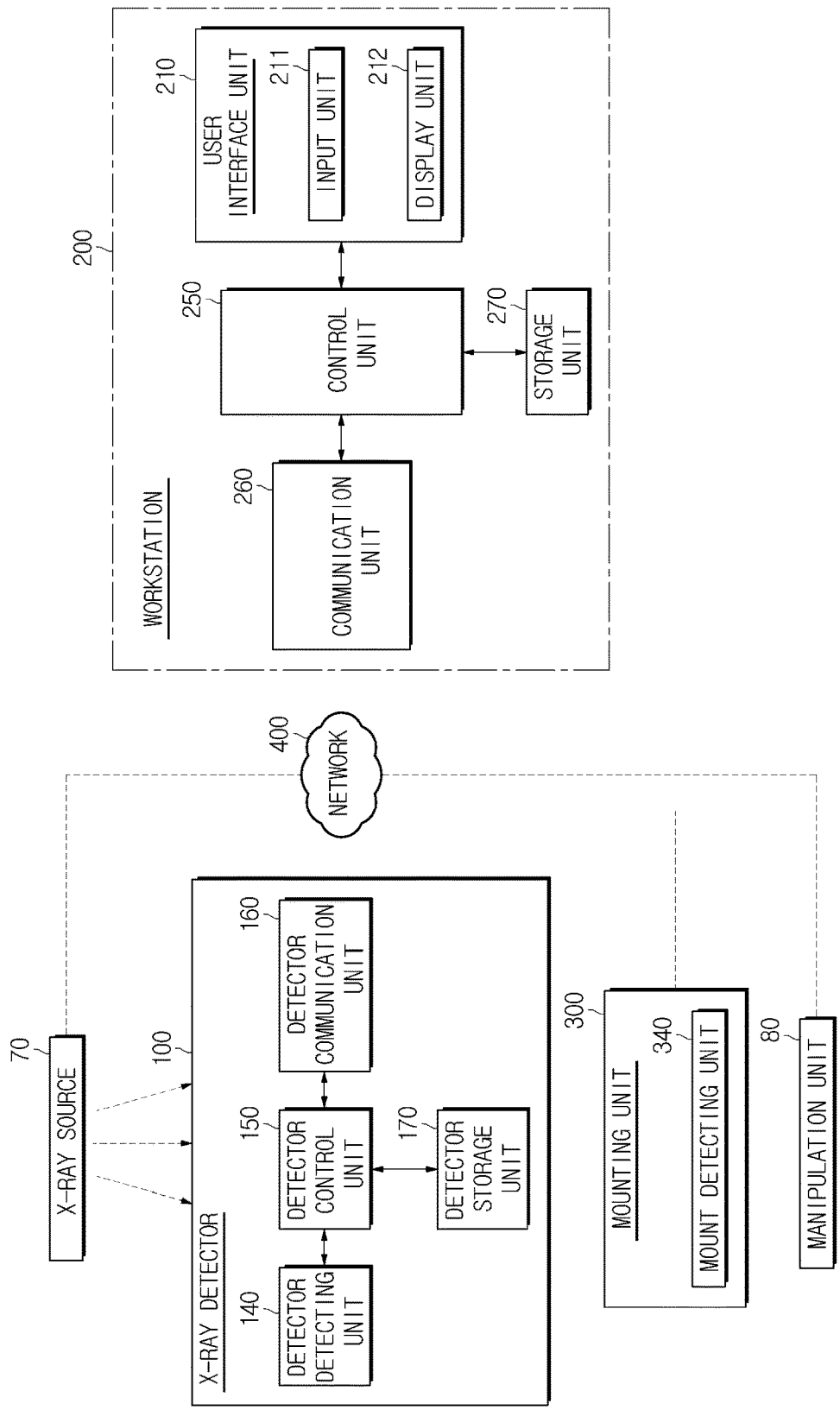
FIG. 46 is a control block diagram of an X-ray imaging apparatus according to another embodiment.

FIG. 46 is a control block diagram of an X-ray imaging apparatus according to another embodiment. When the X-ray imaging apparatus according to another embodiment is described, the same reference numerals are assigned to the same or similar configurations and functions to those of the above-described embodiment, and detailed descriptions thereof will not be repeated.

As illustrated in FIG. 46, the X-ray imaging apparatus 1 may include the workstation 200, the X-ray source 70, the X-ray detector 100, the mounting unit 300, and the manipulation unit 80. The X-ray source 70, the X-ray detector 100, the mounting unit 300, and the manipulation unit 80 may be connected to the workstation 200 via the wired and/or wireless network 400.

The X-ray source 70 generates X-rays and radiates the X-rays to the object. The X-ray detector 100 detects X-rays transmitted the object and obtains an X-ray image of an inside of the object.

The X-ray detector 100 may include the detector detecting unit 140, the detector control unit 150, the detector communication unit 160, and the detector storage unit 170.

The detector detecting unit 140 may include at least one sensor detecting a position of the X-ray detector 100.

As illustrated in FIGS. 13 to 29, the detector detecting unit 140 may include at least one linear magnetic sensor M. When the detector detecting unit 140 includes a plurality of linear magnetic sensors M, the sensors may be grouped as a plurality of sensor groups. Each sensor group may include a plurality of linear magnetic sensors M. The number of sensors to be included may be different for each sensor group. The magnet may be provided in the mounting unit 300. According to a position of the linear magnetic sensor M or the number of linear magnetic sensors M, the magnet of the table mounting unit 310, the magnet of the stand mounting unit 320, or the magnet of the portable mounting unit 330 may be provided in a region that does not correspond to each other or may also be provided in a region that corresponds to each other. According to a position of the linear magnetic sensor M or the number of linear magnetic sensors M, each of the magnet of the table mounting unit 310, the magnet of the stand mounting unit 320, and the magnet of the portable mounting unit 330 may be aligned by different polarities or may be aligned by the same polarity.

A magnetic field detected by the linear magnetic sensor M, that is, a magnetic field direction or a magnetic field strength is changed according to a mounting position of the X-ray detector 100. The control unit 250 determines a mounting position of the X-ray detector 100 using the magnetic field detected by the linear magnetic sensor M in this manner. The sensor value of the linear magnetic sensor M according to the mounting position may be stored in the storage unit 270 in advance. Also, when the X-ray detector 100 is mounted, the sensor value of the linear magnetic sensor M may be stored in the detector storage unit 170 temporarily or non-temporarily.

As illustrated in FIGS. 30 and 31, the detector detecting unit 140 may include the nonlinear magnetic sensor H. The magnet may be provided in the mounting unit 300. According to a position of the linear magnetic sensor M or the number of linear magnetic sensors M, the magnet of the table mounting unit 310, the magnet of the stand mounting unit 320, or the magnet of the portable mounting unit 330 may be provided in a region that does not correspond to each other or may also be provided in a region that corresponds to each other. Each of the magnet of the table mounting unit 310, the magnet of the stand mounting unit 320, and the magnet of the portable mounting unit 330 may be aligned by the same polarity.

According to a mounting position of the X-ray detector 100, an output of on or off of the nonlinear magnetic sensor H becomes different. The control unit 250 determines a mounting position of the X-ray detector 100 based on an output of on or off of the nonlinear magnetic sensor H in this manner. The sensor value of the nonlinear magnetic sensor H according to a mounting position may be stored in the storage unit 270 in advance. Also, when the X-ray detector 100 is mounted, the sensor value of the nonlinear magnetic sensor H may be stored in the detector storage unit 170 temporarily or non-temporarily.

As illustrated in FIG. 32, the detector detecting unit 140 may also include the tilt sensor G. A tilt detected by the tilt sensor G becomes different according to whether the X-ray detector 100 is mounted in the table mounting unit 310 or in the stand mounting unit 320. The control unit 250 determines a mounting position of the X-ray detector 100 using a tilt detected by the tilt sensor G in this manner. The sensor value of the tilt sensor G according to a mounting position may be stored in the storage unit 270 in advance. Also, when the X-ray detector 100 is mounted, the sensor value of the tilt sensor G may be stored in the detector storage unit 170 temporarily or non-temporarily.

As illustrated in FIGS. 33 and 34, the detector detecting unit 140 may include a combination of various types of sensors. For example, the detector detecting unit 140 may include a combination of the linear magnetic sensor M and the tilt sensor G, or may also include a combination of the nonlinear magnetic sensor H and the tilt sensor G.

The detector detecting unit 140 detects a tilt through the tilt sensor G and detects a magnetic field through the linear magnetic sensor M or the nonlinear magnetic sensor H. The control unit 250 determines a mounting position of the X-ray detector 100 using the sensor value of the linear magnetic sensor M or the nonlinear magnetic sensor H and the sensor value of the tilt sensor G. The control unit 250 may also determine a location of a desired imaging part using the sensor value of the tilt sensor G.

The sensor value of the linear magnetic sensor M and the sensor value of the tilt sensor G (or the sensor value of the nonlinear magnetic sensor H and the sensor value of the tilt sensor G) according to a mounting position may be stored in the storage unit 270 in advance. Also, when the X-ray detector 100 is mounted, the sensor value of the linear magnetic sensor M and the sensor value of the tilt sensor G (or the sensor value of the nonlinear magnetic sensor H and the sensor value of the tilt sensor G) may be stored in the detector storage unit 170 temporarily or non-temporarily.

When the plurality of X-ray detectors 100 are provided, the detector detecting units 140 included in the plurality of X-ray detectors 100 have the same configuration.

The mounting unit 300 includes a mount detecting unit 340 configured to detect whether the X-ray detector 100 is mounted. The table mounting unit 310 and the stand mounting unit 320 each include the mount detecting unit 340.

The mount detecting unit 340 may include at least one sensor in order to detect whether the X-ray detector 100 is mounted. The mount detecting unit 340 may include a contact sensor, a non-contact sensor, or a combination of a contact sensor and a non-contact sensor.

The contact sensor is a sensor configured to detect a mounting state of the X-ray detector 100 according to whether a collision actually occurs, and may include a limit switch, a micro switch, a touch switch, and the like.

The contact sensor may include a normally open (NO) contact sensor or a normally closed (NC) contact sensor. The NO contact sensor refers to a sensor that normally maintains an off state but outputs on when the X-ray detector 100 is mounted in the mounting unit 300 and collides with the contact sensor. The NC contact sensor refers to a sensor that normally maintains an on state but outputs off when the X-ray detector 100 is mounted in the mounting unit 300 and collides with the contact sensor.

The non-contact sensor is a sensor configured to detect whether the X-ray detector 100 is mounted regardless of collision, and may include an ultrasonic sensor, an optical sensor, an RF sensor, an image sensor, and the like.

When the mount detecting unit 340 includes the ultrasonic sensor, an ultrasound is radiated to an inside of the mounting unit 300. Based on a reception intensity or a reception time of a reflective ultrasound, a mounting state of the X-ray detector is detected. When the mount detecting unit 340 includes the optical sensor, lights having a range of infrared light or visible light are emitted to an inside of the mounting unit 300. Based on a reception intensity or a reception time of reflective light, a mounting state of the X-ray detector is detected. When the mount detecting unit 340 includes the RF sensor, a wave of a specific frequency, for example, a microwave, is transmitted using the Doppler effect. A mounting state of the X-ray detector is detected by detecting a change in a frequency of a reflective wave.

However, the embodiments are not limited to the above detection methods. A kind or a form of a sensor included in the mount detecting unit 340 is not limited, as long as a mounting state of the X-ray detector 100 can be detected.

Referring again to FIG. 46, the workstation 200 may include the user interface unit 210, the communication unit 260, the control unit 250, and the storage unit 270.

The control unit 250 may assign or change the ID of the X-ray detector 100. The control unit 250 may receive the sensor value of the mount detecting unit 340 and may determine a mounting state or a mounting position of the X-ray detector based on the received sensor value. The control unit 250 may receive ID information and position information of the X-ray detector 100 from the X-ray detector 100 and may determine an X-ray detector 100 and a mounting position thereof based on the ID information and position information. In this case, the ID information includes the ID assigned to the X-ray detector 100, and the position information includes the sensor value of the detector detecting unit 140.

Figure 47:
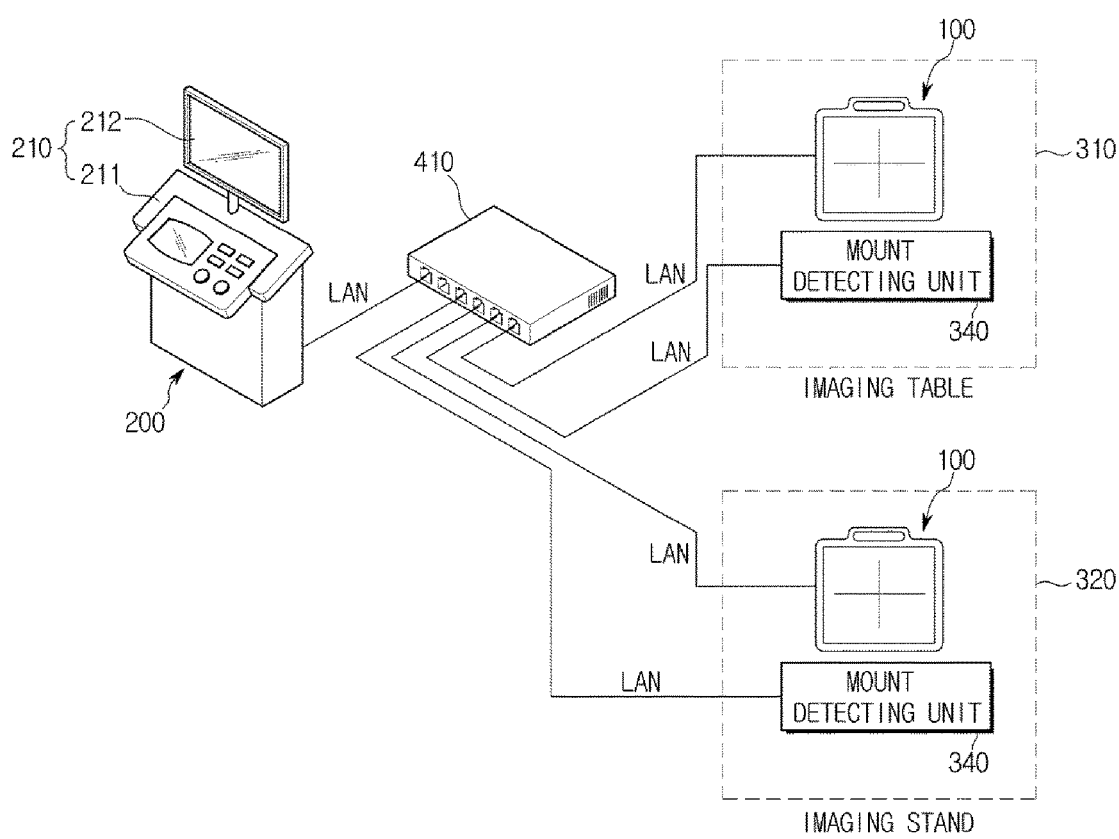
FIG. 47 is a diagram illustrating an example of a structure connecting the X-ray detector and a mount detecting unit.

FIG. 47 is a diagram illustrating an example of a structure connecting the X-ray detector and a mount detecting unit.

As exemplified in FIG. 47, two X-ray detectors 100 are provided. One of the two X-ray detectors 100 may be mounted in the table mounting unit 310 and implemented in a table type. The other detector may be mounted in the stand mounting unit 320 and implemented in a stand type. Also, unlike the example of FIG. 40, three X-ray detectors 100 may be provided. One of the three X-ray detectors 100 may be implemented in a table type, another detector may be implemented in a stand type, and the other detector may be implemented in a portable type. In this case, the portable type X-ray detector 100 may be mounted in the portable mounting unit 330 and may also be provided without being mounted in the mounting unit 300.

Each of the plurality of X-ray detectors 100 implemented in different types is connected to the workstation 200 via the wired network or wireless network 400. As illustrated in FIG. 47, each of the table type X-ray detector 100 and the stand type X-ray detector 100 may be connected to the workstation 200 via the wired network 400 including the cable and the network hub 410. The portable type X-ray detector 100 may be connected to the workstation 200 via the wireless network 400.

Also, the mount detecting unit 340 provided in a different mounting unit 300 may be connected to the workstation 200 via the wired network 400 including the cable and the network hub 410. Each of the mount detecting unit 340 provided in the table mounting unit 310 and the mount detecting unit 340 provided in the stand mounting unit 320 is connected to the workstation 200. In this case, the mount detecting unit 340 provided in the table mounting unit 310 is called a first detecting unit, and the mount detecting unit 340 provided in the stand mounting unit 320 is called a second detecting unit.

The mount detecting unit 340 detects a mounting state of the X-ray detector 100 and transmits the sensor value to the workstation 200. In the example of FIG. 47, the first detecting unit detects the X-ray detector 100 mounted in the table mounting unit 310 and transmits the sensor value. Similarly, the second detecting unit detects the X-ray detector 100 mounted in the stand mounting unit 320 and transmits the sensor value.

The control unit 250 determines that there is the table type or stand type X-ray detector 100 connected to the workstation 200 based on the sensor value of the mount detecting unit 340. The control unit 250 determines that there is the table type X-ray detector 100 from a sensor value of the first detecting unit or a change in the sensor value. The control unit 250 determines that there is the stand type X-ray detector 100 from a sensor value of the second detecting unit or a change in the sensor value. Regardless of the sensor value of the mount detecting unit 340, the control unit 250 may check whether there is the portable type X-ray detector 100 via wireless communication.

The communication unit 260 transmits an ID checking signal to each X-ray detector 100 according to a control signal of the control unit 250. The communication unit 260 receives ID information from the connected X-ray detector 100. At the same time, the communication unit 260 receives position information from the connected X-ray detector 100. The control unit 250 determines an X-ray detector 100 and a mounting position thereof based on the simultaneously received ID information and position information. In this case, ID information includes the ID assigned to the X-ray detector 100, and the position information includes the sensor value of the detector detecting unit 140.

For detailed description thereof, the table ID set as ID1, the stand ID set as ID2, and the portable ID set as ID3 may be stored in the storage unit 270. In addition, in FIG. 47, a case in which ID2 is assigned as an ID of the table type X-ray detector and stored in the detector storage unit 170, and ID3 is assigned as an ID of the stand type X-ray detector and stored in the detector storage unit 170 may be exemplified.

The control unit 250 determines that the X-ray detector 100 is mounted in the table mounting unit 310 from a sensor value output from the table type X-ray detector 100. The control unit 250 determines that the stand ID is assigned to the X-ray detector 100 mounted in the table mounting unit 310 from ID information received along with the sensor value, that is, ID2. That is, the control unit 250 may determine that the stand X-ray detector is mounted in the table mounting unit 310.

The control unit 250 determines that the X-ray detector 100 is mounted in the stand mounting unit 320 from a sensor value output from the stand type X-ray detector 100. The control unit 250 determines that the portable ID is assigned to the X-ray detector 100 mounted in the stand mounting unit 320 from ID information received along with the sensor value, that is, ID3. That is, the control unit 250 may determine that the portable X-ray detector is mounted in the stand mounting unit 320.

The control unit 250 keeps or changes the ID of the X-ray detector 100 according to a mounting position or an implemented type. In the above-described example, the control unit 250 may change the ID of the X-ray detector mounted in the table mounting unit 310 to the table ID, that is, ID1, or change the ID of the X-ray detector mounted in the stand mounting unit 320 to the stand ID, that is, ID2. Such ID changing may be performed based on the user input through the user interface unit 210 or automatically performed according to a program stored in the storage unit 270.

Unlike the example of FIG. 47, when three X-ray detectors 100 implemented in a table type, a stand type, and a portable type are provided, a case in which ID1 is assigned as an ID of the table type X-ray detector and stored in the detector storage unit 170, ID3 is assigned as an ID of the stand type X-ray detector and stored in the detector storage unit 170, and ID2 is assigned as an ID of the portable type X-ray detector may be exemplified.

In this case, the control unit 250 determines that the table ID is assigned to the X-ray detector 100 mounted in the table mounting unit 310 based on the sensor value output from the table type X-ray detector 100 and ID information, that is, ID1. That is, it may be determined that the table X-ray detector is mounted in the table mounting unit 310. The control unit 250 determines that the portable ID is assigned to the X-ray detector 100 mounted in the stand mounting unit 320 based on the sensor value output from the stand type X-ray detector 100 and ID information, that is, ID3. That is, it may be determined that the portable X-ray detector is mounted in the stand mounting unit 320. Also, the control unit 250 determines that the stand ID is assigned to the X-ray detector 100 that is portably provided based on the sensor value output from the portable type X-ray detector 100 and ID information, that is, ID2. That is, it may be determined that the stand X-ray detector is portably provided.

Also, the control unit 250 may keep an ID of the X-ray detector mounted in the table mounting unit 310 as the table ID, that is, ID1, based on the above determination. Also, an ID of the X-ray detector mounted in the stand mounting unit 320 may be changed to the stand ID, that is, ID2, or an ID of the X-ray detector that is portably provided may be changed to the portable ID, that is, ID3.

In FIG. 47, a structure in which the X-ray detector 100 and the workstation 200 are directly connected was exemplified. However, the power box may be further included along a path connecting the X-ray detector 100 and the workstation 200. Also, the power box may be further included along a path connecting the mount detecting unit 340 and the workstation 200. Also, a connecting medium other than the power box may be included.

Figure 48:
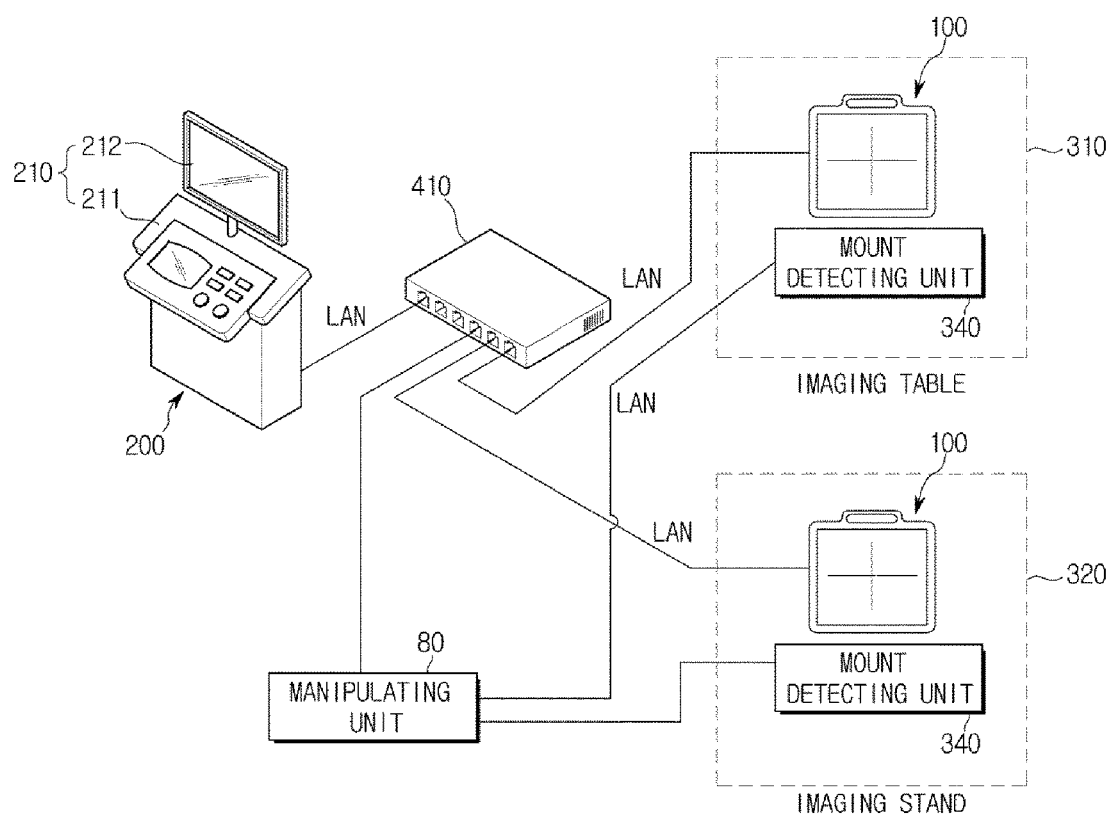
FIG. 48 is a diagram illustrating another example of the structure connecting the X-ray detector and the mount detecting unit.

FIG. 48 is a diagram illustrating another example of the structure connecting the X-ray detector and the mount detecting unit.

In FIG. 47, a case in which the mount detecting unit 340 is connected to the workstation 200 through the cable and the network hub 410 was exemplified. However, as illustrated in FIG. 48, the manipulation unit 80 may be further included along a connection path. Accordingly, the manipulation unit 80 may receive a user command and enables the mount detecting unit 340 and the workstation 200 to share information.

Specifically, the first detecting unit provided in the table mounting unit 310 is connected to the manipulation unit 80 through the cable, and the manipulation unit 80 is connected to the workstation 200 through the cable and the network hub 410. Accordingly, the manipulation unit 80 may display the sensor value of the first detecting unit or a mounting state of the X-ray detector 100 detected by the first detecting unit through the display panel 81, or may deliver the value or the mounting state to the workstation 200.

The second detecting unit provided in the stand mounting unit 320 is connected to the manipulation unit 80 through the cable. The manipulation unit 80 is connected to the workstation 200 through the cable and the network hub 410. Accordingly, the manipulation unit 80 may display the sensor value of the second detecting unit or a mounting state of the X-ray detector 100 detected by the second detecting unit through the display panel 81, or may deliver the value and the mounting state to the workstation 200.

Accordingly, the user may check a mounting position of the X-ray detector 100 through the manipulation unit 80 or the workstation 200.

Figure 49:
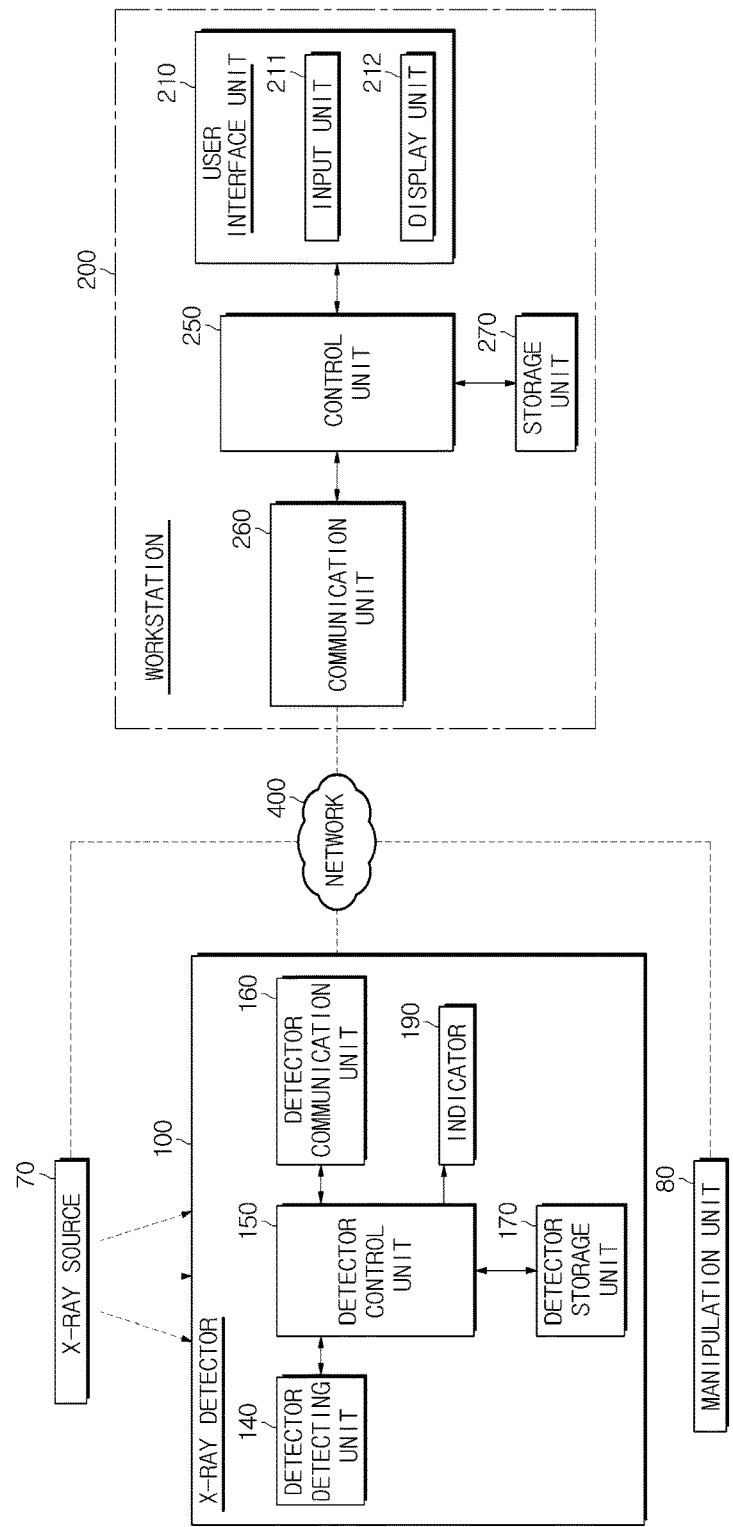
FIG. 49 is a control block diagram of an X-ray imaging apparatus according to still another embodiment.

FIG. 49 is a control block diagram of an X-ray imaging apparatus according to still another embodiment. When the X-ray imaging apparatus according to FIG. 49 is described, the same reference numerals are assigned to the same or similar configurations and functions to those of the above-described embodiment, and detailed descriptions thereof will not be repeated.

As illustrated in FIG. 49, the X-ray imaging apparatus 1 may include the workstation 200, the X-ray source 70, the X-ray detector 100, and the manipulation unit 80. The X-ray source 70, the X-ray detector 100 and the manipulation unit 80 may be connected to the workstation 200 via the wired and/or wireless network 400. The workstation 200 includes the user interface unit 210, the communication unit 260, the control unit 250, and the storage unit 270. The X-ray detector 100 may include the detector detecting unit 140, the detector control unit 150, the detector communication unit 160, the detector storage unit 170, and an indicator 190.

As described in FIG. 40, at least one X-ray detector 100 may be connected to the workstation 200 via the wired network or wireless network 400. In FIG. 40, a case in which the table type X-ray detector 100 and the stand type X-ray detector 100 are connected to the workstation 200 via the wired network 400 was exemplified. When the wired network 400 is used in this manner, even if the plurality of X-ray detectors 100 are provided, the X-ray detector 100 connected to the workstation 200 may be visually easily checked.

On the other hand, when the wireless network 400 is used, it is difficult to visually check which X-ray detector 100 is connected to the workstation 200 in some cases. For example, when the plurality of portable type X-ray detectors 100 are provided, it is difficult to check which X-ray detector 100 is connected to the workstation 200. Accordingly, the X-ray detector 100 may further include the indicator 190. It is possible to visually check the X-ray detector 100 that is connected to the workstation 200 through a display of the indicator 190.

The indicator 190 displays a connection state of the workstation 200. When the X-ray detector 100 is connected to the workstation 200 via the wired network or wireless network, the indicator 190 displays a connection state using a method of light-emitting and the like under control of the detector control unit 150. The indicator 190 may be implemented as an incandescent light emitting device such as an incandescent lamp and a halogen lamp, a discharge light emitting device such as a fluorescent lamp, or an electroluminescent device such as a lighting emitting diode (LED). However, a form of the indicator 190 or an implementation method thereof is not limited, as long as the user can recognize a connection state.

Figure 50:
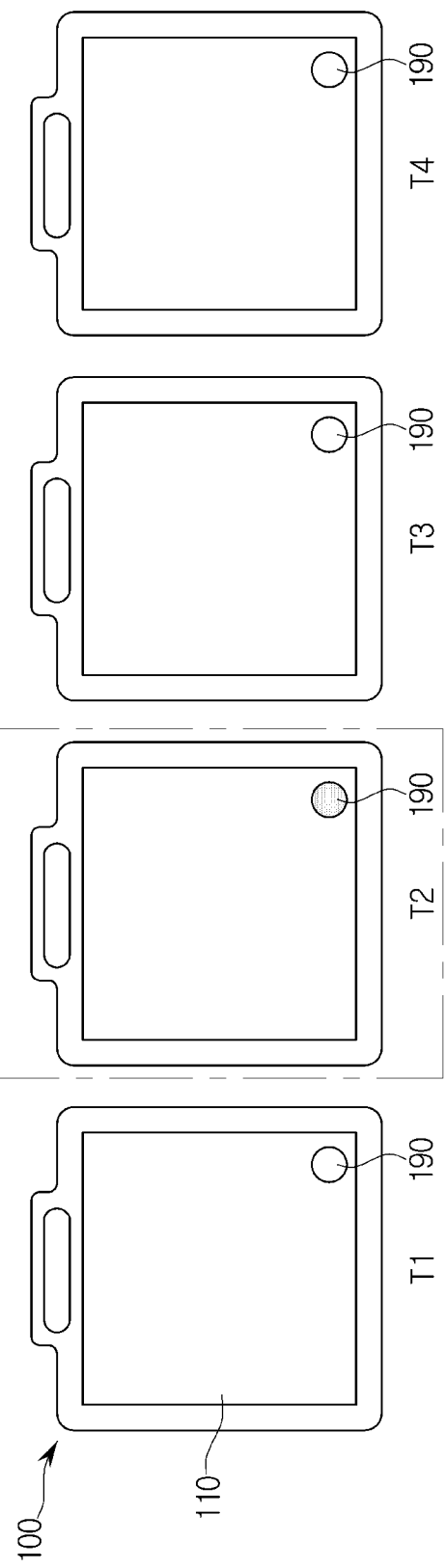
FIG. 50 is a front view of an exemplary X-ray detector including an indicator.

FIG. 50 is a front view of an exemplary X-ray detector including an indicator.

As illustrated in FIG. 50, a plurality of X-ray detectors 100 T1, T2, T3, and T4 may be provided. Each of the plurality of X-ray detectors T1, T2, T3, and T4 may include the indicator 190. When the X-ray detector T2 among the plurality of X-ray detectors T1, T2, T3, and T4 is connected to the workstation 200, the indicator 190 of the X-ray detector T2 is switched to an on state or maintains an on state. On the other hand, the indicators 190 of the remaining X-ray detectors T1, T3, and T4 are switched to an off state or maintain an off state. According to an on or off display of the indicator 190, the user may recognize that the X-ray detector T2 is connected to the workstation 200.

As illustrated in FIG. 50, the indicator 190 may be provided in a lower part of the incident surface 110. However, a position of the indicator is not limited to the position in FIG. 50, as long as the user can recognize a connection state.

Although the above embodiment has been illustrated in that the ID setting unit 251 may set, assign or change ID information of the X-ray detector 100, the present disclosure is not limited thereto. For example, according to anther embodiment, ID information of the X-ray detector 100 may be used as unique information of each X-ray detector 100, which will be described with reference to FIGS. 51 and 52.

Figure 51:
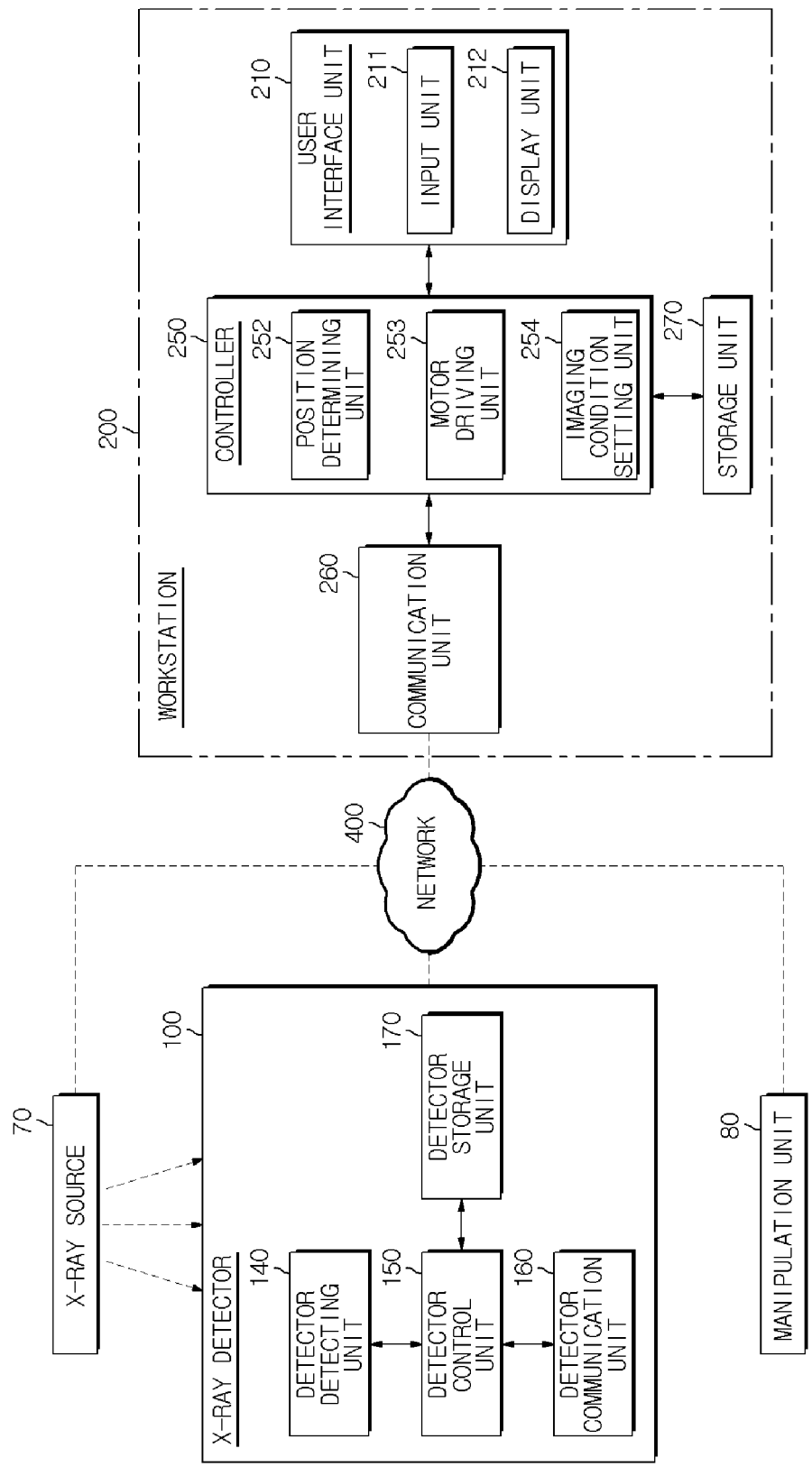
FIGS. 51 and 52 are views illustrating an embodiment in which ID information of the X-ray detector is used as unique information of each X-ray detector.
Figure 52:
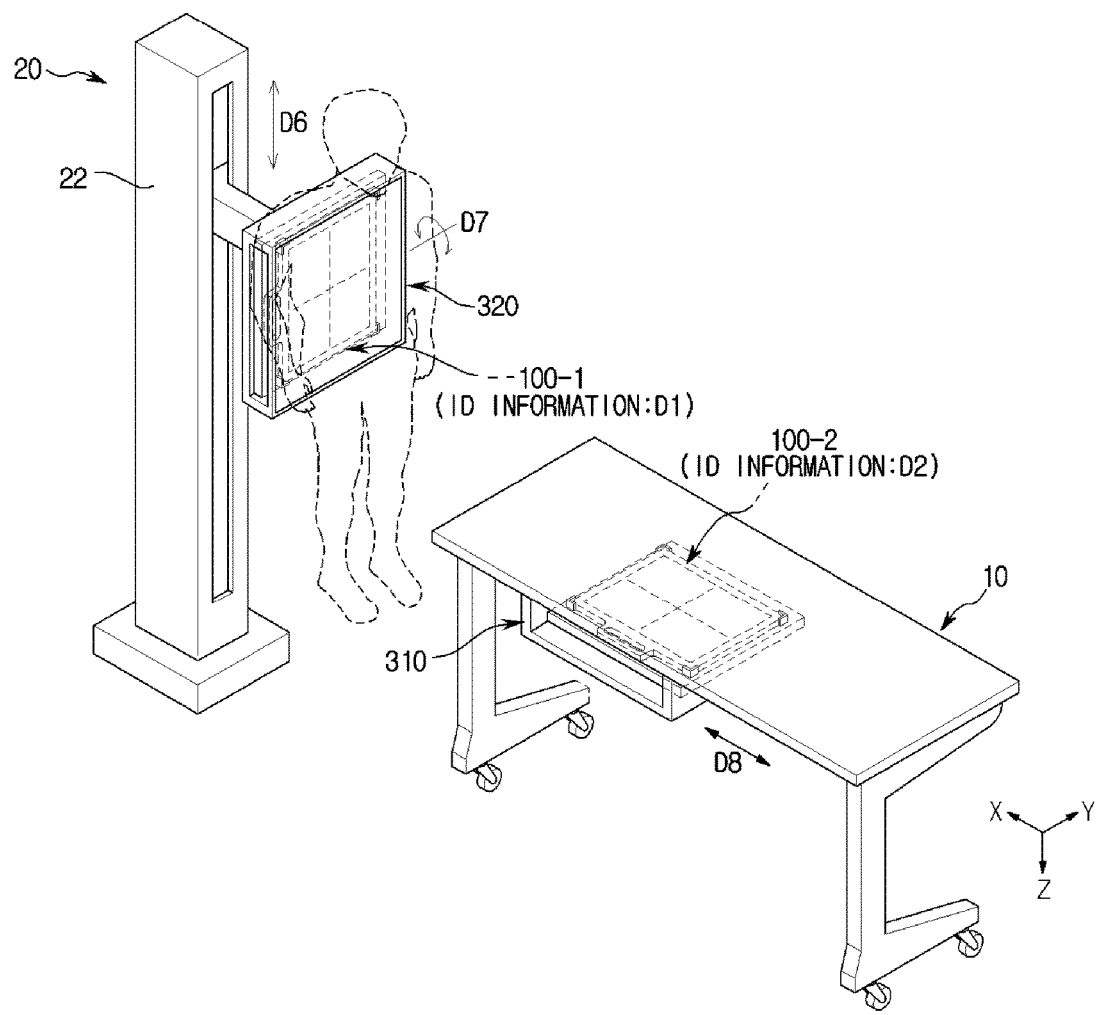

FIGS. 51 and 52 are views illustrating an embodiment in which ID information of the X-ray detector is used as unique information of each X-ray detector.

Referring to FIG. 51, the control unit 250 of the X-ray imaging apparatus 1 according to the present embodiment may include the position determining unit 252 to determine a position of the X-ray detector 100, the motor driving unit 253 to drive a motor and the imaging condition setting unit 254 to set imaging conditions, but does not include the ID setting unit 251 used in the above described embodiment. In this case, the X-ray detector 100 may be assigned unique ID information, in which the unique ID information is not set or assigned by the X-ray imaging apparatus 1 but assigned to be different between the respective X-ray detectors 100 when the X-ray detector 100 is manufactured.

The configuration or operation of the X-ray imaging apparatus 1 shown in FIG. 51 is identical to those described in the above embodiment except that ID of the X-ray detector 100 is already assigned and fixed as a unique value rather than it may be set assigned and changed by the X-ray imaging apparatus 1, and detailed description thereof will be omitted.

As described above, the position determining unit 252 may determine a mounting position of the X-ray detector 100, based on at least one of a magnetic field strength and a magnetic field direction detected by a linear magnetic sensor M or ON/OFF output of a nonlinear magnetic sensor H, and may identify the mounted X-ray detector 100 based on unique ID information.

It may be assumed that the X-ray imaging is performed using a stand type, that is, the X-ray imaging is performed while a patient stands up. Referring to FIG. 52, the position determining unit 252 determines that an X-ray detector 100-1 having ID information of D1 is mounted on the stand mounting unit 320, and an X-ray detector 100-2 having ID information of D2 is mounted on the table mounting unit 310. In this case, an X-ray detector used for X-ray imaging is the X-ray detector 100-1 mounted on the stand mounting unit 320, so the workstation 200 may receive X-ray image data from the X-ray detector 100-1 having ID information of D1. That is, the X-ray detector 100-1 mounted on the stand mounting unit 320 may be used for the X-ray imaging. In this manner, an X-ray image and relevant data thereof may be received from the X-ray detector 100 that has been actually used for the X-ray imaging without an additional input or manipulation of a user, and thus the workload of the user is reduced and repeated X-ray imaging is prevented.

Meanwhile, an X-ray detector may be designated to be exclusive for a respective mounting unit in advance. For example, the X-ray detector 100-1 having ID information of D1 may be provided for a table-use, the X-ray detector 100-2 having ID information of D2 may be provided for a stand-use, and the X-ray detector 100-3 having ID information of D3 may be provided for a portable-use. Although the uses of the respective X-ray detectors 100-1, 100-2 and 100-3 may be set in advance for convenience of user, the uses may be changed. Accordingly, when image photographing needs to be performed in a state in which a patient stands up as shown in FIG. 52, and the X-ray detector 100-1 having ID information of D1 is mounted on the stand mounting unit 320, the workstation 200 may receive an X-ray image or relevant data thereof from the X-ray detector 100-1 mounted on the current stand mounting unit 310 rather than from the X-ray detector 100-2 that has been set for a stand-purpose. In this case, the respective X-ray detectors may have the previously-set uses thereof changed according to the current mounting states thereof. Alternatively, the previously-set uses may be maintained.

Components and functions of each component of the X-ray detector and the X-ray imaging apparatus have been described above based on the embodiments. Hereinafter, a method of controlling an X-ray imaging apparatus will be described with reference to given flowcharts.

Figure 53:
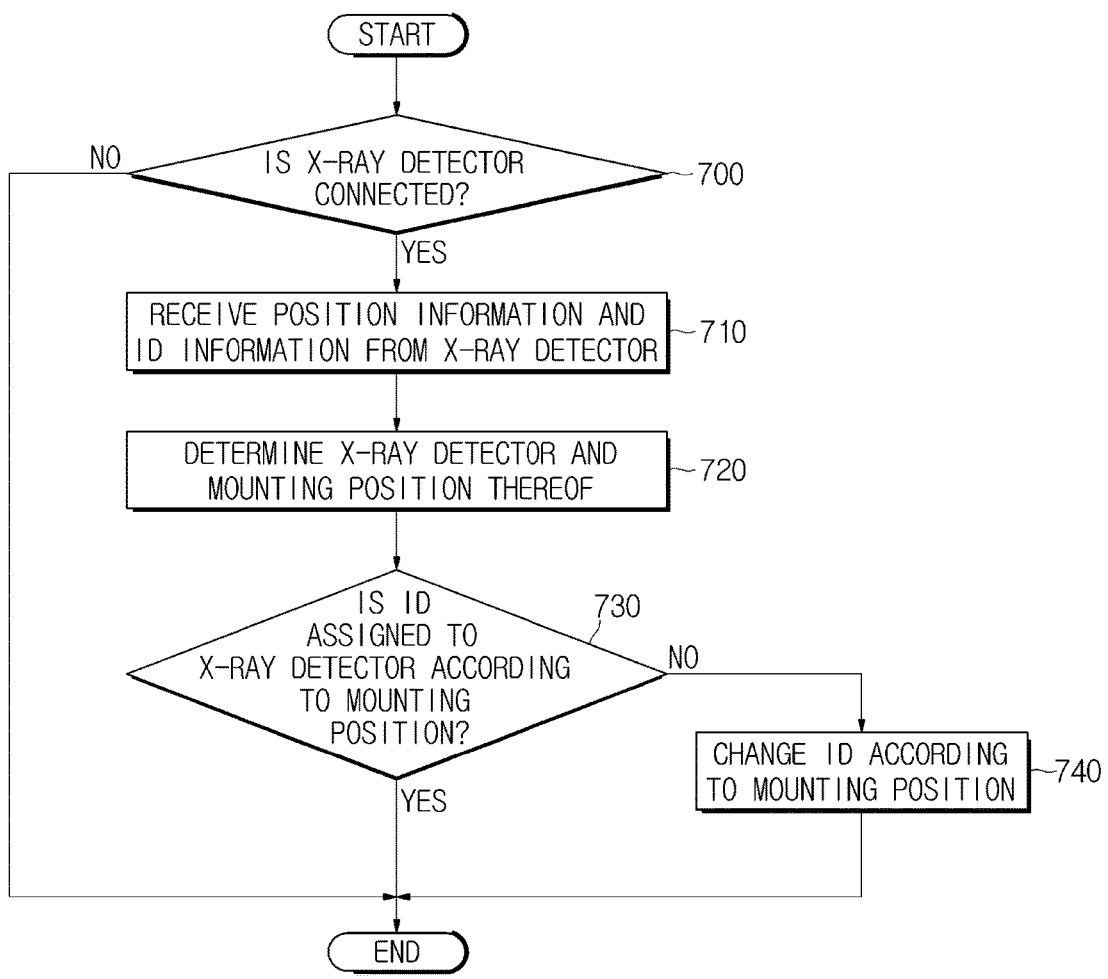
FIG. 53 is a flowchart illustrating a method of controlling an X-ray imaging apparatus according to an embodiment.

FIG. 53 is a flowchart illustrating a method of controlling an X-ray imaging apparatus according to an embodiment.

As illustrated in FIG. 53, first, a connection state of the X-ray detector 100 is determined (700).

The control unit 250 transmits a connection checking signal to the X-ray detector 100 and receives a response signal in response thereto so that a connection state of the X-ray detector 100 may be checked. In this case, the connection checking signal refers to a signal that request to check whether the X-ray detector 100 is connected to the workstation, and may include a packer Internet grouper (ping) signal.

Specifically, the control unit 250 transmits the connection checking signal to each X-ray detector 100 periodically, that is, at predetermined time intervals. When a response (ack) signal is received from at least one X-ray detector 100, the control unit determines that there is the table type, stand type, or portable type X-ray detector 100.

The control unit 250 may check a connection state of the X-ray detector 100 based on the sensor value of the mount detecting unit 340. The mount detecting unit 340 may include a contact sensor or a non-contact sensor, may be provided in each of the table mounting unit 310 and the stand mounting unit 320, and may detect a connection state of the X-ray detector 100. In this case, the mount detecting unit 340 provided in the table mounting unit 310 is called a first detecting unit, and the mount detecting unit 340 provided in the stand mounting unit 320 is called a second detecting unit.

The control unit 250 may determine whether there is the table type X-ray detector 100 from a sensor value of the first detecting unit or a change in the sensor value. The control unit 250 may determine whether there is the stand type X-ray detector 100 from a sensor value of the second detecting unit or a change in the sensor value. Regardless of the sensor value of the mount detecting unit 340, the control unit 250 may check whether there is the portable type X-ray detector 100 via wireless communication.

When there is no connected X-ray detector 100, the process immediately ends.

When there is the connected X-ray detector 100, the control unit 250 simultaneously receives position information and ID information from each X-ray detector 100 (710). In this case, the position information includes the sensor value of the detector detecting unit 140, and the ID information includes the ID assigned to the X-ray detector 100.

The control unit 250 determines an X-ray detector and a mounting position thereof based on the received position information and ID information (720).

The control unit 250 may determine a mounting position of the X-ray detector 100 based on position information.

When the detector detecting unit 140 includes the linear magnetic sensor M, the control unit 250 may determine a mounting position using a magnetic field direction or a magnetic field strength detected by the linear magnetic sensor M.

When the detector detecting unit 140 includes the nonlinear magnetic sensor H, the control unit 250 may determine a mounting position based on an output of on or off of the nonlinear magnetic sensor H.

When the detector detecting unit 140 includes the tilt sensor G, the control unit 250 may determine a mounting position using a tilt detected by the tilt sensor G. However, when the tilt sensor G detects a horizontal state, the control unit 250 may determine a mounting position according to user input information.

When the detector detecting unit 140 includes a combination of the linear magnetic sensor M and the tilt sensor G or a combination of the nonlinear magnetic sensor H and the tilt sensor G, the control unit 250 may determine a mounting position using a magnetic field detected by the linear magnetic sensor M or the nonlinear magnetic sensor H or a tilt detected by the tilt sensor G. The control unit 250 may determine a location of a desired imaging part using the sensor value of the tilt sensor G.

The control unit 250 may determine an X-ray detector 100 and a mounting position thereof using position information of the X-ray detector 100 and ID information of the X-ray detector 100.

For detailed description thereof, the table ID set as ID1, the stand ID set as ID2, and the portable ID set as ID3 may be stored in the storage unit 270. Also, a case in which three X-ray detectors 100 implemented in a table type, a stand type, and a portable type are provided, ID1 is assigned as an ID of the table type X-ray detector and stored in the detector storage unit 170, ID3 is assigned as an ID of the stand type X-ray detector and stored in the detector storage unit 170, and ID2 is assigned as an ID of the portable type X-ray detector may be exemplified.

The control unit 250 determines that the table ID is assigned to the X-ray detector 100 mounted in the table mounting unit 310 based on the sensor value output from the table type X-ray detector 100 and ID information, that is, ID1. That is, it may be determined that the table X-ray detector is mounted in the table mounting unit 310. The control unit 250 determines that the portable ID is assigned to the X-ray detector 100 mounted in the stand mounting unit 320 based on the sensor value output from the stand type X-ray detector 100 and ID information, that is, ID3. That is, it may be determined that the portable X-ray detector is mounted in the stand mounting unit 320. Also, the control unit 250 determines that the stand ID is assigned to the X-ray detector 100 that is portably provided based on the sensor value output from the portable type X-ray detector 100 and ID information, that is, ID2. That is, it may be determined that the stand X-ray detector is portably provided.

The control unit 250 determines whether an ID is assigned to the X-ray detector 100 according to a mounting position (730). When the ID is assigned according to the mounting position, the process immediately ends. When the ID is not assigned according to the mounting position, the control unit 250 changes the ID according to the mounting position (740).

In the above example, the control unit 250 changes an ID of the X-ray detector mounted in the stand mounting unit 320 to the stand ID, that is, ID2 such that the object may be imaged in the imaging stand 20. Also, an ID of the X-ray detector that is portably provided is changed to the portable ID, that is, ID3 such that the object may be imaged in various positions, directions, or angles.

Figure 54:
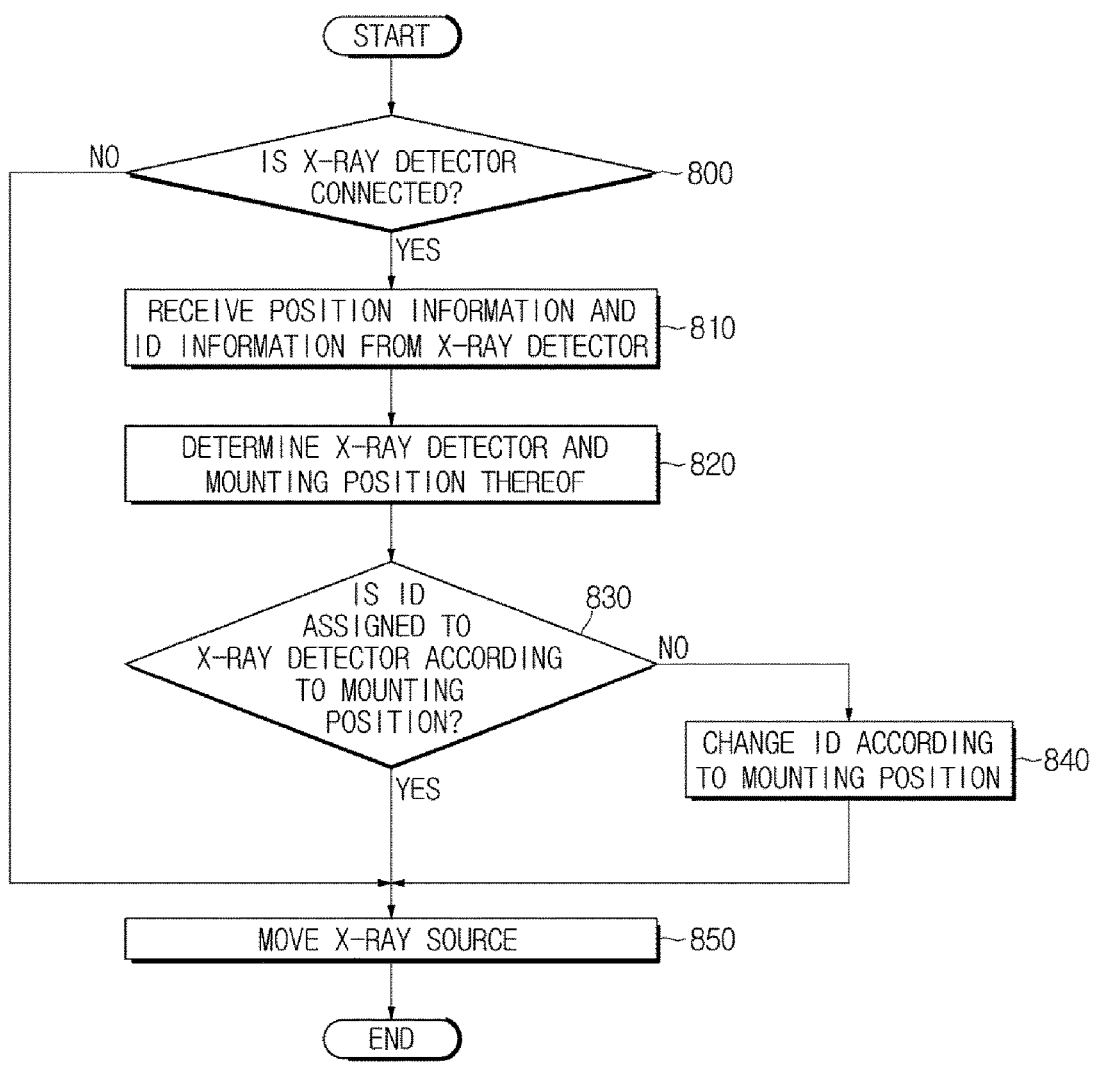
FIG. 54 is a flowchart illustrating a method of controlling an X-ray imaging apparatus according to another embodiment.

FIG. 54 is a flowchart illustrating a method of controlling an X-ray imaging apparatus according to another embodiment. When FIG. 54 is described, the same content as in the above-described embodiment will not be repeated.

As illustrated in FIG. 54, first, a connection state of the X-ray detector 100 is determined (800).

The control unit 250 transmits a connection checking signal to the X-ray detector 100 periodically and receives a response signal in response thereto so that a connection state may be checked, or the control unit 250 may check a connection state using the sensor value of the mount detecting unit 340.

When there is no connected X-ray detector 100, the process immediately ends.

When there is the connected X-ray detector 100, the control unit 250 simultaneously receives position information and ID information from each X-ray detector 100 (810). In this case, the position information includes the sensor value of the detector detecting unit 140, and the ID information includes the ID assigned to the X-ray detector 100.

The control unit 250 determines an X-ray detector and a mounting position thereof based on the received position information and ID information (820).

The control unit 250 determines whether the ID is assigned to the X-ray detector according to a mounting position (830). When the ID is not assigned according to the mounting position, the control unit 250 changes the ID according to the mounting position (840).

When the ID is assigned according to the mounting position in determining operation 830, or when the ID is changed according to the mounting position in operation 840, the control unit 250 moves the X-ray source 70 to an imaging position input by the user (850).

For example, when the table type X-ray detector 100 is provided, the user may select an imaging position as a "table" by pressing the button 84 or touching the display panel 81. According to the user's selection, the control unit 250 calculates a current position of the X-ray source 70 and a position of the X-ray detector 100 mounted in the table mounting unit 310, and outputs a control signal to the motor 90 that needs to be driven. The X-ray source 70 moves according to driving of the motor 90. The position of the X-ray source 10 corresponds to a position of the table type X-ray detector 100. Therefore, X-ray imaging may be performed or an X-ray image may be obtained in the imaging table 10.

Figure 55:
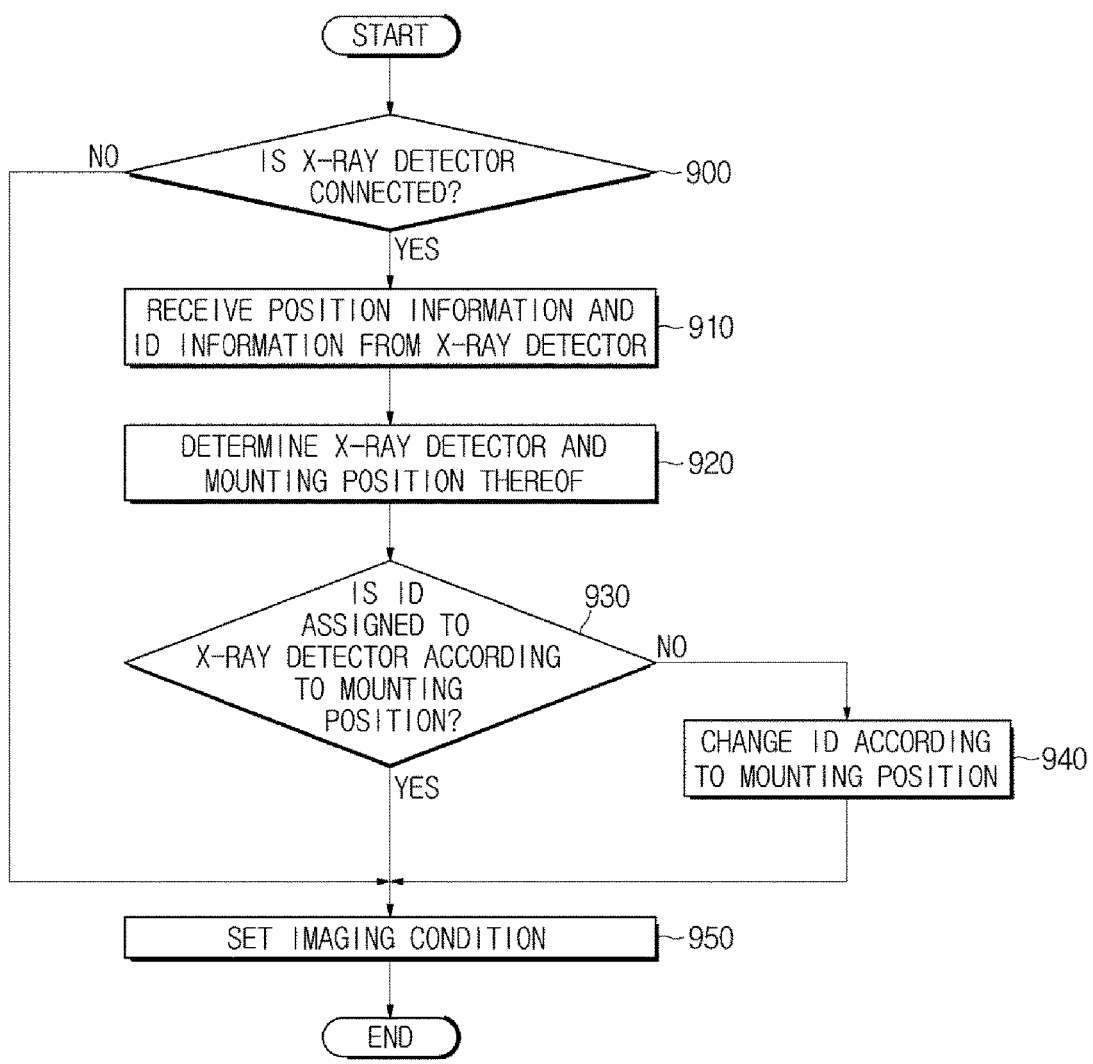
FIG. 55 is a flowchart illustrating a method of controlling an X-ray imaging apparatus according to still another embodiment.

FIG. 55 is a flowchart illustrating a method of controlling an X-ray imaging apparatus according to still another embodiment. Since operations 900 to 940 of FIG. 55 are the same as operations 700 to 740 of FIG. 34, descriptions thereof will not be repeated.

When the ID of the X-ray detector 100 is set according to the mounting position by the end of operation 940, the control unit 250 sets imaging conditions of the X-ray source 70, that is, an X-ray dose, according to an imaging position selected by the user or a position in which the X-ray detector 100 is mounted (950).

For example, when the user selects the imaging table 10 as an imaging position, or when it is determined that there is the table type X-ray detector 100, the control unit 250 may set imaging conditions at an X-ray dose that is appropriate for the part lower than the chest. On the other hand, when the user selects the imaging stand 20 as an imaging position, or when it is determined that there is the stand type X-ray detector 100, the control unit 250 may set imaging conditions at an X-ray dose that is appropriate for the chest.

Also, when the user selects portable imaging, or when it is determined that there is the portable type X-ray detector 100, the control unit 250 may set imaging conditions based on the sensor value of the detector detecting unit 140. In the example of FIG. 33, when the tilt sensor G detects a horizontal state, the control unit 250 may set imaging conditions at an X-ray dose that is appropriate for the part lower than the chest. On the other hand, when the tilt sensor G detects a non-horizontal state, the control unit 250 may set imaging conditions at an X-ray dose that is appropriate for the chest.

Figure 56:
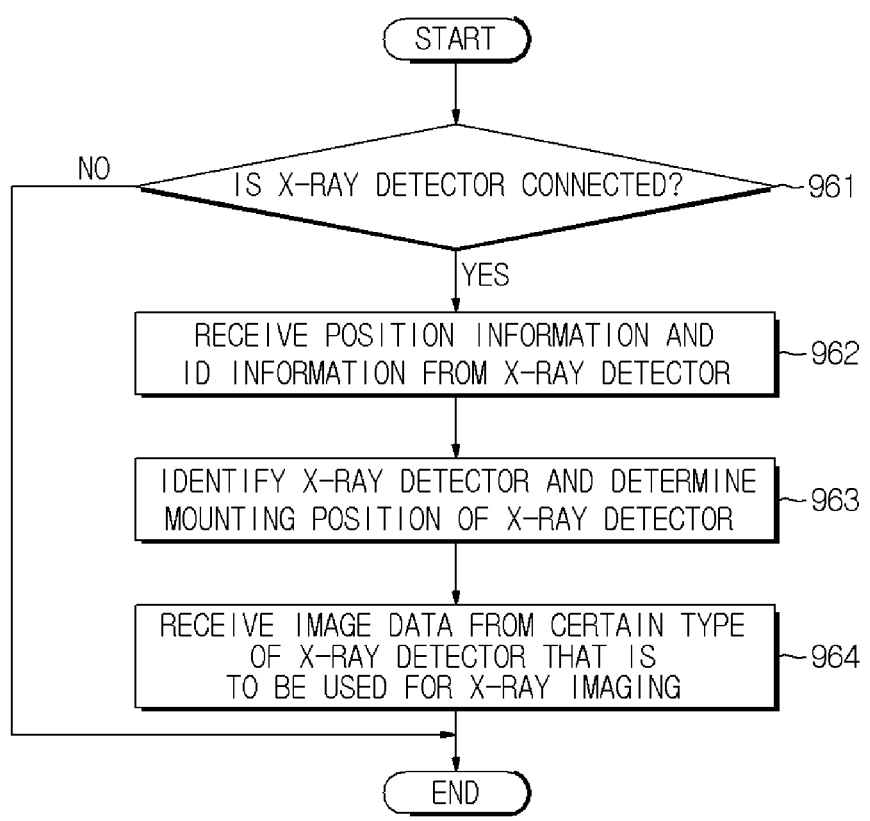
FIG. 56 is a flowchart illustrating an embodiment in which ID of the X-ray detector is not set or changed.

FIG. 56 is a flowchart illustrating an embodiment in which ID of the X-ray detector is not set or changed, which corresponds to the embodiment described above with reference to FIGS. 51 and 52.

Referring to FIG. 56, it is determined whether the X-ray detector 100 is connected (961), and when there is no connected X-ray detector 100 (NO from operation 961), the process immediately ends.

When there is the connected X-ray detector 100, the control unit 250 receives position information and ID information from the connected X-ray detector 100 (962). In this case, the position information includes the sensor value of the detector detecting unit 140, and the ID information is unique information assigned to the X-ray detector 100, and regarded as a fixed value that does not change.

The control unit 250, in particular, the position determining unit 252 may identify an X-ray detector 100 and determine a mounting position of an X-ray detector 100 based on the received position information and ID information (963). Since the ID information is unique information of each X-ray detector, an X-ray detector may be identified based on the ID information, and since the position information is information indicating a position in which an X-ray detector is provided, the mounting position of an X-ray detector may be determined based on the position information.

The process including operations 961 to 963 are identical to the process including operations 700 and 720 described above, and details thereof will be omitted.

In addition, image data may be received from a certain type of an X-ray detector that is to be used for X-ray imaging (964). The type of an X-ray detector to be used for X-ray imaging may be determined among a table type, a stand type and a portable type. The type may be determined by a user's input, or may be automatically determined depending on the position of a patient. For example, when the type to be used for X-ray imaging is a stand type, that is, when the X-ray imaging is performed on a patient who stands up, an X-ray image or relevant data thereof may be received from the stand type X-ray detector 100 mounted on the stand mounting unit 320, according to a result of operation 963 identifying an X-ray detector and determining a mounting position of an X-ray detector. That is, the stand-type X-ray detector 100 may be used for X-ray imaging. Accordingly, data may be received from the X-ray detector 100 that has been actually used for X-ray imaging without an additional input or manipulation of a user, and thus the workload of the user is reduced and repeated X-ray imaging is prevented.

While the embodiments of the X-ray detector, the X-ray imaging apparatus, and the method of controlling an X-ray imaging apparatus have been described above with reference to the exemplified drawings, it may be understood by those skilled in the art that the embodiments may be performed in other concrete forms without changing the technological scope and essential features. Therefore, the aforementioned embodiments should be considered as only examples in all aspects and not for purposes of limitation.

What is claimed is:

1. An X-ray detector that is detachably mountable in at least one mounting unit, the X-ray detector comprising:
    a memory configured to store identification (ID) information of the X-ray detector;
    a position detector configured to detect mounting position information, which is used to determine in which of the at least one mounting unit that the X-ray detector is mounted, of the X-ray detector; and
    a communicator configured to
    transmit the mounting position information of the X-ray detector and ID information of the X-ray detector to a workstation,
    wherein the position detector includes a tilt sensor configured to detect a tilt of the X-ray detector, and
    wherein the mounting position information of the X-ray detector includes an output value of the tilt sensor.

2. The X-ray detector according to claim 1, wherein the at least one mounting unit includes a table mounting unit provided in an imaging table and a stand mounting unit provided in an imaging stand.

3. The X-ray detector according to claim 1, wherein the position detecting unit further includes a magnetic sensor to detect at least one of a magnetic field direction and a magnetic field strength.

4. The X-ray detector according to claim 3, wherein the magnetic sensor includes a linear magnetic sensor to output a value corresponding to the magnetic field strength.

5. The X-ray detector according to claim 3, wherein the magnetic sensor includes a nonlinear magnetic sensor to output one of on and off according to the magnetic field strength.

6. The X-ray detector according to claim 1, further comprising an indicator to indicate whether the X-ray detector is connected to a workstation.

7. An X-ray imaging apparatus, comprising:
    at least one X-ray detector including a memory configured to store identification (ID) information, a mounting position detector configured to detect mounting position information of the at least one X-ray detector and a communicator configured to transmit the mounting position information of the at least one X-ray detector and the ID information of the at least one X-ray detector;
    at least one mounting unit in which the at least one X-ray detector is mountable; and
    a controller configured to identify the at least one X-ray detector which is mounted in one of the at least one mounting unit based on the transmitted ID information, determine an usage of the at least one X-ray detector based on the transmitted ID information and to identify the at least one mounting unit in which the at least one X-ray detector having the transmitted ID information is mounted based on the transmitted mounting position information,
    wherein the mounting position detector includes a tilt sensor configured to detect a tilt of the at least one X-ray detector,
    wherein the mounting position information includes an output value of the tilt sensor.

8. The X-ray imaging apparatus according to claim 7, wherein the at least one mounting unit includes a table mounting unit provided in an imaging table and a stand mounting unit provided in an imaging stand,
    wherein the controller determines whether the at least one X-ray detector having the transmitted ID information is mounted in the table mounting unit or in the stand mounting unit based on the output value of the tilt sensor.

9. The X-ray imaging apparatus according to claim 8, wherein the controller determines whether the at least one X-ray detector having the transmitted ID information is not mounted in the table mounting unit or in the stand mounting unit so as to be used as a portable type, based on the output value of the tilt sensor.

10. The X-ray imaging apparatus according to claim 7, wherein the at least one mounting unit includes a magnet, and
    the mounting position detector further includes one or more magnetic sensors configured to detect one of a magnetic field direction and a magnetic field strength which are caused by the magnet.

11. The X-ray imaging apparatus according to claim 8, wherein the controller is configured to determine that the at least one X-ray detector having the transmitted ID information is mounted in the stand mounting unit when the output value of the tilt sensor indicates a vertical state.

12. The X-ray imaging apparatus according to claim 8, wherein the controller is configured to determine whether the at least one X-ray detector having the transmitted ID information is mounted in the stand mounting unit or in the table mounting unit based on a user's input when the output value of the tilt sensor indicates a horizontal state.

13. The X-ray imaging apparatus according to claim 9, wherein the controller control unit is configured to determine an imaging part based on the output value of the tilt sensor when the at least one X-ray detector having the transmitted ID information is used to be as the portable type.

14. The X-ray imaging apparatus according to claim 10, wherein the controller is configured to determine whether the at least one X-ray detector having the transmitted ID is mounted in the table mounting unit or in the stand mounting unit based on output values of the magnetic sensors when the output value of the tilt sensor indicate a horizontal state.

15. The X-ray imaging apparatus according to claim 10, wherein the controller is configured to determine that the at least one X-ray detector having the transmitted ID information is used as a portable type when the output values of the magnetic sensors are less than a threshold value.

16. The X-ray imaging apparatus according to claim 15, wherein the controller is configured to determine an imaging part based on the output value of the tilt sensor.

* * * * *

UNITED STATES PATENT AND TRADEMARK OFFICE
CERTIFICATE OF CORRECTION

PATENT NO. : 10,463,337 B2  
APPLICATION NO. : 15/583529  
DATED : November 5, 2019  
INVENTOR(S) : Myeong Je Kim Page 1 of 1

It is certified that error appears in the above-identified patent and that said Letters Patent is hereby corrected as shown below:

In the Claims

Column 65, Line 4:
In Claim 13, after "controller" delete "control unit".

Signed and Sealed this  
Seventh Day of January, 2020

Andrei Iancu  
*Director of the United States Patent and Trademark Office*